(12) United States Patent
Stenkamp et al.

(10) Patent No.: US 7,592,358 B2
(45) Date of Patent: *Sep. 22, 2009

(54) ALKYNE COMPOUNDS WITH MCH ANTAGONISTIC ACTIVITY AND MEDICAMENTS COMPRISING THESE COMPOUNDS

(75) Inventors: Dirk Stenkamp, Biberach (DE); Stephan Georg Mueller, Warthausen (DE); Philipp Lustenberger, Warthausen (DE); Thorsten Lehmann-Lintz, Ochsenhausen (DE); Gerald Juergen Roth, Biberach (DE); Klaus Rudolf, Warthausen (DE); Marcus Schindler, Biberach (DE); Leo Thomas, Biberach (DE); Ralf Lotz, Schemmerhofen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 717 days.

This patent is subject to a terminal disclaimer.

(21) Appl. No.: 11/104,889

(22) Filed: Apr. 13, 2005

(65) Prior Publication Data

US 2005/0234101 A1 Oct. 20, 2005

Related U.S. Application Data

(60) Provisional application No. 60/563,590, filed on Apr. 20, 2004.

(51) Int. Cl.
  *A61K 31/47* (2006.01)
  *A61K 31/44* (2006.01)
  *A61K 31/445* (2006.01)
  *C07D 211/68* (2006.01)
  *C07D 215/00* (2006.01)
  *C07D 401/00* (2006.01)

(52) U.S. Cl. .................... 514/314; 514/318; 514/357; 514/343; 546/194; 546/334; 546/276.4; 546/278.4; 546/165

(58) Field of Classification Search .............. 514/336, 514/318, 357, 343; 546/267.4, 194, 334, 546/278.4, 165, 276.4
See application file for complete search history.

(56) References Cited

U.S. PATENT DOCUMENTS

| 6,366,268 | B1 | 4/2002 | Forrest et al. | |
| 2002/0052383 | A1 | 5/2002 | Bakthavatchalam et al. | |
| 2004/0209865 | A1* | 10/2004 | Stenkamp et al. | 514/217.03 |

FOREIGN PATENT DOCUMENTS

| EP | 0 237 678 A1 | 9/1987 |
| EP | 1 283 199 A1 | 2/2003 |
| JP | 04054118 | 2/1992 |
| JP | 2000086603 | 3/2000 |
| WO | WO 98/38156 | 9/1998 |
| WO | WO 99/02497 A2 | 1/1999 |
| WO | WO 99/29674 | 6/1999 |
| WO | WO 00/05223 | 2/2000 |
| WO | WO 00/06153 | 2/2000 |
| WO | WO 00/49005 | 8/2000 |
| WO | WO 01/02344 | 1/2001 |
| WO | WO 01/21577 | 3/2001 |
| WO | WO 01 55066 A2 | 8/2001 |
| WO | WO 01/82925 | 8/2001 |
| WO | WO 02 04433 A2 | 1/2002 |
| WO | WO 02/06245 A1 | 1/2002 |
| WO | WO 02 28182 A1 | 4/2002 |
| WO | WO 02/051809 A1 | 7/2002 |
| WO | WO 02/057233 A1 | 7/2002 |
| WO | WO 02/092068 | 11/2002 |
| WO | WO 03 013247 A1 | 2/2003 |
| WO | WO 03/014111 A1 | 2/2003 |
| WO | WO 03/018579 A1 | 3/2003 |
| WO | WO 03/032980 A1 | 4/2003 |
| WO | WO 03/033476 A1 | 4/2003 |
| WO | WO 03/035055 | 5/2003 |
| WO | WO 03 050087 A2 | 6/2003 |
| WO | WO 2004/024702 A1 | 3/2004 |
| WO | WO 2004/039764 A1 | 5/2004 |
| WO | WO 2004/039780 A1 | 5/2004 |
| WO | WO 2004/072018 | 8/2004 |

OTHER PUBLICATIONS

Patani et al., "Bioisoterism: A Rational Approach in Drug Design", Chem. Rev. 1996, pp. 3147-3176.*
Yanyun Chen, et al. "Targeted Disruption of the Melanin-Concentrating Hormone Receptor-1 Results in Hyperphagia and Resistance to Diet-Induced Obesity", Endocrinology 143(7):2469-2477 2002.
Daqing Qu, et al. "A role for melanin-concentrating hormone in the central regulation of feeding behaviour" Nature vol. 380, pp. 243-247 1996.
Masako Shimada, et al. "Mice lacking melanin-concentrating hormone are hypophagic and lean" Nature vol. 396, pp. 670-674 1998.
Beth Borowsky, et al. "Antidepressant, anxiolytic and anorectic effects of a melanin-concentrating hormone-1 receptor antagonist" Nature Medicine vol. 8, No. 8, pp. 825-830, 2002.
Donald J. Marsh, et al. "Melanin-concentrating hormone 1 receptor-deficient mice are lean, hyperactive, and hyperphagic and have altered metabolism" PNAS, vol. 99, No. 5, pp. 3240-3245, 2002.
Shiro Takekawa, et al. "T-226296: a novel, orally active and selective melanin-concentrating hormone receptor antagonist" E. Journal of Pharm. vol. 438, pp. 129-135, 2002.

(Continued)

Primary Examiner—Janet L Andres
Assistant Examiner—Binta M Robinson
(74) Attorney, Agent, or Firm—Michael P. Morris; Mary-Ellen M. Devlin; Timothy X. Witkowski

(57) ABSTRACT

Alkyne compounds having MCH-receptor antagonistic activity, which are useful for preparing pharmaceutical compositions for the treatment of metabolic disorders and/or eating disorders, particularly obesity and diabetes.

18 Claims, No Drawings

OTHER PUBLICATIONS

J. Krapcho, et al; "Immunosuppresive Activity of 2'-(3-Dimethylaminopropylthio)cinnamanilide (Cinanserin) and Relateld Compounds" J. Med. Chemistry. 1969, 12(1), 164-166.

Stenkamp, D. et al; U.S. Appl. No. 11/104,915—Alkyne Compounds with MCH Antagonistic Activity and Medicaments Comprising These Compounds filed Apr. 13, 2005.

Stenkamp, D. et al; U.S. Appl. No. 11/105,010—Alkyne Compounds with MCH Antagonistic Activity and Medicaments Comprising These Compounds filed Apr. 13, 2005.

Stenkamp, D. et al; U.S. Appl. No. 11/104,914—Alkyne Compounds with MCH Antagonistic Activity and Medicaments Comprising These Compounds filed Apr. 13, 2005.

Stenkamp, D. et al; U.S. Appl. No. 11/104,832- Alkyne Compounds with MCH Antagonistic Activity and Medicaments Comprising These Compounds filed Apr. 13, 2005.

\* cited by examiner

ALKYNE COMPOUNDS WITH MCH ANTAGONISTIC ACTIVITY AND MEDICAMENTS COMPRISING THESE COMPOUNDS

RELATED APPLICATIONS

This application claims benefit of U.S. Ser. No. 60/563,590, filed Apr. 20, 2004, and claims priority to German Application No. 10 2004 017 934.4, filed Apr. 14, 2004, each of which is hereby incorporated by reference in its entirety.

FIELD OF THE INVENTION

The present invention relates to new alkyne compounds, the physiologically acceptable salts thereof as well as their use as MCH antagonists and their use in preparing a pharmaceutical preparation which is suitable for the prevention and/or treatment of symptoms and/or diseases caused by MCH or causally connected with MCH in some other way. The invention also relates to the use of a compound according to the invention for influencing eating behavior and for reducing body weight and/or for preventing any increase in body weight in a mammal. It further relates to compositions and medicaments containing a compound according to the invention and processes for preparing them.

BACKGROUND OF THE INVENTION

The intake of food and its conversion in the body is an essential part of life for all living creatures. Therefore, deviations in the intake and conversion of food generally lead to problems and also illness. The changes in the lifestyle and nutrition of humans, particularly in industrialized countries, have promoted morbid overweight (also known as corpulence or obesity) in recent decades. In affected people, obesity leads directly to restricted mobility and a reduction in the quality of life. There is the additional factor that obesity often leads to other diseases such as, for example, diabetes, dyslipidemia, high blood pressure, arteriosclerosis, and coronary heart disease. Moreover, high bodyweight alone puts an increased strain on the support and mobility apparatus, which can lead to chronic pain and diseases such as arthritis or osteoarthritis. Thus, obesity is a serious health problem for society.

The term obesity means an excess of adipose tissue in the body. In this connection, obesity is fundamentally to be seen as the increased level of fatness which leads to a health risk. There is no sharp distinction between normal individuals and those suffering from obesity, but the health risk accompanying obesity is presumed to rise continuously as the level of fatness increases. For simplicity's sake, in the present invention, individuals with a Body Mass Index (BMI), which is defined as the bodyweight measured in kilograms divided by the height (in meters) squared, above a value of 25 and more particularly above 30, are preferably regarded as suffering from obesity.

Apart from physical activity and a change in nutrition, there is currently no convincing treatment option for effectively reducing bodyweight. As obesity is a major risk factor in the development of serious and even life-threatening diseases, however, it is all the more important to have access to pharmaceutical active substances for the prevention and/or treatment of obesity. One approach which has been proposed very recently is the therapeutic use of MCH antagonists (cf. inter alia WO 01/21577 and WO 01/82925).

Melanin-concentrating hormone (MCH) is a cyclic neuropeptide consisting of 19 amino acids. It is synthesized predominantly in the hypothalamus in mammals and from there travels to other parts of the brain by the projections of hypothalamic neurons. Its biological activity is mediated in humans through two different glycoprotein-coupled receptors (GPCRs) from the family of rhodopsin-related GPCRs, namely the MCH receptors 1 and 2 (MCH-1R, MCH-2R).

Investigations into the function of MCH in animal models have provided good indications for a role of the peptide in regulating the energy balance, i.e., changing metabolic activity and food intake. D. Qu, et al., *A role for melanin-concentrating hormone in the central regulation of feeding behavior*, Nature, 1996, 380(6571): pp. 243-7; M. Shimada, et al., *Mice lacking melanin-concentrating hormone are hypophagic and lean*, Nature, 1998, 396(6712): pp. 670-4. For example, after intraventricular administration of MCH in rats, food intake was increased compared with control animals. Additionally, transgenic rats which produce more MCH than control animals, when given a high-fat diet, responded by gaining significantly more weight than animals without an experimentally altered MCH level. It was also found that there is a positive correlation between phases of increased desire for food and the quantity of MCH mRNA in the hypothalamus of rats. However, experiments with MCH knock-out mice are particularly important in showing the function of MCH. Loss of the neuropeptide results in lean animals with a reduced fat mass, which take in significantly less food than control animals.

The anorectic effects of MCH are presumably mediated in rodents through the G-Galpha i-coupled MCH-1R [B. Borowsky, et al., *Antidepressant, anxiolytic and anorectic effects of a melanin-concentrating hormone-1 receptor antagonist*, Nat Med, 2002, 8(8): pp. 825-30; Y. Chen, et al., *Targeted disruption of the melanin-concentrating hormone receptor-1 results in hyperphagia and resistance to diet-induced obesity*, Endocrinology, 2002, 143(7): pp. 2469-77; D. J. Marsh, et al., *Melanin-concentrating hormone 1 receptor-deficient mice are lean, hyperactive, and hyperphagic and have altered metabolism*. Proc Natl Acad Sci USA, 2002, 99(5): pp. 3240-5; S. Takekawa, et al., T-226296: *A novel, orally active and selective melanin-concentrating hormone receptor antagonist*. Eur J Pharmacol, 2002, 438(3): pp. 129-35.], as, unlike primates, ferrets, and dogs, no second MCH receptor subtype has hitherto been found in rodents. After losing the MCH-1R, knock-out mice have a lower fat mass, an increased energy conversion and, when fed on a high fat diet, do not put on weight, compared with control animals. Another indication of the importance of the MCH system in regulating the energy balance results from experiments with a receptor antagonist (SNAP-7941). B. Borowsky, et al., Nat Med, 2002, 8(8): pp. 825-30. In long term trials, the animals treated with the antagonist lose significant amounts of weight.

In addition to its anorectic effect, the MCH-1R antagonist SNAP-7941 also achieves additional anxiolytic and antidepressant effects in behavioral experiments on rats. B. Borowsky, et al., Nat Med, 2002, 8(8): pp. 825-30. Thus, there are clear indications that the MCH-MCH-IR system is involved not only in regulating the energy balance but also in affectivity.

In the patent literature certain amine compounds are proposed as MCH antagonists. Thus, WO 01/21577 (Takeda) describes compounds of formula

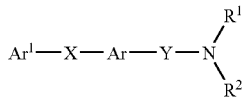

wherein Ar¹ denotes a cyclic group, X denotes a spacer, Y denotes a bond or a spacer, Ar denotes an aromatic ring which may be fused with a non-aromatic ring, R¹ and R² independently of one another denote H or a hydrocarbon group, while R¹ and R² together with the adjacent N atom may form an N-containing hetero ring and R² with Ar may also form a spirocyclic ring, and R together with the adjacent N atom and Y may form an N-containing hetero ring, as MCH antagonists for the treatment of obesity.

Moreover WO 01/82925 (Takeda) also describes compounds of formula

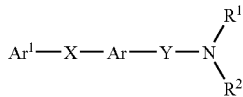

wherein Ar¹ denotes a cyclic group, X and Y represent spacer groups, Ar denotes an optionally substituted fused polycyclic aromatic ring, R¹ and R² independently of one another represent H or a hydrocarbon group, while R¹ and R² together with the adjacent N atom may form an N-containing heterocyclic ring and R² together with the adjacent N atom and Y may form an N-containing hetero ring, as MCH antagonists for the treatment of obesity, inter alia.

WO 2004/024702 proposes carboxylic acid amide compounds of formula I

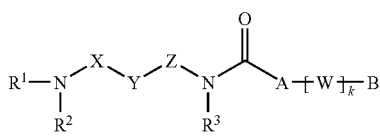

wherein Y, A, and B may represent cyclic groups and X, Z, and W may denote bridges or bonds, as MCH-antagonists.

WO 04/039780 A1 describes alkyne compounds of formula I

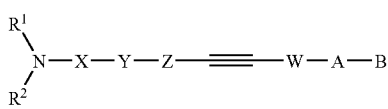

wherein Y, A, and B may denote cyclic groups and X, Z, and W may denote bridges or bonds, as MCH-antagonists.

WO 04/039764 A1 describes amide compounds of formula I

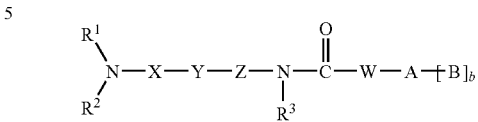

wherein Y, A, and B may denote cyclic groups and X denotes an alkylene bridge, Z denotes a bridge or bond and W is selected from the group comprising $-CR^{6a}R^{6b}-O-$, $-CR^{7a}=CR^{7c}$, $-CR^{6a}R^{6b}-NR^{8}$, $-CR^{7a}R^{7b}-CR^{7c}R^{7d}-$, and $-NR^{8}-CR^{6a}R^{6b}-$, as MCH-antagonists.

The aim of the present invention is to identify new alkyne compounds, particularly those which are especially effective as MCH antagonists. The invention also sets out to provide new alkyne compounds which can be used to influence the eating habits of mammals and achieve a reduction in body weight, particularly in mammals, and/or prevent an increase in body weight.

The present invention further sets out to provide new pharmaceutical compositions which are suitable for the prevention and/or treatment of symptoms and/or diseases caused by MCH or otherwise causally connected to MCH. In particular, the aim of this invention is to provide pharmaceutical compositions for the treatment of metabolic disorders such as obesity and/or diabetes as well as diseases and/or disorders which are associated with obesity and diabetes. Other objectives of the present invention are concerned with demonstrating advantageous uses of the compounds according to the invention. The invention also sets out to provide a process for preparing the amide compounds according to the invention. Other aims of the present invention will be immediately apparent to the skilled man from the foregoing remarks and those that follow.

In a first aspect, the present invention relates to alkyne compounds selected from the list comprising:

| No. | Name |
|---|---|
| 1.1 | (2-{4-[5-(4-chlorophenyl)pyridin-2-ylethynyl]-2-methylphenoxy}ethyl)cyclopropylmethylamine |
| 1.2 | (2-{4-[5-(4-chlorophenyl)pyridin-2-ylethynyl]-2-methylphenoxy}ethyl)cyclopentylamine |
| 1.3 | (2-{4-[5-(4-chlorophenyl)pyridin-2-ylethynyl]-2-methylphenoxy}ethyl)cyclopentylmethylamine |
| 1.4 | 5-(4-chlorophenyl)-2-{4-[2-((S)-2-methoxymethylpyrrolidin-1-yl)ethoxy]-3-methylphenylethynyl}pyridine |
| 1.5 | 5-(4-chlorophenyl)-2-{4-[2-((R)-2-methoxymethylpyrrolidin-1-yl)ethoxy]-3-methylphenylethynyl}pyridine |
| 1.6 | 1-(2-{4-[5-(4-chlorophenyl)pyridin-2-ylethynyl]-2-methylphenoxy}ethyl)-4-trifluoromethylpiperidin-4-ol |
| 1.7 | 1-[1-(2-{4-[5-(4-chlorophenyl)pyridin-2-ylethynyl]-2-methylphenoxy}ethyl)piperidin-4-yl]-2,2,2-trifluoroethanol |
| 1.8 | 1-[1-(2-{4-[5-(4-chlorophenyl)pyridin-2-ylethynyl]-2-methylphenoxy}ethyl)piperidin-4-yl]-2,2,2-trifluoroethanone |
| 1.9 | (2-{4-[5-(4-chlorophenyl)pyridin-2-ylethynyl]-2-methylphenoxy}ethyl)cyclohexylcyclopentylamine |
| 1.10 | (3S,4R)-1-(2-{4-[5-(4-chlorophenyl)pyridin-2-ylethynyl]-2-methylphenoxy}ethyl)-4-trifluoromethylpiperidin-3,4-diol |
| 1.11 | (3R,4S)-1-(2-{4-[5-(4-chlorophenyl)pyridin-2-ylethynyl]-2-methylphenoxy}ethyl)-4-trifluoromethylpiperidin-3,4-diol |

| No. | Name |
|---|---|
| 1.12 | 2-(2-{4-[5-(4-chlorophenyl)pyridin-2-ylethynyl]-2-methylphenoxy}ethylamino)-2-methylpropan-1-ol |
| 1.13 | [1-(2-{4-[5-(4-chlorophenyl)pyridin-2-ylethynyl]-2-methylphenoxy}ethyl-amino)cyclopentyl]methanol |
| 2.1 | (2-{4-[5-(4-chlorophenyl)pyridin-2-ylethynyl]-2-methylphenoxy}ethyl)cyclohexyl-cyclopropylmethylamine |
| 2.2 | (2-{4-[5-(4-chlorophenyl)pyridin-2-ylethynyl]-2-methylphenoxy}ethyl)dicyclopentylamine |
| 2.3 | (2-{4-[5-(4-chlorophenyl)pyridin-2-ylethynyl]-2-methylphenoxy}ethyl)cyclopentyl-cyclopropylmethylamine |
| 2.4 | (2-{4-[5-(4-chlorophenyl)pyridin-2-ylethynyl]-2-methylphenoxy}ethyl)cyclopentylmethyl-cyclopropylmethylamine |
| 2.5 | (2-{4-[5-(4-chlorophenyl)pyridin-2-ylethynyl]-2-methylphenoxy}ethyl)cyclopentyl-cyclopentylmethylamine |
| 2.6 | (2-{4-[5-(4-chlorophenyl)pyridin-2-ylethynyl]-2-methylphenoxy}ethyl)cyclohexylcyclopentylmethylamine |
| 3.1 | 2-[(2-{4-[5-(4-chlorophenyl)pyridin-2-ylethynyl]-2-methylphenoxy}ethyl)cyclopentylamino]ethanol |
| 3.2 | 3-[(2-{4-[5-(4-chlorophenyl)pyridin-2-ylethynyl]-2-methylphenoxy}ethyl)cyclopentylamino]propan-1-ol |
| 3.3 | 3-[(2-{4-[5-(4-chlorophenyl)pyridin-2-ylethynyl]-2-methylphenoxy}ethyl)cyclopentyl-methylamino]propan-1-ol |
| 3.4 | 2-[(2-{4-[5-(4-chlorophenyl)pyridin-2-ylethynyl]-2-methylphenoxy}ethyl)cyclopentylmethylamino]ethanol |
| 4.2 | (2-{4-[5-(4-chlorophenyl)pyridin-2-ylethynyl]phenoxy}ethyl)cyclohexyl-cyclopropylmethylamine |
| 4.3 | 1-(2-{4-[5-(4-chlorophenyl)pyridin-2-ylethynyl]phenoxy}ethyl)-4-trifluoromethylpiperidin-4-ol |
| 4.4 | 1-[1-(2-{4-[5-(4-chlorophenyl)pyridin-2-ylethynyl]phenoxy}ethyl)piperidin-4-yl]-2,2,2-trifluoroethanol |
| 4.5 | 1-[1-(2-{4-[5-(4-chlorophenyl)pyridin-2-ylethynyl]phenoxy}ethyl)piperidin-4-yl]-2,2,2-trifluoroethanone |
| 4.6 | (2-{4-[5-(4-chlorophenyl)pyridin-2-ylethynyl]phenoxy}ethyl)cyclopropyl-methylpropylamine |
| 4.7 | (3S,4R)-1-(2-{4-[5-(4-chlorophenyl)pyridin-2-ylethynyl]phenoxy}ethyl)-4-trifluoromethylpiperidin-3,4-diol |
| 4.8 | (3R,4S)-1-(2-{4-[5-(4-chlorophenyl)pyridin-2-ylethynyl]phenoxy}ethyl)-4-trifluoromethylpiperidin-3,4-diol |
| 4.9 | 8-(2-{4-[5-(4-chlorophenyl)pyridin-2-ylethynyl]phenoxy}ethyl)-3-methyl-8-azabicyclo[3.2.1]octan-3-ol |
| 4.10 | 8-(2-{4-[5-(4-chlorophenyl)pyridin-2-ylethynyl]phenoxy}ethyl)-3-ethyl-8-azabicyclo[3.2.1]octan-3-ol |
| 4.11 | exo-8-(2-{4-[5-(4-chlorophenyl)pyridin-2-ylethynyl]phenoxy}ethyl)-3-trifluoromethyl-8-azabicyclo[3.2.1]octan-3-ol |
| 4.12 | endo-8-(2-{4-[5-(4-chlorophenyl)pyridin-2-ylethynyl]phenoxy}ethyl)-3-trifluoromethyl-8-azabicyclo[3.2.1]octan-3-ol |
| 4.13 | (R)-2-(2-{4-[5-(4-chlorophenyl)pyridin-2-ylethynyl]phenoxy}ethylamino)propan-1-ol |
| 4.14 | 2-(2-{4-[5-(4-chlorophenyl)pyridin-2-ylethynyl]phenoxy}ethylamino)-2-methylpropan-1-ol |
| 4.15 | [1-(2-{4-[5-(4-chlorophenyl)pyridin-2-ylethynyl]phenoxy}ethylamino)cyclopentyl]methanol |
| 5.1 | (2-{4-[5-(4-chlorophenyl)pyridin-2-ylethynyl]phenoxy}ethyl)cyclopentyl-cyclopropylmethylamine |
| 6.1 | 3-[(2-{4-[5-(4-chlorophenyl)pyridin-2-ylethynyl]phenoxy}ethyl)cyclopropyl-methylamino]propan-1-ol |
| 7.2 | 2-[4-(2-azetidin-1-ylethoxy)phenylethynyl]-5-(4-chlorophenyl)-3-fluoropyridine |
| 7.3 | 5-(4-chlorophenyl)-3-fluoro-2-{4-[2-((S)-2-methoxymethylpyrrolidin-1-yl)ethoxy]phenylethynyl}pyridine |
| 7.4 | 8-(2-{4-[5-(4-chlorophenyl)-3-fluoropyridin-2-ylethynyl]phenoxy}ethyl)-8-azabicyclo[3.2.1]octan-3-ol |
| 7.5 | [1-(2-{4-[5-(4-chlorophenyl)-3-fluoropyridin-2-ylethynyl]phenoxy}ethyl)piperidin-4-yl]methanol |
| 7.6 | 1-(2-{4-[5-(4-chlorophenyl)-3-fluoropyridin-2-ylethynyl]phenoxy}ethyl)piperidin-3-ol |
| 7.7 | (3R,4S)-1-(2-{4-[5-(4-chlorophenyl)-3-fluoropyridin-2-ylethynyl]phenoxy}ethyl)-4-methylpiperidin-3,4-diol |
| 7.8 | 1-(2-{4-[5-(4-chlorophenyl)-3-fluoropyridin-2-ylethynyl]phenoxy}ethyl)-4-trifluoromethylpiperidin-4-ol |
| 7.9 | 1-[(S)-1-(2-{4-[5-(4-chlorophenyl)-3-fluoropyridin-2-ylethynyl]phenoxy}ethyl)pyrrolidin-2-yl]cyclopropanol |
| 8.1 | [(S)-1-(2-{4-[5-(4-chlorophenyl)-3-fluoropyridin-2-ylethynyl]phenoxy}ethyl)-2-methylpyrrolidin-2-yl]methanol |
| 8.2 | 5-(4-chlorophenyl)-3-fluoro-2-{4-[2-((S)-2-methoxymethylpyrrolidin-1-yl)ethoxy]-3-methylphenylethynyl}pyridine |
| 8.3 | 5-(4-chlorophenyl)-3-fluoro-2-{3-methyl-4-[2-(4-methylpiperidin-1-yl)ethoxy]phenyl-ethynyl}pyridine |
| 8.4 | 8-(2-{4-[5-(4-chlorophenyl)-3-fluoropyridin-2-ylethynyl]-2-methylphenoxy}ethyl)-8-azabicyclo[3.2.1]octan-3-ol |
| 8.5 | 1-[(S)-1-(2-{4-[5-(4-chlorophenyl)-3-fluoropyridin-2-ylethynyl]-2-methylphenoxy}ethyl)pyrrolidin-2-yl]cyclopropanol |
| 8.6 | 1-(2-{4-[5-(4-chlorophenyl)-3-fluoropyridin-2-ylethynyl]-2-methylphenoxy}ethyl)-4-methylpiperidin-4-ol |
| 9.1 | [(S)-1-(2-{2-bromo-4-[5-(4-chlorophenyl)-3-fluoropyridin-2-ylethynyl]phenoxy}ethyl)pyrrolidin-2-yl]methanol |
| 9.2 | 1-[(S)-1-(2-{2-bromo-4-[5-(4-chlorophenyl)-3-fluoropyridin-2-ylethynyl]phenoxy}ethyl)pyrrolidin-2-yl]cyclopropanol |
| 9.3 | 2-{3-bromo-4-[2-((S)-2-methoxymethylpyrrolidin-1-yl)ethoxy]phenylethynyl}-5-(4-chlorophenyl)-3-fluoropyridine |
| 9.4 | 1-(2-{2-bromo-4-[5-(4-chlorophenyl)-3-fluoropyridin-2-ylethynyl]phenoxy}ethyl)-4-methylpiperidin-4-ol |
| 9.5 | 2-{3-bromo-4-[2-(4-methylpiperidin-1-yl)ethoxy]phenylethynyl}-5-(4-chlorophenyl)-3-fluoropyridine |
| 9.6 | 8-(2-{2-bromo-4-[5-(4-chlorophenyl)-3-fluoropyridin-2-ylethynyl]phenoxy}ethyl)-8-azabicyclo[3.2.1]octan-3-ol |
| 10.1 | 5-[5-(4-chlorophenyl)pyridin-2-ylethynyl]-1-[2-(4-methylpiperidin-1-yl)ethyl]-1H-indazole |
| 10.2 | [(S)-1-(2-{5-[5-(4-chlorophenyl)pyridin-2-ylethynyl]indazol-1-yl}ethyl)pyrrolidin-2-yl]methanol |
| 10.3 | 1-(2-{5-[5-(4-chlorophenyl)pyridin-2-ylethynyl]indazol-1-yl}ethyl)-4-methylpiperidin-4-ol |
| 10.4 | 5-[5-(4-chlorophenyl)pyridin-2-ylethynyl]-1-[2-(2,6-dimethylpiperidin-1-yl)ethyl]-1H-indazole |
| 11.1 | 5-(4-chlorophenyl)-2-{4-[2-(4-methylpiperidin-1-yl)ethoxy]-3-vinylphenylethynyl}pyridine |
| 11.2 | 1-(2-{4-[5-(4-chlorophenyl)pyridin-2-ylethynyl]-2-vinylphenoxy}ethyl)-4-methylpiperidin-4-ol |
| 11.3 | [(S)-1-(2-{4-[5-(4-chlorophenyl)pyridin-2-ylethynyl]-2-vinylphenoxy}ethyl)pyrrolidin-2-yl]methanol |
| 11.4 | 5-(4-chlorophenyl)-2-{4-[2-(4,4-dimethylpiperidin-1-yl)ethoxy]-3-vinylphenylethynyl}pyridine |
| 12.1 | 5-(4-chlorophenyl)-2-{3-isopropenyl-4-[2-(4-methylpiperidin-1-yl)ethoxy]phenylethynyl}pyridine |
| 12.2 | [(S)-1-(2-{4-[5-(4-chlorophenyl)pyridin-2-ylethynyl]-2-isopropenylphenoxy}ethyl)pyrrolidin-2-yl]methanol |
| 12.3 | 1-(2-{4-[5-(4-chlorophenyl)pyridin-2-ylethynyl]-2-isopropenylphenoxy}ethyl)-4-methylpiperidin-4-ol |
| 12.4 | 5-(4-chlorophenyl)-2-{4-[2-(4,4-dimethylpiperidin-1-yl)ethoxy]-3-isopropenylphenylethynyl}pyridine |
| 12.5 | 1-(2-{4-[5-(4-chlorophenyl)pyridin-2-ylethynyl]-2-isopropenylphenoxy}ethyl)-4-trifluoromethylpiperidin-4-ol |
| 13.1 | 1-{5-[5-(4-chlorophenyl)pyridin-2-ylethynyl]-2-[2-(4-methylpiperidin-1-yl)ethoxy]phenyl}ethanone |
| 13.2 | 1-{5-[5-(4-chlorophenyl)pyridin-2-ylethynyl]-2-[2-((S)-2-hydroxymethylpyrrolidin-1-yl)ethoxy]phenyl}ethanone |
| 13.3 | 1-{5-[5-(4-chlorophenyl)pyridin-2-ylethynyl]-2-[2-(4-hydroxy-4-methylpiperidin-1-yl)ethoxy]phenyl}ethanone |
| 13.4 | 1-{5-[5-(4-chlorophenyl)pyridin-2-ylethynyl]-2-[2-(4,4-dimethylpiperidin-1-yl)ethoxy]phenyl}ethanone |
| 13.5 | 1-{5-[5-(4-chlorophenyl)pyridin-2-ylethynyl]-2-[2-(4-hydroxy-4-trifluoromethylpiperidin-1-yl)ethoxy]phenyl}ethanone |
| 14.1 | 5-[5-(4-chlorophenyl)pyridin-2-ylethynyl]-2-[2-(4-methylpiperidin-1-yl)ethoxy]benzaldehyde-O-methyloxime |

-continued

| No. | Name |
|---|---|
| 14.2 | 5-[5-(4-chlorophenyl)pyridin-2-ylethynyl]-2-[2-((S)-2-hydroxymethylpyrrolidin-1-yl)ethoxy]benzaldehyde-O-methyloxime |
| 14.3 | 5-[5-(4-chlorophenyl)pyridin-2-ylethynyl]-2-[2-(4-hydroxypiperidin-1-yl)ethoxy]benzaldehyde-O-methyloxime |
| 14.4 | 5-[5-(4-chlorophenyl)pyridin-2-ylethynyl]-2-[2-(2,6-dimethylpiperidin-1-yl)ethoxy]benzaldehyde-O-methyloxime |
| 14.5 | 5-[5-(4-chlorophenyl)pyridin-2-ylethynyl]-2-[2-(3,5-dimethylpiperidin-1-yl)ethoxy]benzaldehyde-O-methyloxime |
| 15.1 | 5-[5-(4-chlorophenyl)pyridin-2-ylethynyl]-2-[2-(4-methylpiperidin-1-yl)ethoxy]benzaldehydeoxime |
| 15.2 | 5-[5-(4-chlorophenyl)pyridin-2-ylethynyl]-2-[2-((S)-2-hydroxymethylpyrrolidin-1-yl)ethoxy]benzaldehydeoxime |
| 15.3 | 5-[5-(4-chlorophenyl)pyridin-2-ylethynyl]-2-[2-(4-hydroxypiperidin-1-yl)ethoxy]benzaldehydeoxime |
| 15.4 | 5-[5-(4-chlorophenyl)pyridin-2-ylethynyl]-2-[2-(2,6-dimethylpiperidin-1-yl)ethoxy]benzaldehydeoxime |
| 15.5 | 5-[5-(4-chlorophenyl)pyridin-2-ylethynyl]-2-[2-(3,5-dimethylpiperidin-1-yl)ethoxy]benzaldehydeoxime |
| 16.1 | 3-bromo-5-(4-chlorophenyl)-2-{4-[2-(4-methylpiperidin-1-yl)ethoxy]phenylethynyl}pyridine |
| 17.1 | 5-(4-chlorophenyl)-3-methyl-2-{4-[2-(4-methylpiperidin-1-yl)ethoxy]phenylethynyl}pyridine |
| 18.1 | 3-methyl-2-{4-[2-(4-methylpiperidin-1-yl)ethoxy]phenylethynyl}-5-p-tolylpyridine |
| 19.1 | 5-(4-chlorophenyl)-2-{4-[2-(4-methylpiperidin-1-yl)ethoxy]phenylethynyl}pyridin-3-ylamine |
| 20.1 | {4-[5-(4-chlorophenyl)pyridin-2-ylethynyl]-2-methylphenyl}-[2-(4-methylpiperidin-1-yl)ethyl]amine |
| 21.1 | 3-chloro-5-(4-chlorophenyl)-2-{4-[2-(4-methylpiperidin-1-yl)ethoxy]phenylethynyl}pyridine |
| 21.2 | [(S)-1-(2-{4-[3-chloro-5-(4-chlorophenyl)pyridin-2-ylethynyl]phenoxy}ethyl)pyrrolidin-2-yl]methanol |
| 21.3 | 1-(2-{4-[3-chloro-5-(4-chlorophenyl)pyridin-2-ylethynyl]phenoxy}ethyl)-4-methylpiperidin-4-ol |
| 22.1 | 5-(4-chlorophenyl)-2-[2-(4-methylpiperidin-1-ylmethyl)benzo[b]thiophen-5-ylethynyl]pyridine |
| 22.2 | ((S)-1-{5-[5-(4-chlorophenyl)pyridin-2-ylethynyl]benzo[b]thiophen-2-ylmethyl}pyrrolidin-2-yl)methanol |
| 22.3 | 1-{5-[5-(4-chlorophenyl)pyridin-2-ylethynyl]benzo[b]thiophen-2-ylmethyl}-4-methylpiperidin-4-ol |
| 22.4 | 1-{5-[5-(4-chlorophenyl)pyridin-2-ylethynyl]benzo[b]thiophen-2-ylmethyl}-4-trifluoromethylpiperidin-4-ol |
| 23.1 | 5-(4-chlorophenyl)-2-{3-methyl-4-[3-(4-methylpiperidin-1-yl)propyl]phenylethynyl}pyridine |
| 24.1 | 5-(4-chlorophenyl)-2-[3-ethyl-4-(2-pyrrolidin-1-ylethoxy)phenylethynyl]pyridine |
| 25.1 | 4-(6-{4-[2-(4-methylpiperidin-1-yl)ethoxy]phenylethynyl}pyridin-3-yl)benzaldehyde |
| 26.1 | 1-[5-[5-(4-chlorophenyl)pyridin-2-ylethynyl]-2-(2-pyrrolidin-1-ylethoxy)phenyl]ethanol |
| 27.1 | 1-{5-[5-(4-chlorophenyl)pyridin-2-ylethynyl]-2-[2-(4-methylpiperidin-1-yl)ethoxy]phenyl}ethanol |
| 28.1 | {5-[5-(4-chlorophenyl)pyridin-2-ylethynyl]thiophen-3-yl}-[2-(4-methylpiperidin-1-yl)ethyl]amine |
| 29.1 | 5-(4-difluoromethylphenyl)-2-{4-[2-(4-methylpiperidin-1-yl)ethoxy]phenylethynyl}pyridine |
| 30.1 | 5-[5-(4-chlorophenyl)pyridin-2-ylethynyl]-2-(2-pyrrolidin-1-ylethoxy)benzylamine |
| 31.1 | N-(5-(4-chlorophenyl)-2-{4-[2-(4-methylpiperidin-1-yl)ethoxy]phenylethynyl}pyridin-3-yl)acetamide |
| 32.1 | 6-[5-(4-chlorophenyl)pyridin-2-ylethynyl]-4-methyl-2-(4-methylpiperidin-1-ylmethyl)quinoline |
| 33.1 | 5-[5-(4-chlorophenyl)pyridin-2-ylethynyl]-2-(2-pyrrolidin-1-ylethoxy)phenol |
| 34.1 | 5-(4-chlorophenyl)-2-[3-propoxy-4-(2-pyrrolidin-1-ylethoxy)phenylethynyl]pyridine |
| 34.2 | 5-(4-chlorophenyl)-2-[3-ethoxy-4-(2-pyrrolidin-1-ylethoxy)phenylethynyl]pyridine |
| 35.1 | 5-(4-chlorophenyl)-2-[3-isopropoxy-4-(2-pyrrolidin-1-ylethoxy)phenylethynyl]pyridine |
| 36.1 | (3-{5-[5-(4-chlorophenyl)pyridin-2-ylethynyl]pyridin-2-yl}propyl)-4-methylpiperidine |
| 37.1 | tert-butyl (S)2-({4-[5-(4-chlorophenyl)pyridin-2-ylethynyl]phenylamino}methyl)pyrrolidine-1-carboxylate |
| 38.1 | 2-{4-[5-(4-chlorophenyl)pyridin-2-ylethynyl]phenoxy}-N,N-diethylbenzamide |
| 39.1 | cis-4-methyl-1-(6-{4-[2-(4-methylpiperidin-1-yl)ethoxy]phenylethynyl}pyridin-3-yl)cyclohexanol |
| 40.1 | trans-4-methyl-1-(6-{4-[2-(4-methylpiperidin-1-yl)ethoxy]phenylethynyl}pyridin-3-yl)cyclohexanol |
| 41.1 | 1-{5-[5-(4-chlorophenyl)pyridin-2-ylethynyl]-2-[2-(4-methylpiperidin-1-yl)ethoxy]phenyl}-2,2,2-trifluoroethanol |
| 42.1 | {4-[5-(4-chlorophenyl)pyridin-2-ylethynyl]phenyl}-(S)-1-pyrrolidin-2-ylmethylamine |
| 43.1 | (5-(4-chlorophenyl)-2-{4-[2-(4-methylpiperidin-1-yl)ethoxy]phenylethynyl}pyridin-3-yl)methylamine |
| 44.1 | (5-(4-chlorophenyl)-2-{4-[2-(4-methylpiperidin-1-yl)ethoxy]phenylethynyl}pyridin-3-yl)dimethylamine |
| 45.1 | 5-(4-methylcyclohex-1-enyl)-2-{4-[2-(4-methylpiperidin-1-yl)ethoxy]phenylethynyl}pyridine |
| 46.1 | N'-{5-[5-(4-chlorophenyl)pyridin-2-ylethynyl]pyridin-2-yl}-N,N-bis-cyclopropylmethylethan-1,2-diamine |
| 47.1 | 4-{4-[5-(4-chlorophenyl)pyridin-2-ylethynyl]phenyl}-1-cyclopropylmethylpiperidin-4-ol | including the tautomers, the diastereomers, the enantiomers, the mixtures thereof, and the salts thereof.

Thus, the first object of the present invention also includes alkyne compounds selected from the list comprising:

| No. | Name |
|---|---|
| 1.14 | 1-(2-{4-[5-(4-chlorophenyl)pyridin-2-ylethynyl]-2-methylphenoxy}ethyl)-4-isopropylpiperidin-4-ol |
| 1.15 | (1R,3R,5S)-8-(2-{4-[5-(4-chlorophenyl)pyridin-2-ylethynyl]-2-methylphenoxy}ethyl)-3-methyl-8-azabicyclo[3.2.1]octan-3-ol |
| 1.16 | (1R,3R,5S)-8-(2-{4-[5-(4-chlorophenyl)pyridin-2-ylethynyl]-2-methylphenoxy}ethyl)-3-ethyl-8-azabicyclo[3.2.1]octan-3-ol |
| 1.17 | (1R,3S,5S)-8-(2-{4-[5-(4-chlorophenyl)pyridin-2-ylethynyl]-2-methylphenoxy}ethyl)-3-trifluoromethyl-8-azabicyclo[3.2.1]octan-3-ol |
| 1.18 | (1R,3R,5S)-8-(2-{4-[5-(4-chlorophenyl)pyridin-2-ylethynyl]-2-methylphenoxy}ethyl)-3-trifluoromethyl-8-azabicyclo[3.2.1]octan-3-ol |
| 1.19 | 1-(2-{4-[5-(4-chlorophenyl)pyridin-2-ylethynyl]-2-methylphenoxy}ethyl)-4-ethylpiperidin-4-ol |
| 4.16 | 1-(2-{4-[5-(4-chlorophenyl)pyridin-2-ylethynyl]phenoxy}ethyl)-4-isopropylpiperidin-4-ol |
| 4.17 | 1-(2-{4-[5-(4-chlorophenyl)pyridin-2-ylethynyl]phenoxy}ethyl)-4-ethylpiperidin-4-ol |
| 48.1 | 1-(2-{4-[5-(4-chlorophenyl)pyrazin-2-ylethynyl]phenoxy}ethyl)-4-trifluoromethylpiperidin-4-ol |
| 48.2 | 1-(2-{4-[5-(4-chlorophenyl)pyrazin-2-ylethynyl]phenoxy}ethyl)-4-methylpiperidin-4-ol |
| 48.3 | 2-(4-chlorophenyl)-5-{4-[2-(4,4-dimethylpiperidin-1-yl)ethoxy]phenylethynyl}pyrazine |
| 48.4 | 2-(4-chlorophenyl)-5-{4-[2-(4-methylpiperidin-1-yl)ethoxy]phenylethynyl}pyrazine |
| 48.5 | (2-{4-[5-(4-chlorophenyl)pyrazin-2-ylethynyl]phenoxy}ethyl)cyclopentylamine |
| 48.6 | 1-(2-{4-[5-(2,4-dichlorophenyl)pyrazin-2-ylethynyl]phenoxy}ethyl)-4-methylpiperidin-4-ol |
| 48.7 | 1-(2-{4-[5-(4-chloro-2-methylphenyl)pyrazin-2-ylethynyl]phenoxy}ethyl)-4-methylpiperidin-4-ol |
| 49.1 | 3-fluoro-5-(4-methylcyclohex-1-enyl)-2-{4-[2-(4-methylpiperidin-1-yl)ethoxy]phenylethynyl}pyridine |
| 49.2 | 1-(2-{4-[3-fluoro-5-(4-methylcyclohex-1-enyl)pyridin-2-ylethynyl]phenoxy}ethyl)-4-methylpiperidin-4-ol |

-continued

| No. | Name |
|-----|------|
| 50.1 | (2-{4-[5-(4-chlorophenyl)pyridin-2-ylethynyl]phenyl}ethyl)cyclopentylamine |
| 50.2 | 1-(2-{4-[5-(4-chlorophenyl)pyridin-2-ylethynyl]phenyl}ethyl)-4-methylpiperidin-4-ol |
| 50.3 | 5-(4-chlorophenyl)-2-{4-[2-(4,4-dimethylpiperidin-1-yl)ethyl]phenylethynyl}pyridine |
| 50.4 | 5-(4-chlorophenyl)-2-{4-[2-(4-methylpiperidin-1-yl)ethyl]phenylethynyl}pyridine |
| 50.5 | 5-(4-chlorophenyl)-2-{3-methyl-4-[2-(4-methylpiperidin-1-yl)ethyl]phenylethynyl}pyridine |
| 51.1 | (5-{4-[5-(4-chlorophenyl)pyridin-2-yl]but-3-inyl}pyridin-2-yl)isopropylamine | including the tautomers, the diastereomers, the enantiomers, the mixtures thereof, and the salts thereof.

Thus, the invention also relates to the compounds in the form of the individual optical isomers, mixtures of the individual enantiomers or racemates, in the form of the tautomers and in the form of the free bases or corresponding acid addition salts with pharmacologically acceptable acids.

In a second aspect, the present invention relates to alkyne compounds selected from the list comprising:

| No. | Name |
|-----|------|
| 4.1 | [(S)-1-(2-{4-[5-(4-chlorophenyl)pyridin-2-ylethynyl]phenoxy}ethyl)pyrrolidin-2-yl]methanol |
| 7.1 | [(S)-1-(2-{4-[5-(4-chlorophenyl)-3-fluoropyridin-2-ylethynyl]phenoxy}ethyl)pyrrolidin-2-yl]methanol | and the salts thereof.

Thus, the invention also relates to the compounds in the form of the tautomers and in the form of the free bases or corresponding acid addition salts with pharmacologically acceptable acids.

The compounds according to the present invention, including the physiologically acceptable salts, are especially effective, compared with known, structurally similar compounds, as antagonists of the MCH receptor, particularly the MCH-1 receptor, and exhibit very good affinity in MCH receptor binding studies. In addition, the compounds according to the invention have a high to very high selectivity with regard to the MCH receptor. Generally the compounds according to the invention have low toxicity, they are well absorbed by oral route and have good intracerebral transitivity, particularly brain accessibility.

The subject of the invention also includes the compounds according to the invention, including their salts, wherein one or more hydrogen atoms are replaced by deuterium.

This invention also includes the physiologically acceptable salts of the alkyne compounds according to the invention as described above and hereinafter.

Also covered by this invention are compositions containing at least one alkyne compound according to the invention and/or a salt according to the invention optionally together with one or more physiologically acceptable excipients.

Also covered by this invention are pharmaceutical compositions containing at least one alkyne compound according to the invention and/or a salt according to the invention optionally together with one or more inert carriers and/or diluents.

This invention also relates to the use of at least one alkyne compound according to the invention and/or a salt according to the invention for influencing the eating behavior of a mammal.

The invention further relates to the use of at least one alkyne compound according to the invention and/or a salt according to the invention for reducing the body weight and/or for preventing an increase in the body weight of a mammal.

The invention also relates to the use of at least one alkyne compound according to the invention and/or a salt according to the invention for preparing a pharmaceutical composition with an MCH receptor-antagonistic activity, particularly with an MCH-1 receptor-antagonistic activity.

This invention also relates to the use of at least one alkyne compound according to the invention and/or a salt according to the invention for preparing a pharmaceutical composition which is suitable for the prevention and/or treatment of symptoms and/or diseases which are caused by MCH or are otherwise causally connected with MCH.

A further object of this invention is the use of at least one alkyne compound according to the invention and/or a salt according to the invention for preparing a pharmaceutical composition which is suitable for the prevention and/or treatment of metabolic disorders and/or eating disorders, particularly obesity, bulimia, bulimia nervosa, cachexia, anorexia, anorexia nervosa, and hyperphagia.

The invention also relates to the use of at least one alkyne compound according to the invention and/or a salt according to the invention for preparing a pharmaceutical composition which is suitable for the prevention and/or treatment of diseases and/or disorders associated with obesity, particularly diabetes, especially type II diabetes, complications of diabetes including diabetic retinopathy, diabetic neuropathy, diabetic nephropathy, insulin resistance, pathological glucose tolerance, encephalorrhagia, cardiac insufficiency, cardiovascular diseases, particularly arteriosclerosis and high blood pressure, arthritis, and gonitis.

In addition, the present invention relates to the use of at least one alkyne compound according to the invention and/or a salt according to the invention for preparing a pharmaceutical composition which is suitable for the prevention and/or treatment of hyperlipidemia, cellulitis, fat accumulation, malignant mastocytosis, systemic mastocytosis, emotional disorders, affective disorders, depression, anxiety, sleep disorders, reproductive disorders, sexual disorders, memory disorders, epilepsy, forms of dementia, and hormonal disorders.

The invention also relates to the use of at least one alkyne compound according to the invention and/or a salt according to the invention for preparing a pharmaceutical composition which is suitable for the prevention and/or treatment of urinary problems, such as, for example, urinary incontinence, overactive bladder, urgency, nycturia, and enuresis.

The invention further relates to the use of at least one alkyne compound according to the invention and/or a salt according to the invention for preparing a pharmaceutical composition which is suitable for the prevention and/or treatment of dependencies and/or withdrawal symptoms.

The invention further relates to processes for preparing for preparing a pharmaceutical composition according to the invention, characterized in that at least one alkyne compound according to the invention and/or a salt according to the invention is incorporated in one or more inert carriers and/or diluents by a non-chemical method.

The invention also relates to a pharmaceutical composition containing a first active substance which is selected from the alkyne compounds according to the invention and/or the corresponding salts as well as a second active substance which is selected from the group consisting of active substances for the treatment of diabetes, active substances for the treatment of diabetic complications, active substances for the treatment of obesity, preferably other than MCH antagonists, active substances for the treatment of high blood pressure, active substances for the treatment of dyslipidemia or hyperlipidemia, including arteriosclerosis, active substances for the treatment of arthritis, active substances for the treatment of anxiety states and active substances for the treatment of depression, optionally together with one or more inert carriers and/or diluents.

The starting materials and intermediate products used in the synthesis according to the invention and the actual methods of synthesis described are also a subject of this invention.

DETAILED DESCRIPTION OF THE INVENTION

An H atom bound to an N atom (imino or amino group) may in each case be replaced by a group which can be cleaved in vivo. By a group which can be cleaved in vivo from an N atom is meant, for example, a hydroxy group, an acyl group such as the benzoyl or pyridinoyl group, or a $C_{1-16}$-alkanoyl group such as the formyl, acetyl, propionyl, butanoyl, pentanoyl, or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert-butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl, or hexadecyloxycarbonyl group, a phenyl-$C_{1-6}$-alkoxycarbonyl group such as the benzyloxycarbonyl, phenylethoxycarbonyl, or phenylpropoxycarbonyl group, a $C_{1-3}$-alkylsulfonyl-$C_{2-4}$-alkoxycarbonyl, $C_{1-3}$-alkoxy-$C_{2-4}$-alkoxy-$C_{2-4}$-alkoxycarbonyl, or $R_e$CO—O—($R_fCR_g$)—O—CO— group wherein
  $R_e$ denotes a $C_{1-8}$-alkyl, $C_{5-7}$-cycloalkyl, phenyl, or phenyl-$C_{1-3}$-alkyl group,
  $R_f$ denotes a hydrogen atom, a $C_{1-3}$-alkyl, $C_{5-7}$-cycloalkyl, or phenyl group, and
  $R_g$ denotes a hydrogen atom, a $C_{1-3}$-alkyl or $R_e$CO—O—($R_fCR_g$)—O— group wherein $R_e$ to $R_g$ are as hereinbefore defined, while the phthalimido group is an additional possibility for an amino group, and the abovementioned ester groups may also be used as a group which can be converted in vivo into a carboxy group.

The compounds of general formula I according to the invention may have basic groups such as e.g., amino functions. Compounds according to the invention may therefore be present as internal salts, as salts with pharmaceutically useable inorganic acids such as hydrochloric acid, sulfuric acid, phosphoric acid, sulfonic acid, or organic acids (such as, for example, maleic acid, fumaric acid, citric acid, tartaric acid, or acetic acid).

The compounds according to the invention may be obtained using methods of synthesis which are known in principle. Preferably the compounds are obtained analogously to the methods of preparation explained more fully in the experimental section.

Stereoisomeric compounds according to the present invention may chiefly be separated by conventional methods. The diastereomers are separated on the basis of their different physico-chemical properties, e.g., by fractional crystallization from suitable solvents, by high pressure liquid or column chromatography, using chiral or preferably non-chiral stationary phases. Racemates may be separated, for example, by HPLC on suitable chiral stationary phases (e.g., Chiral AGP, CHIRALPAK® AD). Racemates which contain a basic or acidic function can also be separated via the diastereomeric, optically active salts which are produced on reacting with an optically active acid, for example, (+) or (−)-tartaric acid, (+) or (−)-diacetyl tartaric acid, (+) or (−)-monomethyl tartrate, or (+)-camphorsulfonic acid, or an optically active base, for example, with (R)-(+)-1-phenylethylamine, (S)-(−)-1-phenylethylamine, or (S)-brucine.

According to a conventional method of separating isomers, the racemate of a compound according to the invention is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol, or mixtures thereof, for example, in a ratio by volume of 50:50, are used. Then each of the optically active salts is dissolved in water, carefully neutralized with a base such as sodium carbonate or potassium carbonate, or with a suitable acid, e.g., with dilute hydrochloric acid or aqueous methanesulfonic acid and in this way the corresponding free compound is obtained in the (+) or (−) form.

The (R) or (S) enantiomer alone or a mixture of two optically active diastereomeric compounds according to the invention may also be obtained by performing the syntheses described above with a suitable reaction component in the (R) or (S) configuration.

As already mentioned, the compounds of formula (I) may be converted into the salts thereof, particularly for pharmaceutical use into the physiologically and pharmacologically acceptable salts thereof. These salts may be present on the one hand as physiologically and pharmacologically acceptable acid addition salts of the compounds of formula (I) with inorganic or organic acids. The acid addition salts may be prepared, for example, using hydrochloric acid, hydrobromic acid, sulfuric acid, phosphoric acid, methanesulfonic acid, ethanesulfonic acid, toluenesulfonic acid, benzenesulfonic acid, acetic acid, fumaric acid, succinic acid, lactic acid, citric acid, tartaric acid, or maleic acid. Moreover, mixtures of the above mentioned acids may be used.

The compounds according to the present invention, including the physiologically acceptable salts, are effective as antagonists of the MCH receptor, particularly the MCH-1 receptor, and exhibit good affinity in MCH receptor binding studies. Pharmacological test systems for MCH-antagonistic properties are described in the following experimental section.

As antagonists of the MCH receptor the compounds according to the invention are advantageously suitable as pharmaceutical active substances for the prevention and/or treatment of symptoms and/or diseases caused by MCH or causally connected with MCH in some other way. Generally the compounds according to the invention have low toxicity, they are well absorbed by oral route and have good intracerebral transitivity, particularly brain accessibility.

Therefore, MCH antagonists which contain at least one compound according to the invention are particularly suitable in mammals, such as, for example, rats, mice, guinea pigs, hares, dogs, cats, sheep, horses, pigs, cattle, monkeys, and humans, for the treatment and/or prevention of symptoms and/or diseases which are caused by MCH or are otherwise causally connected with MCH.

Diseases caused by MCH or otherwise causally connected with MCH are particularly metabolic disorders, such as for example obesity, and eating disorders, such as for example bulimia, including bulimia nervosa. The indication obesity includes in particular exogenic obesity, hyperinsulinemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity. This range of indications also includes cachexia, anorexia, and hyperphagia.

Compounds according to the invention may be particularly suitable for reducing hunger, curbing appetite, controlling eating behavior and/or inducing a feeling of satiation.

In addition, the diseases caused by MCH or otherwise causally connected with MCH also include hyperlipidemia, cellulitis, fatty accumulation, malignant mastocytosis, systemic mastocytosis, emotional disorders, affectivity disorders, depression, anxiety states, reproductive disorders, sexual disorders, memory disorders, epilepsy, forms of dementia, and hormonal disorders.

Compounds according to the invention are also suitable as active substances for the prevention and/or treatment of other illnesses and/or disorders, particularly those which accompany obesity, such as for example diabetes, diabetes mellitus, particularly type II diabetes, hyperglycemia, particularly chronic hyperglycemia, complications of diabetes including diabetic retinopathy, diabetic neuropathy, diabetic nephropathy, etc., insulin resistance, pathological glucose tolerance, encephalorrhagia, cardiac insufficiency, cardiovascular diseases, particularly arteriosclerosis and high blood pressure, arthritis, and gonitis.

MCH antagonists and formulations according to the invention may advantageously be used in combination with a dietary therapy, such as for example a dietary diabetes treatment, and exercise.

Another range of indications for which the compounds according to the invention are advantageously suitable is the prevention and/or treatment of micturition disorders, such as for example urinary incontinence, hyperactive bladder, urgency, nycturia, and enuresis, while the hyperactive bladder and urgency may or may not be connected with benign prostatic hyperplasia.

Generally speaking, the compounds according to the invention are potentially suitable for preventing and/or treating dependencies, such as, for example, alcohol and/or nicotine dependency, and/or withdrawal symptoms, such as, for example, weight gain in smokers coming off nicotine. By "dependency" is generally meant here an irresistible urge to take an addictive substance and/or to perform certain actions, particularly in order to either achieve a feeling of wellbeing or to eliminate negative emotions. In particular, the term "dependency" is used here to denote a dependency on an addictive substance. By "withdrawal symptoms" are meant here, in general, symptoms which occur or may occur when addictive substances are withdrawn from patients dependent on one or more such substances. The compounds according to the invention are potentially suitable particularly as active substances for reducing or ending tobacco consumption, for the treatment or prevention of a nicotine dependency and/or for the treatment or prevention of nicotine withdrawal symptoms, for reducing the craving for tobacco and/or nicotine and generally as an anti-smoking agent. The compounds according to the invention may also be useful for preventing or at least reducing the weight gain typically seen when smokers are coming off nicotine. The substances may also be suitable as active substances which prevent or at least reduce the craving for and/or relapse into a dependency on addictive substances. The term addictive substances refers particularly but not exclusively to substances with a psycho-motor activity, such as narcotics or drugs, particularly alcohol, nicotine, cocaine, amphetamine, opiates, benzodiazepines, and barbiturates.

The dosage required to achieve such an effect is conveniently, by intravenous or subcutaneous route, 0.001 to 30 mg/kg of body weight, preferably 0.01 to 5 mg/kg of body weight, and by oral or nasal route or by inhalation, 0.01 to 50 mg/kg of body weight, preferably 0.1 to 30 mg/kg of body weight, in each case 1 to 3× daily.

For this purpose, the compounds prepared according to the invention may be formulated, optionally in conjunction with other active substances as described hereinafter, together with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose, or fatty substances such as hard fat or suitable mixtures thereof, to produce conventional galenic preparations such as plain or coated tablets, capsules, lozenges, powders, granules, solutions, emulsions, syrups, aerosols for inhalation, ointments, or suppositories.

In addition to pharmaceutical compositions, the invention also includes compositions containing at least one alkyne compound according to the invention and/or a salt according to the invention optionally together with one or more physiologically acceptable excipients. Such compositions may also be, for example, foodstuffs which may be solid or liquid, in which the compound according to the invention is incorporated.

For the abovementioned combinations it is possible to use as additional active substances particularly those which for example potentiate the therapeutic effect of an MCH antagonist according to the invention in terms of one of the indications mentioned above and/or which make it possible to reduce the dosage of an MCH antagonist according to the invention. Preferably one or more additional active substances are selected from among active substances for the treatment of diabetes, active substances for the treatment of diabetic complications, active substances for the treatment of obesity, preferably other than MCH antagonists, active substances for the treatment of high blood pressure, active substances for the treatment of hyperlipidemia, including arteriosclerosis, active substances for the treatment of dyslipidemia, including arteriosclerosis, active substances for the treatment of arthritis, active substances for the treatment of anxiety states, and active substances for the treatment of depression.

The abovementioned categories of active substances will now be explained in more detail by means of examples.

Examples of active substances for the treatment of diabetes are insulin sensitizers, insulin secretion accelerators, biguanides, insulins, α-glucosidase inhibitors, and $\beta_3$ adrenoreceptor agonists. Insulin sensitizers include glitazones, particularly pioglitazone and its salts (preferably hydrochloride), troglitazone, rosiglitazone and its salts (preferably maleate), JTT-501, GI-262570, MCC-555, YM-440, DRF-2593, BM-13-1258, KRP-297, R-119702, and GW-1929. Insulin secretion accelerators include sulfonylureas, such as, for example, tolbutamide, chloropropamide, tolazamide, acetohexamide, glyclopyramide and its ammonium salts, glibenclamide, gliclazide, and glimepiride. Further examples of insulin secretion accelerators are repaglinide, nateglinide, mitiglinide (KAD-1229), and JTT-608. Biguanides include metformin, buformin, and phenformin. Insulins include those obtained from animals, particularly cattle or pigs, semisynthetic human insulins which are synthesized enzymatically from insulin obtained from animals, human insulin obtained by genetic engineering, e.g., from *Escherichia coli* or yeasts. Moreover, the term insulin also includes insulin-zinc (containing 0.45 to 0.9 percent by weight of zinc) and protamine-insulin-zinc obtainable from zinc chloride, protamine sulfate, and insulin. Insulin may also be obtained from insulin fragments or derivatives (for example INS-1, etc.). Insulin may also include different kinds, e.g., with regard to the onset time and duration of effect ("ultra immediate action type", "immediate action type", "two phase type", "intermediate type", "prolonged action type", etc.), which are selected depending on the pathological condition of the patient. α-Glucosidase inhibitors include acarbose, voglibose, miglitol, and emiglitate. $\beta_3$ Adrenoreceptor agonists include AJ-9677, BMS-196085, SB-226552, and AZ40140. Active substances for the treatment of diabetes other than those mentioned above include ergoset, pramlintide, leptin, and BAY-27-9955 as well as glycogen phosphorylase inhibitors, sorbitol dehydrogenase inhibitors, protein tyrosine phosphatase 1B inhibitors, dipeptidyl protease inhibitors, glipazide, and glyburide.

Active substances for the treatment of diabetic complications include, for example, aldose reductase inhibitors, glycation inhibitors and protein kinase C inhibitors, DPP-IV blockers, GLP-1 or GLP-2 analogues, and SGLT-2 inhibitors. Aldose reductase inhibitors are, for example, tolrestat, epalrestat, imirestat, zenarestat, SNK-860, zopolrestat, ARI-50i, AS-3201. An example of a glycation inhibitor is pimagedine. Protein Kinase C inhibitors are for example NGF, and LY-333531. DPP-IV blockers are, for example, LAF237 (Novartis), MK431 (Merck), as well as 815541, 823093, and 825964 (all GlaxoSmithKline). GLP-1 analogues are, for example, Liraglutide (NN2211) (Novo Nordisk), CJC-1131 (Conjuchem), and Exenatide (Amylin). SGLT-2 inhibitors are, for example, AVE-2268 (Aventis) and T-1095 (Tanabe, Johnson & Johnson). Active substances other than those mentioned above for the treatment of diabetic complications include alprostadil, thiapride hydrochloride, cilostazol, mexiletine hydrochloride, ethyl eicosapentate, memantine, and pimagedine (ALT-711).

Active substances for the treatment of obesity, preferably other than MCH antagonists, include lipase inhibitors and anorectics. A preferred example of a lipase inhibitor is orlistat. Examples of preferred anorectics are phentermine, mazindol, fluoxetine, sibutramine, baiamine, (S)-sibutramine, SR-141716, and NGD-95-1. Active substances other than those mentioned above for the treatment of obesity include lipstatin.

Moreover, for the purposes of this application, the active substance group of anti-obesity active substances also includes the anorectics, of which the $\beta_3$ agonists, thyromimetic active substances and NPY antagonists should be emphasized. The range of substances which may be considered as preferred anti-obesity or anorectic active substances is indicated by the following additional list, by way of example: phenylpropanolamine, ephedrine, pseudoephedrine, phentermine, a cholecystokinin-A (hereinafter referred to as CCK-A) agonist, a monoamine reuptake inhibitor (such as, for example, sibutramine), a sympathomimetic active substance, a serotonergic active substance (such as, for example, dexfenfluramine, fenfluramine, a 5-HT2C agonist such as BVT.933 or APD356, or duloxetine), a dopamine antagonist (such as, for example, bromocriptine or pramipexole), a melanocyte-stimulating hormone receptor agonist or mimetic, an analogue of melanocyte-stimulating hormone, a cannabinoid receptor antagonist (ACOMPLIA® (rimonabant)), an MCH antagonist, the OB protein (hereinafter referred to as leptin), a leptin analogue, a fatty acid synthase (FAS) antagonist, a leptin receptor agonist, a galanine antagonist, and a GI lipase inhibitor or reducer (such as, for example, orlistat). Other anorectics include bombesin agonists, dehydroepiandrosterone or its analogues, glucocorticoid receptor agonists and antagonists, orexin receptor antagonists, urocortin binding protein antagonists, agonists of the Glucagon-like Peptide-1 receptor, such as, for example, exendin, AC 2993, CJC-131, IP10, or GRT0203Y, DPP-IV inhibitors and ciliary neurotrophic factors, such as, for example, axokines. In this context mention should also be made of the forms of therapy which produce weight loss by increasing the fatty acid oxidation in the peripheral tissue, such as, for example, inhibitors of acetylcoA carboxylase.

Active substances for the treatment of high blood pressure include inhibitors of angiotensin converting enzyme, calcium antagonists, potassium channel openers, and angiotensin II antagonists. Inhibitors of angiotensin converting enzyme include captopril, enalapril, alacepril, delapril (hydrochloride), lisinopril, imidapril, benazepril, cilazapril, temocapril, trandolapril, and manidipine (hydrochloride). Examples of calcium antagonists are nifedipine, amlodipine, efonidipine, and nicardipine. Potassium channel openers include levcromakalim, L-27152, AL0671, and NIP-121. Angiotensin II antagonists include telmisartan, losartan, candesartan cilexetil, valsartan, irbesartan, CS-866, and E4177.

Active substances for the treatment of hyperlipidemia, including arteriosclerosis, include HMG-CoA reductase inhibitors and fibrate compounds. HMG-CoA reductase inhibitors include pravastatin, simvastatin, lovastatin, atorvastatin, fluvastatin, lipantil, cerivastatin, itavastatin, ZD-4522 and their salts. Fibrate compounds include bezafibrate, clinofibrate, clofibrate, and simfibrate.

Active substances for the treatment of dyslipidemia, including arteriosclerosis, include, e.g., medicaments which raise the HDL level, such as, e.g., nicotinic acid and derivatives and preparations thereof, such as, e.g., niaspan, as well as agonists of the nicotinic acid receptor.

Active substances for the treatment of arthritis include NSAIDs (non-steroidal anti-inflammatory drugs), particularly COX-2 inhibitors, such as, for example, meloxicam or ibuprofen.

Active substances for the treatment of anxiety states include chlordiazepoxide, diazepam, oxozolam, medazepam, cloxazolam, bromazepam, lorazepam, alprazolam, and fludiazepam.

Active substances for the treatment of depression include fluoxetine, fluvoxamine, imipramine, paroxetine, and sertraline.

The dosage for these active substances is conveniently ⅕ of the lowest normal recommended dose up to ⅓ of the normal recommended dose.

In another embodiment the invention also relates to the use of at least one alkyne compound according to the invention and/or a salt according to the invention for influencing the eating behavior of a mammal. This use is particularly based on the fact that compounds according to the invention may be suitable for reducing hunger, curbing appetite, controlling eating behavior and/or inducing a feeling of satiety. The eating behavior is advantageously influenced so as to reduce food intake. Therefore, the compounds according to the invention are advantageously used for reducing body weight. Another use according to the invention is the prevention of increases in body weight, for example in people who had previously taken steps to lose weight and are interested in maintaining their lower body weight. According to this embodiment it is preferably a non-therapeutic use. Such a non-therapeutic use might be a cosmetic use, for example to alter the external appearance, or an application to improve general health. The compounds according to the invention are preferably used non-therapeutically for mammals, particularly humans, not suffering from any diagnosed eating disorders, no diagnosed obesity, bulimia, diabetes and/or no diagnosed micturition disorders, particularly urinary incontinence. Preferably, the compounds according to the invention are suitable for non-therapeutic use in people whose BMI (body mass index), defined as their body weight in kilograms divided by their height (in meters) squared, is below a level of 30, particularly below 25.

The Examples that follow are intended to illustrate the invention.

Preliminary Remarks

As a rule, IR, $^1$H-NMR and/or mass spectra have been obtained for the compounds prepared. Unless otherwise stated the $R_f$-values were determined using ready-made silica gel 60 TLC plates $F_{254}$ (E. Merck, Darmstadt, Item No. 1.05714) without chamber saturation. The $R_f$-values obtained under the heading Alox were determined using ready-made aluminum oxide 60 TLC plates $F_{254}$ (E. Merck, Darmstadt, Item No. 1.05713) without chamber saturation. The ratios specified for the eluants are based on units by volume of the solvents in question. The units by volume specified in the case of $NH_3$ relate to a concentrated solution of $NH_3$ in water. For chromatographic purification, silica gel made by Messrs Millipore (MATREX™, 35-70 my) is used. For chromatographic purification, Alox (E. Merck, Darmstadt, standardized aluminum oxide 90, 63-200 μm, Item no.: 1.01097.9050) is used. The HPLC data specified were measured under the parameters indicated below.

Analytical Columns:
Zorbax column (Agilent Technologies), SB (Stable Bond)—C18; 3.5 μm; 4.6×75 mm; column temperature: 30° C.; flow: 0.8 mL/min; injection volume: 5 μL; detection at 254 nm (methods A, B and C).
Zorbax column (Agilent Technologies), Bonus-RP-C14; 3.5 μm; 4.6×75 mm; column temperature: 30° C.; flow: 0.8 mL/min; injection volume: 5 μL; detection at 254 nm (methods D, E and F).
Method A: water:acetonitrile:formic acid 9:1:0.01 towards 1:9:0.01 over 9 minutes
Method B: water:acetonitrile:formic acid 9:1:0.01 towards 1:9:0.01 over 4 minutes, then 6 minutes 1:9:0.01
Method C: water:acetonitrile:formic acid 9:1:0.01 towards 4:6:0.01 over 8 minutes
Method D: water:acetonitrile:formic acid 9:1:0.01 towards 1:9:0.01 over 9 minutes
Method E: water:acetonitrile:formic acid 9:1:0.01 towards 1:9:0.01 over 4 minutes, then 6 minutes 1:9:0.01
Method F: water:acetonitrile:formic acid 9:1:0.01 towards 4:6:0.01 over 8 minutes
Method G: water:acetonitrile:formic acid 9.5:0.5:0.01 towards 1:9:0.01 over 9 minutes
Method H: water:acetonitrile:formic acid 9.5:0.5:0.01 towards 1:9:0.01 over 4 minutes and then 6 minutes at this gradient Preparative Columns:
Zorbax column (Agilent Technologies), SB (Stable Bond)—C18; 3.5 μm; 30×100 mm; column temperature: ambient temperature; flow: 30 mL/min; detection at 254 nm.
Zorbax column (Agilent Technologies), Bonus—C14; 3.5 μm; 30×100 mm; column temperature: ambient temperature; flow: 30 mL/min; detection at 254 nm.
Waters Symmetry C18, 3.5 μm; 30×100 mm; column temperature: ambient temperature; flow: 30 mL/min; detection at 254 nm.

In preparative HPLC purification, as a rule the same gradients are used which were used when obtaining the analytical HPLC data. The products are collected under mass control, the fractions containing the product are combined and freeze-dried.

Temperatures are given in degrees Celsius (° C.); times are generally given in minutes (min), hours (h), or days (d). If there is no specific information as to the configuration, it is not clear whether there are pure enantiomers or whether partial or even total racemization has taken place.

The following abbreviations are used above and hereinafter:

| | |
|---|---|
| CDI | carbonyldiimidazole |
| cyc | cyclohexane |
| DCM | dichloromethane |
| DIPE | diisopropylether |
| DMF | dimethylformamide |
| dppf | 1,1'-bis(diphenylphosphino)ferrocene |
| EtOAc | ethyl acetate |
| EtOH | ethanol |
| MeOH | methanol |
| MTBE | methyl-tert-butylether |
| New-DAST | (bis-(2-methoxyethyl)amino)sulfur trifluoride (50% in toluene) |
| PE | petroleum ether |
| PPh$_3$ | triphenylphosphane |
| RT | ambient (room) temperature (approx. 20° C.) |
| TBAF | tetrabutylammonium fluoride trihydrate |
| TFA | trifluoroacetic acid |
| THF | tetrahydrofuran |
| →* | denotes the binding site of a group |

Synthesis of the Intermediate Products

Intermediate Product 1

4-trifluoromethylpiperidin-4-ol

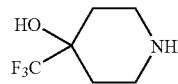

IP 1a. 1-benzyl-4-trifluoromethylpiperidin-4-ol 0.38 g (151.90 mmol) of cesium fluoride was added to a solution of 4.63 mL (25.00 mmol) 1-benzylpiperazine-4-one in 100 mL of THF, the mixture was cooled to −5° C., 12.50 mL (142.20 mmol) trimethyltrifluoromethylsilane (2.5 M in THF) was slowly added, and the mixture was stirred for 1.5 hours at −5° C. Another 6.25 mL (71.1 mmol) of trimethyltrifluoromethylsilane was added and the mixture was stirred for 1 hour at 20° C. 100 mL of IN aqueous HCl was added and the mixture was stirred for 1 hour. The reaction mixture was made alkaline by the addition of saturated aqueous potassium carbonate solution and the phases were separated. The organic phase was dried over sodium sulfate and evaporated down in vacuo. The crude product was used in the next reaction step without further purification. Yield: 6.48 g (quant.

yield); C$_{13}$H$_{16}$F$_3$NO (M=259.267); calc.: molpeak (M+H)$^+$: 260; found: molpeak (M+H)$^+$: 260; HPLC-MS: 4.15 minutes (method A).

IP 1b. 4-trifluoromethylpiperidin-4-ol

A suspension of 6.48 g (25.00 mmol) of 1-benzyl-4-trifluoromethylpiperidin-4-ol and 810 mg Pd/C (10%) in 100 mL of MeOH was hydrogenated at RT and 3 bar hydrogen pressure for 17 hours. The catalyst was filtered off and the filtrate evaporated down in vacuo. Yield: 4.22 g (quant. yield); C$_6$H$_{10}$F$_3$NO (M=169.145); calc.: molpeak (M+H)$^+$: 170; found: molpeak (M+H)$^+$: 17; R$_f$ value: 0.00 (silica gel, cyc/EtOAc 2:1).

Intermediate Product 2

2,2,2-trifluoro-1-piperidin-4-ylethanol

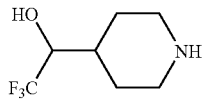

IP 2a. benzyl 4-(2,2,2-trifluoro-1-hydroxyethyl)piperidine-1-carboxylate

The product was obtained analogously to IP 1a starting from 7.42 g (30.00 mmol) of benzyl 4-formylpiperidine-1-carboxylate. The crude product was purified by means of column chromatography (silica gel, cyc/EtOAc 4:1). Yield: 4.15 g (44% of theoretical); C$_{15}$H$_{18}$F$_3$NO3 (M=317.304); calc.: molpeak (M+H)$^+$: 318; found: molpeak (M+H)$^+$: 318; HPLC-MS: 8.33 minutes (method A).

IP 2b. 2,2,2-trifluoro-1-piperidin-4-ylethanol

A suspension of 3.11 g (9.80 mmol) of benzyl 4-(2,2,2-trifluoro-1-hydroxyethyl)piperidine-1-carboxylate and 300 mg Pd/C (10%) in 30 mL of MeOH was hydrogenated at RT and 3 bar hydrogen pressure for 4 hours. The catalyst was filtered off and the filtrate was evaporated down in vacuo. Yield: 1.82 g (quant. yield); C$_7$H$_{12}$F$_3$NO (M=183.172); calc.: molpeak (M+H)$^+$: 184; found: molpeak (M+H)$^+$: 184; R$_f$ value: 0.20 (silica gel, EtOAc/MeOH/conc. aqueous ammonia 5:5:0.5).

Intermediate Product 3

2,2,2-trifluoro-1-piperidin-4-ylethanone

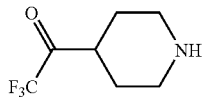

IP 3a. benzyl 4-(2,2,2-trifluoroacetyl)piperidine-1-carboxylate

A mixture of 1.00 g (83.15 mmol) of benzyl 4-(2,2,2-trifluoro-1-hydroxyethyl)piperidine-1-carboxylate and 4.95 g (11.66 mmol) Dess-Martin periodinane in 30 mL of DCM was stirred for 20 hours at RT and then made alkaline with saturated aqueous potassium carbonate solution. The reaction mixture was filtered and the phases of the filtrate were separated. The organic phase was dried over sodium sulfate and evaporated down in vacuo. Yield: 896 mg (90% of theoretical); C$_{15}$H$_{16}$F$_3$NO$_3$ (M=315.288); calc.: molpeak (M−H)$^-$: 314; found: molpeak (M−H)$^-$: 314; R$_f$ value: 0.39 (silica gel, cyc/EtOAc 2: 1).

IP 3b. 2,2,2-trifluoro-1-piperidin-4-ylethanone

The product was obtained analogously to IP 2b starting from 900 mg (2.85 mmol) of benzyl 4-(2,2,2-trifluoroacetyl)piperidine-1-carboxylate. Yield: 516 mg (quant. yield); C$_7$H$_{10}$F$_3$NO (M=181.156); calc.: molpeak (M+H)$^+$: 182; found: molpeak (M+H)$^+$: 182; R$_f$ value: 0.18 (silica gel, EtOAc/MeOH/conc. aqueous ammonia 5:5:0.5).

Intermediate Product 4 piperidin-4-on-O-methyloxime

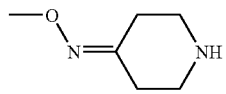

A mixture of 3.84 g (25.00 mmol) 4-piperdinone hydrochloride and 2.51 g (30.00 mmol) O-methylhydroxylamine hydrochloride in 50 mL of MeOH was stirred for 8 hours at 60° C. and then evaporated down in vacuo. The residue was stirred with saturated aqueous potassium carbonate solution and the aqueous phase was extracted with DCM. The combined organic phases were dried over sodium sulfate, evaporated down in vacuo, and dried. Yield: 2.80 g (87% of theoretical); C$_6$H$_{12}$N$_2$O (M=128.172); calc.: molpeak (M+H)$^+$: 129; found: molpeak (M+H)$^+$: 129; HPLC-MS: 1.44 minutes (method C).

Intermediate Product 5

(3S,4R)-4-trifluoromethylpiperidin-3,4-diol

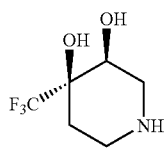

IP 5a. 1-benzyl-4-trifluoromethylpyridinium chloride

A solution of 7.59 mL (65.94 mmol) benzyl chloride in 10 mL of acetonitrile was added to a solution of 10.00 g (65.94 mmol) of 4-trifluoromethylpyridine in 40 mL of acetonitrile and the mixture was stirred for 2 hours at 80° C. Another 1.5 mL of benzyl chloride was added and the mixture was stirred for 22 hours at 80° C. The reaction mixture was cooled to RT and combined with MTBE. The precipitate was filtered off, washed with MTBE, dried in vacuo, and stored in the desiccator. Yield: 14.48 g (80% of theoretical); C$_{13}$H11F$_3$N.Cl (M=273.681); calc.: molpeak (M+H)$^+$: 238; found: molpeak (M+H)$^+$: 238.

IP 5b. 1-benzyl-4-trifluoromethyl-1,2,3,6-tetrahydropyridine 3.00 g (79.36 mmol) of sodium borohydride was added batchwise to a solution of 14.48 g (52.91 mmol) of 1-benzyl-4-trifluoromethylpyridinium chloride in 100 mL of EtOH with strong cooling at 0° C., then the cooling was stopped and the reaction mixture was stirred for 1.5 hours at 14° C. While cooling, 50 mL of water and then 50 mL of EtOH were added within 30 minutes. The reaction mixture was stirred for another 30 minutes, the resulting suspension was filtered and the filtrate was evaporated down in vacuo. Yield: 11.72 g (92% of theoretical); $C_{13}H_{14}F_3N$ (M=241.252); calc.: molpeak $(M+H)^+$: 242; found: molpeak $(M+H)^+$: 242; HPLC-MS: 3.60 minutes (method B).

IP 5c. (3S,4R)-1-benzyl-4-trifluoromethylpiperidin-3,4-diol 43.80 g of AD-Mix-Beta was placed in 3000 mL of tert-butanol/water (1:1) and stirred for 20 minutes at RT. The mixture was cooled to 0° C., 2.97 g (31.25 mmol) of methanesulfonamide and 7.54 g (31.25 mmol) of 1-benzyl-4-trifluoromethyl-1,2,3,6-tetrahydropyridine were added, the cooling bath was removed, and the mixture was stirred for 8 days at RT. Another 22 g of AD-Mix-Beta and 1.5 g of methanesulfonamide were added and the mixture was again stirred for 7 days at RT. 11.2 g of sodium sulfite was added and the mixture was stirred for 1 hour. 200 mL of semisaturated aqueous sodium bicarbonate solution was added and the aqueous phase was exhaustively extracted with DCM. The combined organic phases were dried over sodium sulfate and evaporated down in vacuo. The crude product was purified by MPLC-MS (Grom-Sil 120 ODS 4, 10 μm, gradient 0.15% formic acid in water/acetonitrile 90:10→10:90 in 10 minutes). The eluates were combined, evaporated down in vacuo, and neutralized with 100 mL of semisaturated aqueous sodium bicarbonate solution. The aqueous phase was extracted with EtOAc, and the combined organic phases were dried over sodium sulfate and evaporated down in vacuo. Yield: 1.51 g (17% of theoretical); $C_{13}H_{16}F_3NO_2$ (M=275.267); calc.: molpeak $(M+H)^+$: 276; found: molpeak $(M+H)^+$: 276; $R_f$ value: 0.40 (silica gel, cyc/EtOAc 2:1).

IP 5d. (3S,4R)-4-trifluoromethylpiperidin-3,4-diol

A mixture of 1.50 g (5.45 mmol) of (3S,4R)-1-benzyl-4-trifluoromethylpiperidin-3,4-diol and 170 mg of Pd/C (10%) in 17 mL of MeOH was hydrogenated at RT and 3 bar hydrogen pressure for 5 hours. The catalyst was filtered off and the filtrate was evaporated down in vacuo. Yield: 910 mg (90% of theoretical); $C_6H_{10}F_3NO_2$ (M=185.144); calc.: molpeak $(M+H)^+$: 186; found: molpeak $(M+H)^+$: 186; $R_f$ value: 0.35 (silica gel, EtOAc/MeOH/conc. aqueous ammonia 7:3:0.3).

Intermediate Product 6

(3R,4S)-4-trifluoromethylpiperidin-3,4-diol

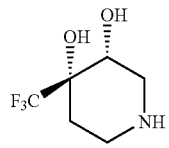

IP 6a. (3R,4S)-1-benzyl-4-trifluoromethylpiperidin-3,4-diol

The product was obtained analogously to IP 5c starting from IP 5b and AD-Mix-Alpha. The crude product was purified by HPLC-MS (Zorbax Bonus C18 amide-phase 5 μm, gradient 0.15% formic acid in water/acetonitrile 10/90→90/10 v/v). Yield: 1.09 g (16% of theoretical); $C_{13}H_{16}F_3NO_2$ (M=275.267); calc.: molpeak $(M+H)^+$: 276; found: molpeak $(M+H)^+$: 276; HPLC-MS: 3.70 minutes (method A).

IP 6b. (3R,4S)-4-trifluoromethylpiperidin-3,4-diol

The product was obtained analogously to intermediate product IP 5d starting from (3R,4S)-1-benzyl-4-trifluoromethylpiperidin-3,4-diol. Yield: 665 mg (91% of theoretical); $C_6H_{10}F_3NO_2$ (M=185.144); calc.: molpeak $(M+H)^+$: 186; found: molpeak $(M+H)^+$: 186; $R_f$ value: 0.35 (silica gel, EtOAc/MeOH/conc. aqueous ammonia 7:3:0.3).

Intermediate Product 7

(3R,4S)-4-methylpiperidin-3,4-diol

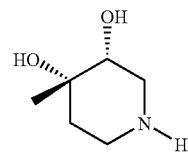

IP 7a. 1-benzyl-4-methyl-1,2,3,6-tetrahydropyridine

The product was obtained analogously to IP 5b starting from 10.0 g (45.5 mmol) of 1-benzyl-4-methylpyridinium chloride. Yield: 7.15 g (84% of theoretical); $C_{13}H_{17}N$ (M=187.281); calc.: molpeak $(M+H)^+$: 188; found: molpeak $(M+H)^+$: 188; $R_f$ value: 0.95 (silica gel, EtOAc/MeOH/NH$_3$ 9:1:0.1).

IP 7b. (3R,4S)-1-benzyl-4-methylpiperidin-3,4-diol 14 g of AD-Mix-Alpha in 50 mL of water and 50 mL of tert-butanol were placed under a nitrogen atmosphere and the mixture was stirred for 20 minutes at RT. Subsequently it was cooled to 0° C., 0.95 g (10.0 mmol) of methanesulfonic acid amide and 1.87 g (10.0 mmol) of 1-benzyl-4-methyl-1,2,3,6-tetrahydropyridine were added, the cooling bath was removed, and the reaction mixture was stirred for 24 hours at RT. 3.5 g of sodium sulfite was added to the reaction mixture which was stirred for 1 hour. 200 mL of DCM and 200 ML of saturated sodium bicarbonate solution were added, and the organic phase was separated off and extracted with 100 mL of KHSO$_4$ solution. The aqueous phase was made alkaline with saturated potassium carbonate solution, extracted with 200 mL EtOAc, and the organic phase was dried over sodium sulfate. After the desiccant and solvent had been eliminated, the crude product was purified by chromatography (silica gel, EtOAc/MeOH/NH$_3$ 19:1:0.1). Yield: 1.23 g (56% of theoretical); C$_{13}$H$_{19}$NO$_2$ (M=221.296); calc.: molpeak (M+H)$^+$: 222; found: molpeak (M+H)$^+$: 222; R$_f$ value: 0.56 (silica gel, EtOAc/MeOH/NH$_3$ 19:1:0.1).

IP 7c. (3R,4S)-4-methylpiperidin-3,4-diol

The product was obtained analogously to IP 5d starting from 1.23 g (5.57 mmol) of (3R,4S)-1-benzyl-4-methylpiperidin-3,4-diol. Yield: 730 mg (quant. yield); C$_6$H$_{13}$NO$_2$ (M=131.173); calc.: molpeak (M+H)$^+$: 132; found: molpeak (M+H)$^+$: 132; HPLC-MS: 0.93 minutes (method C).

Intermediate Product 8

(S)-1-pyrrolidin-2-ylcyclopropanol

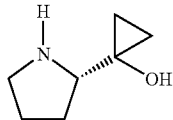

IP 8a. 1-((S)-1-benzylpyrrolidin-2-yl)cyclopropanol

First 6.91 mL (23.57 mmol) of titanium (IV) isopropoxide and then 14.3 mL (42.9 mmol, 3 M in diethyl ether) of ethylmagnesium bromide were slowly added dropwise to a solution of 5.0 g (21.43 mmol) of N-benzyl-L-proline ethyl ester in 80 mL of dry diethyl ether which had been cooled to −15° C. and the reaction mixture was stirred for 30 minutes at this temperature. Subsequently at approximately 10° C., 5.4 mL (42.9 mmol) of boron trifluoride-diethyl ether complex were added and the mixture was stirred for a further 75 hours at RT. While cooling, 50 mL of 1M NaOH was added, the mixture was stirred for 1 hours at RT, combined with 100 mL of diethyl ether, and the organic phase was separated off and dried over sodium sulfate. After the desiccant and solvent had been eliminated, the residue was purified by chromatography (silica gel, EtOAc). Yield: 0.745 g (16% of theoretical); C$_{14}$H$_{19}$NO (M=217.307); calc.: molpeak (M+H)$^+$: 218; found: molpeak (M+H)$^+$: 218; R$_f$ value: 0.17 (silica gel, EtOAc).

IP 8b. (S)-1-pyrrolidin-2-ylcyclopropanol

The product was obtained analogously to IP 5d starting from 745 mg (3.43 mmol) 1-((S)-1-benzylpyrrolidin-2-yl)cyclopropanol. Yield: 350 mg (80% of theoretical); C$_7$H$_{13}$NO (M=127.184); calc.: molpeak (M+H)$^+$: 128; found: molpeak (M+H)$^+$: 128; R$_f$ value: 0.10 (silica gel, EtOAc/MeOH/NH$_3$ 5:5:0.5).

Intermediate Product 9 endo-3-methyl-8-azabicyclo[3.2.1]octan-3-ol

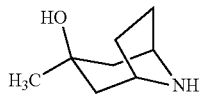

IP 9a. endo-8-benzyl-3-methyl-8-azabicyclo[3.2.1]octan-3-ol 16 mL (25.55 mmol) of MeLi (1.6 M in diethyl ether) was added to a solution of 5.00 g (23.22 mmol) of N-benzylnortropinone in 50 mL of THF under argon at −5° C. and the mixture was stirred for 2 hours at RT. Another 16 mL (25.55 mmol) of MeLi (1.6 M in diethyl ether) was added and the mixture was stirred for 16 hours at RT. The reaction mixture was combined with water while cooling with ice, the aqueous phase was extracted with EtOAc, the combined organic extracts were dried over sodium sulfate and evaporated down in vacuo. The crude product was purified by MPLC (Alox, DCM/EtOAc 9:1). Yield: 1.40 g (26% of theoretical); C$_{15}$H$_2$NO (M=231.333); calc.: molpeak (M+H)$^+$: 232; found: molpeak (M+H)$^+$: 232; R$_f$ value: 0.33 (Alox, DCM/EtOAc 85:15).

IP 9b. endo-3-methyl-8-azabicyclo[3.2.1]octan-3-ol

The product was obtained analogously to IP 5d starting from 8-benzyl-3-methyl-8-azabicyclo[3.2.1]octan-3-ol. Yield: 0.90 g (78% of theoretical); C$_8$H$_{15}$NO (M=141.211); calc.: molpeak (M+H)$^+$: 142; found: molpeak (M+H)$^+$: 142; R$_f$ value: 0.33 (Alox, DCM/EtOAc 5:1).

Intermediate Product 10 endo-3-ethyl-8-azabicyclo[3.2.1]octan-3-ol

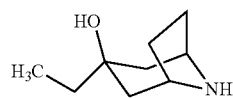

IP 10a. endo-8-benzyl-3-ethyl-8-azabicyclo[3.2.1]octan-3-ol 15.5 mL (46.45 mmol) of ethylmagnesium bromide (3M in diethyl ether) was added dropwise to a solution of 5.00 g (23.22 mmol) of N-benzylnortropinone in 50 mL of THF under argon and the mixture was stirred for 3 hours at 40° C. The reaction mixture was combined with water while cooling with ice, the aqueous phase was extracted with EtOAc, and the combined organic extracts were dried over sodium sulfate and evaporated down in vacuo. The crude product was purified by MPLC (Alox, DCM/EtOAc 9:1). Yield: 2.90 g (51% of theoretical); C$_{16}$H$_{23}$NO (M=245.360); calc.: molpeak (M+H)$^+$: 246; found: molpeak (M+H)$^+$: 246.

IP 10b. endo-3-ethyl-8-azabicyclo[3.2.1]octan-3-ol

The product was obtained analogously to IP 5d starting from 8-benzyl-3-ethyl-8-azabicyclo[3.2.1]octan-3-ol. Yield: 1.70 g (93% of theoretical); C$_9$H$_{17}$NO (M=155.237); calc.: molpeak (M+H)$^+$: 156; found: molpeak (M+H)$^+$: 156.

Intermediate Product 11 exo-3-trifluoromethyl-8-azabicyclo[3.2.1]octan-3-ol

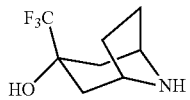

IP 11a. 8-benzyl-3-trifluoromethyl-8-azabicyclo[3.2.1]octan-3-ol

The product was obtained analogously to IP 10a starting from N-benzylnortropinone. The crude product was purified by column chromatography (silica gel, cyc/EtOAc 4:1). 2 fractions were obtained. Fraction 1: exo-8-benzyl-3-trifluoromethyl-8-azabicyclo[3.2.1]octan-3-ol: yield: 1.60 g (24% of theoretical); $C_{15}H_{18}F_3NO$ (M=285.305); calc.: molpeak (M+H)$^+$: 286; found: molpeak (M+H)$^+$: 286. Fraction 2: endo-8-benzyl-3-trifluoromethyl-8-azabicyclo[3.2.1]octan-3-ol: yield: 3.60 g (54% of theoretical); $C_{15}H_{18}F_3NO$ (M=285.305); calc.: molpeak (M+H)$^+$: 286; found: molpeak (M+H)$^+$: 286.

IP 11b. exo-3-trifluoromethyl-8-azabicyclo[3.2.1]octan-3-ol

The product was obtained analogously to IP 5d starting from exo-8-benzyl-3-trifluoromethyl-8-azabicyclo[3.2.1]octan-3-ol (IP 11a, fraction 1). Yield: 0.90 g (94% of theoretical); $C_8H_{12}F_3NO$ (M=195.182); calc.: molpeak (M+H)$^+$: 196; found: molpeak (M+H)$^+$: 196; HPLC-MS: 2.56 minutes (method C).

Intermediate Product 12 endo-3-trifluoromethyl-8-azabicyclo[3.2.1]octan-3-ol

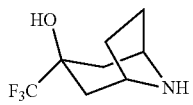

The product was obtained analogously to IP 5d starting from endo-8-benzyl-3-trifluoromethyl-8-azabicyclo[3.2.1]octan-3-ol 1 (IP 11a, fraction 2). Yield: 2.30 g (96% of theoretical); $C_8H_{12}F_3NO$ (M=195.182); calc.: molpeak (M+H)$^+$: 196; found: molpeak (M+H)$^+$: 196.

Intermediate Product 13

5-(4-chlorophenyl)-2-ethynylpyridine

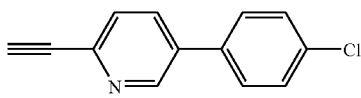

IP 13a. 5-bromo-2-[(tert-butyldimethylsilanyl)ethynyl]pyridine

Under an argon atmosphere 0.80 g (4.20 mmol) of CuI and 2.90 g (4.13 mmol) of bis(triphenylphosphane)palladium (II) chloride were added to a solution of 49.90 g (201.0 mmol) of 2,5-dibromopyridine and 43.0 mL (225.6 mmol) of tert-butylethynyldimethylsilane in 500 mL of dry THF and 120 mL of triethylamine at −7° C. and the mixture was stirred for 30 minutes at 0° C. The reaction mixture was stirred for a further 3.5 hours at RT, then filtered and the filtrate was evaporated down in vacuo. The residue was dissolved in 1 L of EtOAc, the organic phase was washed with water and saturated NaCl solution, dried over sodium sulfate, and evaporated down in vacuo. The crude product was reacted further without purification. Yield: 59.5 g (quant. yield); $C_{13}H_{18}BrNSi$ (M=296.278); calc.: molpeak (M+H)$^+$: 296/298 (Br); found: molpeak (M+H)$^+$: 296/298 (Br); $R_f$ value: 0.75 (silica gel, cyc/EtOAc 8:1).

IP 13b. 2-[(tert-butyldimethylsilanyl)ethynyl]-5-(4-chlorophenyl)pyridine 250 mL of MeOH, 220 mL of 2N sodium carbonate solution, and 1.80 g (2.46 mmol) of PdCl$_2$(dppf) were added to a solution of 59.5 g (201.0 mmol) of 5-bromo-2-[(tert-butyldimethylsilanyl)ethynyl]pyridine and 36.5 g (233.4 mmol) of 4-chlorophenylboric acid in 600 mL of 1,4-dioxane and the mixture was refluxed for 1 hour. The reaction mixture was evaporated down in vacuo and diluted with EtOAc. The organic phase was washed with water and semisaturated sodium bicarbonate solution, dried over sodium sulfate and evaporated down in vacuo. The residue was purified by column chromatography (silica gel, cyc/EtOAc 9:1). Yield: 38.5 g (58% of theoretical); $C_{19}H_{22}ClNSi$ (M=327.923); calc.: molpeak (M+H)$^+$: 328/330 (Cl); found: molpeak (M+H)$^+$: 328/330 (Cl); $R_f$ value: 0.60 (silica gel, cyc/EtOAc 8:1).

IP 13c. 5-(4-chlorophenyl)-2-ethynylpyridine 43.66 g (156.0 mmol) of TBAF was added to a solution of 46.50 g (142.0 mmol) of 2-[(tert-butyldimethylsilanyl)ethynyl]-5-(4-chlorophenyl)pyridine in 1 L of DCM at RT and the mixture was stirred for 2 hours. The organic phase was washed with water, dried over sodium sulfate, and evaporated down in vacuo. The residue was stirred with DIPE, and the precipitate was filtered off and washed with PE. Yield: 26.0 g (86% of theoretical); $C_{13}H_8ClN$ (M=213.662); calc.: molpeak (M+H)$^+$: 214/216 (Cl); found: molpeak (M+H)$^+$: 214/216 (Cl); $R_f$ value: 0.30 (silica gel, cyc/EtOAc 4:1).

Intermediate Product 14

6-bromo-2-chloro-4-methylquinoline

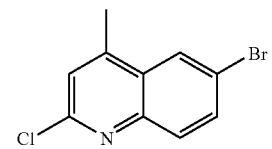

IP 14a. N-(4-bromophenyl)-3-oxobutyramide

A solution of 25.72 mL (336 mmol) of diketene in 100 mL of toluene was added dropwise at 90° C. to a solution of 51.0 g (288 mmol) of 4-bromoaniline in 200 mL of toluene and the reaction mixture was kept at this temperature for 5 hours. The reaction solution was cooled in the ice bath, and the precipitate formed was filtered and washed with toluene until the product was virtually colorless. Subsequently it was dried at 50° C. in the circulating air dryer until a constant weight was obtained. Yield: 50.0 g (68% of theoretical); $C_{10}H_{10}BrNO_2$ (M=256.096); calc.: molpeak $(M+H)^+$: 256/258 (Br); found: molpeak $(M+H)^+$: 256/258 (Br); HPLC-MS: 4.7 minutes (method B).

IP 14b. 6-bromo-4-methyl-1H-quinolin-2-one

A solution of 50.0 g (195 mmol) of N-(4-bromophenyl)-3-oxobutyramide in 217 mL of concentrated sulfuric acid was heated to 120° C. for 1 hour. After cooling to RT, the reaction solution was added to 1.5 L of ice water, stirred for 30 minutes, and the precipitate formed was filtered and washed with 4 L of water. Subsequently it was dried at 35° C. in the circulating air dryer until a constant weight was achieved. Yield: 24.0 g (52% of theoretical); $C_{10}H_8BrNO$ (M=238.081); calc.: molpeak $(M+H)^+$: 238/240 (Br); found: molpeak $(M+H)^+$: 238/240 (Br); HPLC-MS: 4.8 minutes (method B).

IP 14c. 6-bromo-2-chloro-4-methylquinoline 25 mL of phosphorus oxychloride was added to 2.7 g (11.34 mmol) of 6-bromo-4-methyl-1H-quinolin-2-one (Example 1b) and the reaction mixture was refluxed for 2 hours. After cooling, the mixture was added batchwise to 250 mL of 10% $NH_3$ solution, and the precipitate formed was filtered off, washed with water, and dried in the circulating air dryer at 30° C. Yield: 2.7 g (93% of theoretical); $C_{10}H_7BrClN$ (M=256.526); calc.: molpeak $(M+H)^+$: 256/258/260 (BrCl); found: molpeak $(M+H)^+$: 256/258/260 (BrCl); $R_f$ value: 0.95 (silica gel, DCM/MeOH 9:1).

Intermediate Product 15

1-[2-(4-iodophenoxy)ethyl]-4-methylpiperidin-4-ol

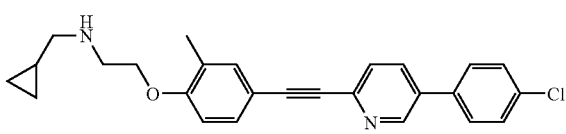

IP 15a. 2-(4-iodophenoxy)ethyl methanesulfonate

The product was obtained analogously to Example 1.1f (with DCM as solvent) from 34.4 g (130 mmol) of 2-(4-iodophenoxy)ethanol. Yield: 41.5 g (45% of theoretical); $C_9H_{11}IO_4S$ (M=342.152); calc.: molpeak $(M+NH_4)^+$: 360; found: molpeak $(M+NH_4)^+$: 360; $R_f$ value: 0.65 (silica gel, PE/EtOAc 1:1).

IP 15b. 1-[2-(4-iodophenoxy)ethyl]-4-methylpiperidin-4-ol

The product was obtained analogously to Example 1.1g (3 hours at 70° C., potassium carbonate as base) from 4.79 g (14.0 mmol) of 2-(4-iodophenoxy)ethyl methanesulfonate and 1.94 g (16.8 mmol) of 4-methylpiperidin-4-ol. Yield: 3.40 g (67% of theoretical); $C_{14}H_{20}INO_2$ (M=361.219); calc.: molpeak $(M+H)^+$: 362; found: molpeak $(M+H)^+$: 362; $R_f$ value: 0.20 (silica gel, DCM/MeOH 9:1).

Intermediate Product 16

4-isopropylpiperidin-4-ol

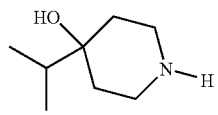

IP 16a. 1-benzyl-4-isopropylpiperidin-4-ol

Under a nitrogen atmosphere, first 700 mL of a THF/diethyl ether mixture (2:1) and then a solution of 53.0 mL (283 mmol) of N-benzyl-4-piperidone in 200 mL of a THF/diethyl ether mixture (2:1) were slowly added at −15° C. to 200 mL (400 mmol, 2 M in THF) of isopropylmagnesium chloride solution and the reaction mixture was stirred for 1 hour between −3° C. and −6° C. While cooling with ice, 600 mL of water was slowly added dropwise and the mixture was stirred for 30 minutes. Then 400 mL of EtOAc and 100 mL of diethyl ether were added. The organic phase was separated off and dried over sodium sulfate. After the desiccant and solvent had been eliminated, the residue was purified by chromatography (silica gel, DCM/MeOH/$NH_3$ 98:2:0.2). Yield: 9.85 g (15% of theoretical); $C_{15}H_{23}NO$ (M=233.349); calc.: molpeak $(M+H)^+$: 234; found: molpeak $(M+H)^+$: 234; HPLC-MS: 4.1 minutes (method G).

IP 16b. 4-isopropylpiperidin-4-ol

The product was obtained analogously to Example IP 5d from 9.85 g (42.2 mmol) of 1-benzyl-4-isopropylpiperidin-4-ol. Yield: 1.13 g (19% of theoretical); $C_8H_{17}NO$ (M=143.227); calc.: molpeak $(M+H)^+$: 144; found: molpeak $(M+H)^+$: 144; $R_f$ value: 0.07 (silica gel, EtOAc/MeOH/$NH_3$ 5:5:0.5).

EXAMPLE 1.1

(2-{4-[5-(4-chlorophenyl)pyridin-2-ylethynyl]-2-methylphenoxy}ethyl)cyclopropylmethylamine

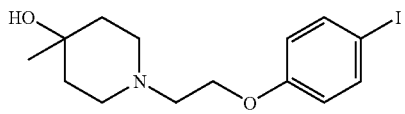

1.1 a. 2-(4-iodo-2-methylphenoxy)ethanol

Under a nitrogen atmosphere, 2.34 g (10 mmol) of 4-iodo-2-methylphenol was added batchwise to a suspension of 0.48 g (11 mmol) of NaH in 50 mL of THF cooled to 0° C. and the mixture was stirred for a further 30 minutes at this temperature. Then 0.85 mL (12 mmol) of 2-bromoethanol dissolved in 5 mL of THF was added dropwise and the mixture was stirred for 18 hours at RT. 5 mL of DMF was added and the reaction mixture was heated to 70° C. for 8 hours. It was evaporated down in vacuo, the residue was taken up in water, extracted exhaustively with EtOAc and dried over sodium sulfate. After the desiccant and solvent had been eliminated, the residue was purified by chromatography on silica gel (cyc/EtOAc 7:3). Yield: 0.39 g (14% of theoretical); $C_9H_{11}IO_2$ (M=278.091); calc.: molpeak (M+H)$^+$: 279; found: molpeak (M+H)$^+$: 279; R$_f$ value: 0.28 (silica gel, cyc/EtOAc 2:1).

1.1b. 2-(2-methyl-4-trimethylsilanylethynylphenoxy)ethanol 31 mg (0.160 mmol) of CuI was added under argon to a degassed solution of 2:225 g (8.000 mmol) of 2-(4-iodo-2-methylphenoxy)ethanol, 1.22 mL (8.80 mmol) of trimethylsilylacetylene, 185 mg (0.160 mmol) of tetrakis(triphenylphosphane)palladium, and 2.38 mL (24.00 mmol) of piperidine in 50 mL of THF and the mixture was stirred for 1 hour at RT. The reaction mixture was diluted with water and the aqueous phase was exhaustively extracted with EtOAc. The combined organic phases were washed with saturated aqueous NaCl solution, dried over sodium sulfate, and evaporated down in vacuo. Purification of the crude product by column chromatography (silica gel, cyc/EtOAc 2:1) yielded light brown crystals. Yield: 1.70 g (86% of theoretical); $C_{14}H_{20}O_2Si$ (M=248.393); calc.: molpeak (M+H)$^+$: 249; found: molpeak (M+H)$^+$: 249; R$_f$ value: 0.24 (silica gel, cyc/EtOAc 2:1).

1.1c. 2-(4-ethynyl-2-methylphenoxy)ethanol 20.8 g (74.4 mmol) of TBAF was added at RT to a solution of 16.8 g (67.6 mmol) of 2-(2-methyl-4-trimethylsilanylethynylphenoxy)ethanol in 500 mL of THF and the mixture was stirred for 3 hours at RT. The reaction mixture was evaporated down in vacuo and the residue dissolved in EtOAc. The organic phase was washed with water and saturated aqueous NaCl solution, dried over sodium sulfate, and evaporated down in vacuo. The crude product was used in the next reaction step without further purification. Yield: 12.0 g (quant. yield); $C_{11}H_{12}O_2$ (M=176.212); calc.: molpeak (M)$^+$: 176; found: molpeak (M)$^+$: 176; R$_f$ value: 0.24 (silica gel, cyc/EtOAc 2:1).

1.1d. 2-[4-(5-bromopyridin-2-ylethynyl)-2-methylphenoxy]ethanol 0.26 g (1.36 mmol) of CuI was added to a degassed solution of 11.98 g (68.00 mmol) of 2-(4-ethynyl-2-methylphenoxy)ethanol, 16.11 g (68.00 mmol) of 2,5-dibromopyridine, 0.96 g (1.36 mmol) of bis(triphenylphosphane)palladium (II) chloride, and 19.22 mL (136.00 mmol) of diisopropylamine in 500 mL of THF and the mixture was stirred for 4 hours at RT. The reaction mixture was evaporated down in vacuo and the residue taken up in 800 mL of EtOAc. The organic phase was with water and saturated aqueous NaCl solution washed, dried over sodium sulfate, and evaporated down in vacuo. The crude product was purified by column chromatography (silica gel, gradient DCM/EtOAc 90:10→80:20). Yield: 13.20 g (58% of theoretical); $C_{16}H_{14}BrNO_2$ (M=332.192); calc.: molpeak (M+H)$^+$: 332/334 (Br); found: molpeak (M+H)$^+$: 332/334 (Br); R$_f$ value: 0.39 (silica gel, cyc/EtOAc 1:1).

1.1e. 2-{4-[5-(4-chlorophenyl)pyridin-2-ylethynyl]-2-methylphenoxy}ethanol 40 mL of 2 N aqueous sodium bicarbonate solution was added to a suspension of 13.20 g (39.74 mmol) of 2-[4-(5-bromopyridin-2-ylethynyl)-2-methylphenoxy]ethanol, 9.32 g (59.60 mmol) of 4-chlorophenylboric acid, and 2.30 g (1.99 mmol) of tetrakis(triphenylphosphane)palladium in 400 mL of 1,4-dioxane and the mixture was refluxed for 12 hours. Another 4.66 g of 4-chlorophenylboric acid and 1.14 g of tetrakis(triphenylphosphane)palladium were added and the mixture was refluxed for 8 hours. The reaction mixture was evaporated down in vacuo and the residue was stirred with EtOAc and water. The precipitate was filtered off, washed with diethyl ether, and dried in vacuo. Yield: 10.70 g (74% of theoretical); $C_{22}H_{18}ClNO_2$ (M=363.837); calc.: molpeak (M+H)$^+$: 364/366 (Cl); found: molpeak (M+H)$^+$: 364/366 (Cl); R$_f$ value: 0.47 (silica gel, DCM/EtOAc 2:1).

1.1f. 2-{4-[5-(4-chlorophenyl)pyridin-2-ylethynyl]-2-methylphenoxy}ethyl methanesulfonate 2.74 mL (35.29 mmol) of methanesulfonic acid chloride was added dropwise at 0° C. to a solution of 10.70 g (29.41 mmol) of 2-{4-[5-(4-chlorophenyl)pyridin-2-ylethynyl]-2-methylphenoxy}ethanol and 4.08 mL (29.41 mmol) of triethylamine in 500 mL of THF and the mixture was then stirred for 2 hours at RT. The reaction mixture was filtered and the filtrate was evaporated down in vacuo. The residue was stirred with diethyl ether and water, and the precipitate was filtered off and dried in vacuo. Yield: 11.00 g (85% of theoretical); $C_{23}H_{20}ClNO_4S$ (M=441.928); calc.: molpeak (M+H)$^+$: 442/444 (Cl); found: molpeak (M+H)$^+$: 442/444 (Cl); HPLC-MS: 6.36 minutes (method C).

1.1g. (2-{4-[5-(4-chlorophenyl)pyridin-2-ylethynyl]-2-methylphenoxy}ethyl)cyclopropylmethylamine A mixture of 1.00 g (2.26 mmol) of 2-{4-[5-(4-chlorophenyl)pyridin-2-ylethynyl]-2-methylphenoxy}ethyl methanesulfonate, 0.99 mL (11.32 mmol) of C-cyclopropylmethylamine, and 1.92 mL (11.32 mmol) of ethyldiisopropylamine in 15 mL of DMF was stirred for 3 days at 60° C. and then evaporated down in vacuo. The crude product was purified by column chromatography (silica gel, EtOAc/MeOH/saturated aqueous ammonia 19:1:0.1). The residue was dissolved in DCM, and the organic phase was washed with water, dried over sodium sulfate and evaporated down in vacuo. The residue was stirred with PE, the precipitate was filtered off and dried in vacuo. Yield: 270 mg (29% of theoretical); $C_{26}H_{25}ClN_2O$ (M=416.942); calc.: molpeak (M+H)$^+$: 417/419 (Cl); found: molpeak (M+H)$^+$: 417/419 (Cl); R$_f$ value: 0.39 (silica gel, EtOAc/MeOH/saturated aqueous ammonia 9:1:0.1); HPLC-MS: 8.21 minutes (method A).

The following Examples were prepared analogously starting from 2-{4-[5-(4-chlorophenyl)pyridin-2-ylethynyl]-2-methylphenoxy}ethyl methanesulfonate (Example 1.1f).

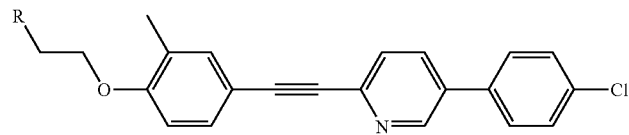

| Example | R | Yield (%) | empirical formula | mass spectrum | retention time HPLC in minutes (method) |
|---|---|---|---|---|---|
| 1.2 | cyclopentyl-NH-* | 66 | $C_{27}H_{27}ClN_2O$ | 431/433 $[M+H]^+$ | 8.90 (A) |
| 1.3 | cyclopentyl-CH2-NH-* | 42 | $C_{28}H_{29}ClN_2O$ | 445/447 $[M+H]^+$ | 5.91 (B) |
| 1.4 | (S)-2-(methoxymethyl)pyrrolidin-1-yl | 30 | $C_{28}H_{29}ClN_2O_2$ | 461/463 $[M+H]^+$ | 8.65 (A) |
| 1.5 | (R)-2-(methoxymethyl)pyrrolidin-1-yl | 26 | $C_{28}H_{29}ClN_2O_2$ | 461/463 $[M+H]^+$ | 8.65 (A) |
| 1.6 | 4-hydroxy-4-(trifluoromethyl)piperidin-1-yl | 66 | $C_{28}H_{26}ClF_3N_2O_2$ | 515/517 $[M+H]^+$ | 8.50 (A) |
| 1.7 | 4-(1-hydroxy-2,2,2-trifluoroethyl)piperidin-1-yl | 28 | $C_{29}H_{28}ClF_3N_2O_2$ | 529/531 $[M+H]^+$ | 8.85 (A) |
| 1.8 | 4-(trifluoroacetyl)piperidin-1-yl | 11 | $C_{29}H_{26}ClF_3N_2O_2$ | 527/529 $[M+H]^+$ | 8.85 (A) |
| 1.9 | N-cyclohexyl-N-cyclopentyl-amino | 6 | $C_{33}H_{37}ClN_2O$ | 513/515 $[M+H]^+$ | 6.12 (B) |

-continued

| Example | R | Yield (%) | empirical formula | mass spectrum | retention time HPLC in minutes (method) |
|---|---|---|---|---|---|
| 1.10 | (3,4-dihydroxy-4-trifluoromethyl piperidinyl, stereo) | 39 | C$_{28}$H$_{26}$ClF$_3$N$_2$O$_3$ | 531/533 [M + H]$^+$ | 8.20 (A) |
| 1.11 | (3,4-dihydroxy-4-trifluoromethyl piperidinyl, stereo) | 15 | C$_{28}$H$_{26}$ClF$_3$N$_2$O$_3$ | 531/533 [M + H]$^+$ | 8.30 (A) |
| 1.12 | HOCH$_2$C(CH$_3$)$_2$NH– | 86 | C$_{26}$H$_{27}$ClN$_2$O$_2$ | 435/437 [M + H]$^+$ | 5.20 (B) |
| 1.13 | 1-(hydroxymethyl)cyclopentyl-NH– | 81 | C$_{28}$H$_{29}$ClN$_2$O$_2$ | 461/463 [M + H]$^+$ | 5.45 (B); |
| 1.14 | 4-hydroxy-4-isopropyl-piperidinyl | 54 | C$_{30}$H$_{33}$ClN$_2$O$_2$ | 489/491 [M + H]$^+$ | 5.1 (H); |
| 1.15 | 3-hydroxy-3-methyl-8-azabicyclo[3.2.1]octyl | 98 | C$_{30}$H$_{31}$ClN$_2$O$_2$ | 487/489 [M + H]$^+$ | |
| 1.16 | 3-ethyl-3-hydroxy-8-azabicyclo[3.2.1]octyl | 92 | C$_{31}$H$_{33}$ClN$_2$O$_2$ | 501/503 [M + H]$^+$ | 5.04 (H) |
| 1.17 | 3-hydroxy-3-trifluoromethyl-8-azabicyclo[3.2.1]octyl | 84 | C$_{30}$H$_{28}$ClF$_3$N$_2$O$_2$ | 541/543 [M + H]$^+$ | 5.18 (H) |
| 1.18 | 3-hydroxy-3-trifluoromethyl-8-azabicyclo[3.2.1]octyl | 82 | C$_{30}$H$_{28}$ClF$_3$N$_2$O$_2$ | 541/543 [M + H]$^+$ | 5.13 (H) |

-continued

| Example | R | Yield (%) | empirical formula | mass spectrum | retention time HPLC in minutes (method) |
|---|---|---|---|---|---|
| 1.19 | OH (4-ethyl-4-hydroxypiperidin-1-yl) | 93 | $C_{29}H_{31}ClN_2O_2$ | 475/477 $[M+H]^+$ | 4.9 (H); |

EXAMPLE 2.1

(2-{4-[5-(4-chlorophenyl)pyridin-2-ylethynyl]-2-methylphenoxy}ethyl)cyclohexylcyclopropylmethylamine

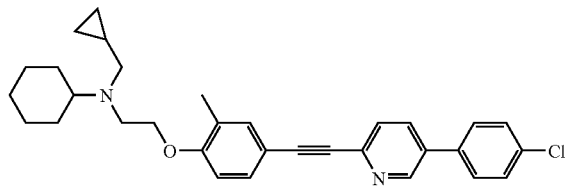

30 μL (0.29 mmol) of cyclohexanone, 1 drop of AcOH, and 128 mg (0.68 mmol) of sodium triacetoxyborohydride were added to a solution of 60 mg (0.14 mmol) of (2-{4-[5-(4-chlorophenyl)pyridin-2-ylethynyl]-2-methylphenoxy}ethyl)cyclopropylmethylamine in 10 mL of THF and the mixture was stirred for 24 hours at RT. 5 mL of DCM, 30 μL (0.29 mmol) of cyclohexanone, and 36 mg (0.58 mmol) of sodium cyanoborohydride were added and the mixture was stirred for a further 3 days. The reaction mixture was evaporated down in vacuo and the residue was taken up in EtOAc. The organic phase was washed with semiconcentrated aqueous sodium bicarbonate solution, dried over sodium sulfate, and evaporated down in vacuo. The residue was purified by column chromatography (silica gel, cyc/EtOAc 1:1) and triturated with PE. Yield: 4.5 mg (6% of theoretical); $C_{32}H_{35}ClN_2O$ (M=499.086); calc.: molpeak $(M+H)^+$: 499/501 (Cl); found: molpeak $(M+H)^+$: 499/501 (Cl); HPLC-MS: 9.85 minutes (method A).

The following Examples were prepared analogously.

| Example (from Example) | R | Yield (%) | empirical formula | mass spectrum | retention time HPLC in minutes (method) |
|---|---|---|---|---|---|
| 2.2 (from 1.2) | 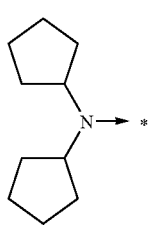 | 3 | $C_{32}H_{35}ClN_2O$ | 499/501 $[M+H]^+$ | |

-continued

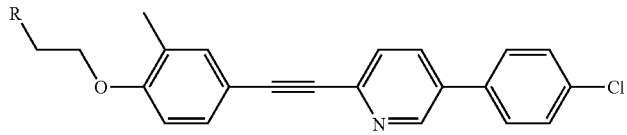

| Example (from Example) | R | Yield (%) | empirical formula | mass spectrum | retention time HPLC in minutes (method) |
|---|---|---|---|---|---|
| 2.3 (from 1.2) | cyclopentyl-N-CH2-cyclopropyl | 45 | $C_{31}H_{33}ClN_2O$ | 485/487 $[M + H]^+$ | 6.50 (B) |
| 2.4 (from 1.3) | cyclopentyl-N-CH2-cyclopropyl (with CH2 spacer) | 37 | $C_{32}H_{35}ClN_2O$ | 499/501 $[M + H]^+$ | 6.91 (B) |
| 2.5 (from 1.3) | bis(cyclopentylmethyl)amine | 81 | $C_{33}H_{37}ClN_2O$ | 513/515 $[M + H]^+$ | 7.10 (B) |
| 2.6 (From 1.3) | cyclopentylmethyl-N-cyclohexyl | 62 | $C_{34}H_{39}ClN_2O$ | 527/529 $[M + H]^+$ | 7.60 (B) |

EXAMPLE 3.1

2-[(2-{4-[5-(4-chlorophenyl)pyridin-2-ylethynyl]-2-methylphenoxy}ethyl)cyclopentylamino]ethanol

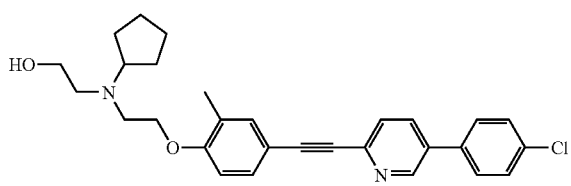

55 mg (0.40 mmol) of potassium carbonate and 28 µL (0.40 mmol) of 2-bromoethanol was added to a solution of 86.2 mg (0.20 mmol) of (2-{4-[5-(4-chlorophenyl)pyridin-2-ylethynyl]-2-methylphenoxy}ethyl)cyclopentylamine in 2 mL of DMF and the mixture was stirred for 24 hours at RT. Another 55 mg (0.40 mmol) of potassium carbonate and 28 µL (0.40 mmol) of 2-bromoethanol were added and the mixture was stirred for 8 hours at 50° C. The reaction mixture was evaporated down in vacuo and the residue was taken up in DCM. The organic phase was washed with water, dried over sodium sulfate, and evaporated down in vacuo. The crude product was purified by MPLC (silica gel, EtOAc/MeOH 95:5) and then MPLC (Alox, cyc/EtOAc 8:2) and triturated with DIPE. Yield: 2.9 mg (3% of theoretical); $C_{29}H_{31}ClN_2O_2$ (M=475.021); calc.: molpeak $(M+H)^+$: 475/477 (Cl); found: molpeak $(M+H)^+$: 475/477 (Cl); $R_f$ value: 0.26 (silica gel, EtOAc/MeOH 95:5)

The following Examples were prepared analogously.

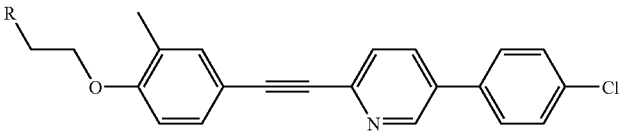

| Example (from Example) | R | Yield (%) | empirical formula | mass spectrum | retention time HPLC in minutes (method) |
|---|---|---|---|---|---|
| 3.2 (from 1.2) | ![structure] | 23 | $C_{30}H_{33}ClN_2O_2$ | 489/491 $[M+H]^+$ | 5.60 (B) |
| 3.3 (from 1.3) | ![structure] | 28 | $C_{31}H_{35}ClN_2O_2$ | 503/505 $[M+H]^+$ | 6.07 (B) |
| 3.4 (from 1.3) | ![structure] | 13 | $C_{30}H_{33}ClN_2O_2$ | 489/491 $[M+H]^+$ | 5.96 (B) |

EXAMPLE 4.1

[(S)-1-(2-{4-[5-(4-chlorophenyl)pyridin-2-ylethynyl]phenoxy}ethyl)pyrrolidin-2-yl]methanol

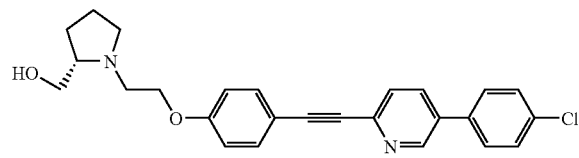

4.1a. 2-(4-trimethylsilanylethynylphenoxy)ethanol

The product was obtained analogously to Example 1.1b starting from 15.10 g (57.18 mmol) of 2-(4-iodophenoxy)ethanol. Yield: 12.20 (91% of theoretical); $C_{13}H_{18}O_2Si$ (M=234.366); $R_f$ value: 0.40 (silica gel, PE/EtOAc 6:4).

4.1b. 2-(4-ethynylphenoxy)ethanol

The product was obtained analogously to Example 1.1c starting from 12.20 g (52.05 mmol) of 2-(4-trimethylsilanyl-ethynylphenoxy)ethanol. Yield: 7.70 g (91% of theoretical); $C_{10}H_{10}O_2$ (M=162.185); calc.: molpeak $(M+H)^+$: 163; found: molpeak $(M+H)^+$: 163; $R_f$ value: 0.32 (silica gel, PE/EtOAc 6:4).

4.1c. 2-[4-(5-bromopyridin-2-ylethynyl)phenoxy]ethanol

The product was obtained analogously to Example 1.1d starting from 7.70 g (47.48 mmol) of 2-(4-ethynylphenoxy)ethanol and 11.37 g (48.00 mmol) of 2,5-dibromopyridine. Yield: 7.40 g (49% of theoretical); $C_{15}H_{12}BrNO_2$ (M=318.165); calc.: molpeak $(M+H)^+$: 318/320 (Br); found: molpeak $(M+H)^+$: 318/320 (Br); $R_f$ value: 0.20 (silica gel, PE/EtOAc 6:4).

4.1d. 2-{4-[5-(4-chlorophenyl)pyridin-2-ylethynyl]phenoxy}ethanol

The product was obtained analogously to Example 1.1e from 2-[4-(5-bromopyridin-2-ylethynyl)phenoxy]ethanol and 5.47 g (35.00 mmol) of 4-chlorophenylboric acid. Yield: 4.40 g (54% of theoretical); $C_{21}H_{16}ClNO_2$ (M=349.810); calc.: molpeak $(M+H)^+$: 350/352 (Cl); found: molpeak $(M+H)^+$: 350/352 (Cl); HPLC-MS: 9.10 minutes (method A).

4.1e. 2-{4-[5-(4-chlorophenyl)pyridin-2-ylethynyl]phenoxy}ethyl methanesulfonate The product was obtained analogously to Example 1.1f starting from 4.40 g (12.58 mmol) of 2-{4-[5-(4-chlorophenyl)pyridin-2-ylethynyl]phenoxy}ethanol. Yield: 4.50 g (84% of theoretical); $C_{22}H_{18}ClNO_4S$ (M=427.901); calc.: molpeak $(M+H)^+$: 428/430 (Cl); found: molpeak $(M+H)^+$: 428/430 (Cl); $R_f$ value: 0.88 (silica gel, EtOAc).

4.1f. [(S)-1-(2-{4-[5-(4-chlorophenyl)pyridin-2-yl-ethynyl]phenoxy}ethyl)pyrrolidin-2-yl]methanol The product was obtained analogously to Example 1.1g starting from 2-{4-[5-(4-chlorophenyl)pyridin-2-ylethynyl]phenoxy}ethyl methanesulfonate and (S)-1-pyrrolidin-2-yl-methanol. Yield: 170 mg (79% of theoretical); $C_{26}H_{25}ClN_2O_2$ (M=432.942); calc.: molpeak (M+H)$^+$: 433/435 (Cl); found: molpeak (M+H)$^+$: 433/435 (Cl); HPLC-MS: 4.75 minutes (method B).

The following Examples were prepared analogously starting from 2-{4-[5-(4-chlorophenyl)pyridin-2-ylethynyl]phenoxy}ethyl methanesulfonate (Example 4.1e).

| Example | R | Yield (%) | empirical formula | mass spectrum | retention time HPLC in minutes (method) |
|---|---|---|---|---|---|
| 4.2 | cyclohexyl-N(CH2-cyclopropyl)- | 41 | $C_{31}H_{33}ClN_2O$ | 485/487 [M + H]$^+$ | 6.24 (B) |
| 4.3 | 4-OH-4-CF3-piperidinyl | 50 | $C_{27}H_{24}ClF_3N_2O_2$ | 501/503 [M + H]$^+$ | 5.26 (A) |
| 4.4 | 4-(CH(OH)CF3)-piperidinyl | 9 | $C_{28}H_{26}ClF_3N_2O_2$ | 515/517 [M + H]$^+$ | 5.38 (B) |
| 4.5 | 4-(C(O)CF3)-piperidinyl | 19 | $C_{28}H_{24}ClF_3N_2O_2$ | 513/515 [M + H]$^+$ | 8.04 (A) |
| 4.6 | propyl-N(CH2-cyclopropyl)- | 66 | $C_{28}H_{29}ClN_2O$ | 445/447 [M + H]$^+$ | 5.61 (B) |
| 4.7 | 3-OH-4-OH-4-CF3-piperidinyl (trans) | 45 | $C_{27}H_{24}ClF_3N_2O_3$ | 517/519 [M + H]$^+$ | 7.70 (A) |
| 4.8 | 3-OH-4-OH-4-CF3-piperidinyl (cis) | 22 | $C_{27}H_{24}ClF_3N_2O_3$ | 517/519 [M + H]$^+$ | 7.90 (A) |

-continued

| Example | R | Yield (%) | empirical formula | mass spectrum | retention time HPLC in minutes (method) |
|---|---|---|---|---|---|
| 4.9 | HO, H₃C- (azabicyclic) | 80 | C₂₉H₂₉ClN₂O₂ | 473/475 [M + H]⁺ | 5.35 (B) |
| 4.10 | HO, H₃C-CH₂- (azabicyclic) | 92 | C₃₀H₃₁ClN₂O₂ | 487/489 [M + H]⁺ | 5.31 (B) |
| 4.11 | F₃C, HO (azabicyclic) | | C₂₉H₂₆ClF₃N₂O₂ | 527/529 [M + H]⁺ | 5.58 (B) |
| 4.12 | HO, F₃C (azabicyclic) | 46 | C₂₉H₂₆ClF₃N₂O₂ | 527/529 [M + H]⁺ | |
| 4.13 | OH, CH₃, NH | 80 | C₂₄H₂₃ClN₂O₂ | 407/409 [M + H]⁺ | 4.95 (B) |
| 4.14 | HO, C(CH₃)₂, NH | 83 | C₂₅H₂₅ClN₂O₂ | 421/423 [M + H]⁺ | 4.98 (B) |
| 4.15 | HO-CH₂-cyclopentyl-NH | 87 | C₂₅H₂₅ClN₂O₂ | 447/449 [M + H]⁺ | 5.26 (B) |
| 4.16 | OH, isopropyl-piperidinyl | 53 | C₂₉H₃₁ClN₂O₂ | 475/77 [M + H]⁺ | 4.9 (H) |
| 4.17 | OH, ethyl-piperidinyl | 76 | C₂₈H₂₉ClN₂O₂ | 461/463 [M + H]⁺ | 4.7 (H) |

EXAMPLE 5.1

(2-{4-[5-(4-chlorophenyl)pyridin-2-ylethynyl]phenoxy}ethyl)cyclopentylcyclopropylmethylamine

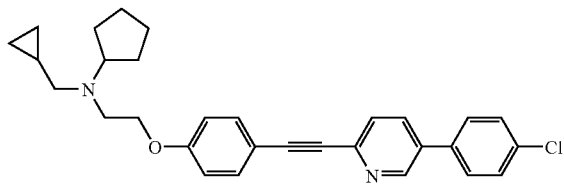

5.1a. (2-{4-[5-(4-chlorophenyl)pyridin-2-ylethynyl]phenoxy}ethyl)cyclopropylmethylamine The product was obtained analogously to Example 4.1f starting from 2-{4-[5-(4-chlorophenyl)pyridin-2-ylethynyl]phenoxy}ethyl methanesulfonate (Example 4.1e) and C-cyclopropylmethylamine. Yield: 700 mg (43% of theoretical); $C_{25}H_{23}ClN_2O$ (M=402.916); calc.: molpeak (M+H)$^+$: 403/405 (Cl); found: molpeak (M+H)$^+$: 403/405 (Cl); HPLC-MS: 5.08 minutes (method B).

5.1b. (2-{4-[5-(4-chlorophenyl)pyridin-2-ylethynyl]phenoxy}ethyl)cyclopentylcyclopropylmethylamine A mixture of 80.6 mg (0.20 mmol) of (2-{4-[5-(4-chlorophenyl)pyridin-2-ylethynyl]phenoxy}ethyl)cyclopropylmethylamine, 35 μL (0.40 mmol) of cyclopentanone, and one drop of AcOH in 10 mL of THF was stirred for 15 minutes. 169.5 mg (0.80 mmol) of sodium triacetoxyborohydride was added and the mixture was stirred for 24 hours at RT. A further 17.5 μL of cyclopentanone and 85 mg of sodium triacetoxyborohydride were added and the mixture was again stirred for 24 hours at RT. The reaction mixture was diluted with water, made basic with saturated aqueous potassium carbonate solution, and the aqueous phase was extracted with EtOAc. The combined organic phases were dried over sodium sulfate and evaporated down in vacuo. The crude product was purified by column chromatography (silica gel, EtOAc/MeOH/conc. aqueous ammonia 98:2:0.2) and stirred with DIPE. Yield: 22 mg (23% of theoretical); $C_{30}H_{31}ClN_2O$ (M=471.033); calc.: molpeak (M+H)$^+$: 471/473 (Cl); found: molpeak (M+H)$^+$: 471/473 (Cl); HPLC-MS: 5.83 minutes (method B).

EXAMPLE 6.1

3-[(2-{4-[5-(4-chlorophenyl)pyridin-2-ylethynyl]phenoxy}ethyl)cyclopropylmethylamino]propan-1-ol

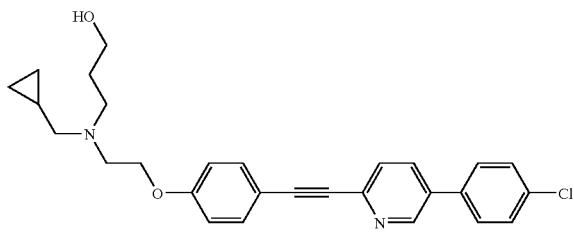

The product was obtained analogously to Example 3.1 starting from (2-{4-[5-(4-chlorophenyl)pyridin-2-ylethynyl]phenoxy}ethyl)cyclopropylmethylamine (Example 5.1a) and 3-bromopropanol. Yield: 9 mg (10% of theoretical); $C_{28}H_{29}ClN_2O_2$ (M=460.995); calc.: molpeak (M+H)$^+$: 461/463 (Cl); found: molpeak (M+H)$^+$: 461/463 (Cl); HPLC-MS: 5.14 minutes (method B).

EXAMPLE 7.1

[(S)-1-(2-{4-[5-(4-chlorophenyl)-3-fluoropyridin-2-ylethynyl]phenoxy}ethyl)pyrrolidin-2-yl]methanol

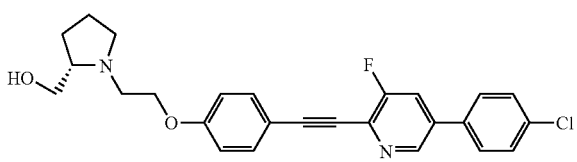

7.1a. 2,5-dibromo-3-fluoropyridine

A solution of 1.78 g (25.80 mmol) of sodium nitrite in 3.5 mL of water was added dropwise at −5° C. to a solution of 6.50 g (25.80 mmol) of 2,5-dibromopyridin-3-ylamine and 15 mL of concentrated aqueous HCl (180.62 mmol) in 15 mL of water and the mixture was stirred for 30 minutes. At 0° C., 11.41 mL (77.41 mmol) of hexafluorophosphoric acid (60% in water) was added and the mixture was stirred for 1 hour at 0° C. The diazonium salt formed was filtered off, washed with cold water, isopropanol, and diethyl ether, and dried in vacuo in the desiccator. PE (100° C.-140° C.) was heated to 90° C., the diazonium salt was added batchwise, and the mixture was stirred until there was further development of gas could be perceived. The reaction mixture was cooled to RT, made alkaline with saturated aqueous sodium carbonate solution, and the aqueous phase was exhaustively extracted with MTBE. The combined organic phases were washed with saturated aqueous sodium carbonate solution and water, dried over magnesium sulfate, and evaporated down in vacuo. The residue was dissolved in DCM, filtered through silica gel, and the filtrate was evaporated down in vacuo. Yield: 3.30 (51% of theoretical); $C_5H_2Br_2FN$ (M=254.883); calc.: molpeak (M+H)$^+$: 253/255/257 (2Br); found: molpeak (M+H)$^+$: 253/255/257 (2Br); $R_f$ value: 0.63 (silica gel, PE/EtOAc 9:1).

7.1b. 5-bromo-2-[(tert-butyldimethylsilanyl)ethynyl]-3-fluoropyridine

Under an argon atmosphere, 2.62 mL (13.811 mmol) of tert-butylethynyldimethylsilane was added to a solution of 3.20 g (12.56 mmol) of 2,5-dibromo-3-fluoropyridine, 5.22 mL of triethylamine (37.67 mmol), 59.8 mg (0.31 mmol) of CuI, and 220.3 mg (0.31 mmol) of bis(triphenylphosphane)palladium (II) chloride in 30 mL of absolute THF at 15° C. and the mixture was stirred for 2 hours at RT. 1 mL of tert-butylethynyldimethylsilane was added and the mixture was again stirred for 1 hour at RT. The reaction mixture was evaporated down in vacuo and the residue was taken up in EtOAc. The organic phase was washed with semisaturated aqueous sodium bicarbonate solution, 5% aqueous ammonia, and water, dried over magnesium sulfate, and evaporated down in vacuo. The crude product was purified by column chromatography (silica gel, PE/DCM 9:1). Yield: 1.62 g (41% of theoretical); $C_{13}H_{17}BrFNSi$ (M=314.269); calc.: molpeak (M+H)$^+$: 314/316 (Br); found: molpeak (M+H)$^+$: 314/316 (Br); HPLC-MS: 7.85 minutes (method B).

7.1c. 2-[(tert-butyldimethylsilanyl)ethynyl]-5-(4-chlorophenyl)-3-fluoropyridine 10 mL of MeOH, 10 mL of 2N aqueous sodium carbonate solution, and 94 mg (0.13 mmol) of [1,1'-bis(diphenylphosphine)ferrocene]palladium (II) chloride were added to a solution of 1.61 g (5.14 mmol) of 5-bromo-2-[(tert-butyldimethylsilanyl)ethynyl]-3-fluoropyridine and 0.90 g (5.65 mmol) of 4-chlorophenylboric acid in 30 mL of 1,4-dioxane and the mixture was refluxed for 15 minutes. The reaction mixture was evaporated down in vacuo and diluted with EtOAc. The organic phase was washed with water and semisaturated aqueous sodium bicarbonate solution, dried over sodium sulfate, and evaporated down in vacuo. The residue was purified by column chromatography (silica gel, PE/DCM 1:1). Yield: 1.25 g (70% of theoretical); $C_{19}H_{21}ClFNSi$ (M=345.913); calc.: molpeak (M+H)$^+$: 346/348 (Cl); found: molpeak (M+H)$^+$: 346/348 (Cl); HPLC-MS: 8.83 minutes (method B).

7.1d. 5-(4-chlorophenyl)-2-ethynyl-3-fluoropyridine 1.14 g (3.61 mmol) of TBAF was added at RT to a solution of 1.25 g (3.61 mmol) of 2-[(tert-butyldimethylsilanyl)ethynyl]-5-(4-chlorophenyl)-3-fluoropyridine in 30 mL of DCM and the mixture was stirred for 2 hours. The organic phase was washed with water, dried over sodium sulfate, and evaporated down in vacuo. The residue was stirred with PE, the precipitate was filtered off, washed with PE, and dried in the air. Yield: 0.72 g (86% of theoretical); $C_{13}H_7ClFN$ (M=231.653); calc.: molpeak (M+H)$^+$: 232/234 (Cl); found: molpeak (M+H)$^+$: 232/234 (Cl); HPLC-MS: 5.81 minutes (method B).

7.1e. 2-{4-[5-(4-chlorophenyl)-3-fluoropyridin-2-ylethynyl]phenoxy}ethanol

Under an argon atmosphere 14.8 mg (0.078 mmol) of CuI was added to a solution of 0.82 g (3.11 mmol) of 2-(4-iodo-2-methylphenoxy)ethanol, 0.72 g (2.11 mmol) of 5-(4-chlorophenyl)-2-ethynyl-3-fluoropyridine, 57 mg (0.078 mmol) of [1,1'-bis(diphenylphosphine)ferrocene]palladium (II) chloride, and 0.86 mL (6.22 mmol) of triethylamine in 20 mL of THF and the mixture was stirred for 16 hours at RT. The reaction mixture was combined with EtOAc, and the precipitate was filtered off and washed with EtOAc. The filtrate and the organic washing solutions were washed with 5% aqueous ammonia and water, dried over magnesium sulfate and evaporated down in vacuo. The crude product was purified by column chromatography (silica gel, PE/EtOAc 1:1). Yield: 0.20 g (18% of theoretical); $C_{21}H_{15}ClFNO_2$ (M=367.800); calc.: molpeak (M+H)$^+$: 368/370 (Cl); found: molpeak (M+H)$^+$: 368/370 (Cl); HPLC-MS: 5.94 minutes (method B).

7.1f. 2-{4-[5-(4-chlorophenyl)-3-fluoropyridin-2-ylethynyl]phenoxy}ethyl methanesulfonate At 0° C., 63 µL (0.816 mmol) of methanesulfonyl chloride was added dropwise to a solution of 0.20 g (0.544 mmol) of 2-{4-[5-(4-chlorophenyl)-3-fluoropyridin-2-ylethynyl]phenoxy}ethanol and 0.11 mL (0.816 mmol) of triethylamine in 10 mL of DCM and the mixture was stirred for 16 hours at RT. A further 0.11 mL (0.816 mmol) of triethylamine and 63 µL (0.816 mmol) of methanesulfonyl chloride were added and the mixture was stirred for 8 hours. The reaction mixture was diluted with DCM, and the organic phase was washed with water and dilute aqueous sodium bicarbonate solution, dried over magnesium sulfate, and evaporated down in vacuo. Yield: 0.24 g (99% of theoretical); $C_{22}H_{17}ClFNO_4S$ (M=445.892); calc.: molpeak (M+H)$^+$: 446/448 (Cl); found: molpeak (M+H)$^+$: 446/448 (Cl); HPLC-MS: 6.19 minutes (method B).

7.1g. [(S)-1-(2-{4-[5-(4-chlorophenyl)-3-fluoropyridin-2-ylethynyl]phenoxy}ethyl)pyrrolidin-2-yl]methanol The product was obtained analogously to Example 1.1 g starting from 2-{4-[5-(4-chlorophenyl)-3-fluoropyridin-2-ylethynyl]phenoxy}ethyl methanesulfonate (Example 7.1f) and (S)-1-pyrrolidin-2-ylmethanol. Yield: 35 mg (43% of theoretical); $C_{26}H_{24}ClFN_2O_2$ (M=450.932); calc.: molpeak (M+H)$^+$: 451/453 (Cl); found: molpeak (M+H)$^+$: 451/453 (Cl); HPLC-MS: 4.91 minutes (method B).

The following Examples were prepared analogously starting from 2-{4-[5-(4-chlorophenyl)-3-fluoropyridin-2-ylethynyl]phenoxy}ethyl methanesulfonate (Example 7.1f).

| Example | R | Yield (%) | empirical formula | mass spectrum | retention time HPLC in minutes (method) |
|---|---|---|---|---|---|
| 7.2 | 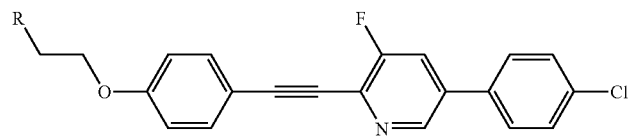 | 38 | $C_{24}H_{20}ClFN_2O$ | 407/409 [M + H]$^+$ | 7.33 (F) |

-continued

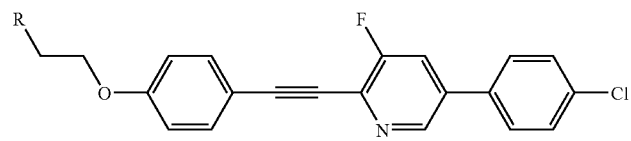

| Example | R | Yield (%) | empirical formula | mass spectrum | retention time HPLC in minutes (method) |
|---|---|---|---|---|---|
| 7.3 | (S)-2-(methoxymethyl)pyrrolidinyl | 75 | C$_{27}$H$_{26}$ClFN$_2$O$_2$ | 465/467 [M + H]$^+$ | 4.69 (D) |
| 7.4 | 3-hydroxy-8-azabicyclo group | 76 | C$_{28}$H$_{26}$ClFN$_2$O$_2$ | 477/479 [M + H]$^+$ | 4.54 (D) |
| 7.5 | 4-(hydroxymethyl)piperidinyl | 62 | C$_{27}$H$_{26}$ClFN$_2$O$_2$ | 465/467 [M + H]$^+$ | 4.42 (D) |
| 7.6 | 3-hydroxypiperidinyl | 82 | C$_{26}$H$_{24}$ClFN$_2$O$_2$ | 451/453 [M + H]$^+$ | 4.43 (D) |
| 7.7 | 3,4-dihydroxy-4-methylpiperidinyl | 73 | C$_{27}$H$_{26}$ClFN$_2$O$_3$ | 481/483 [M + H]$^+$ | 5.24 (D) |
| 7.8 | 4-hydroxy-4-(trifluoromethyl)piperidinyl | 60 | C$_{27}$H$_{23}$ClF$_4$N$_2$O$_2$ | 519/521 [M + H]$^+$ | 5.78 (D) |
| 7.9 | 2-(1-hydroxycyclopropyl)pyrrolidinyl | 19 | C$_{28}$H$_{26}$ClFN$_2$O$_2$ | 477/479 [M + H]$^+$ | 5.55 (D) |

EXAMPLE 8.1

[(S)-1-(2-{4-[5-(4-chlorophenyl)-3-fluoropyridin-2-ylethynyl]-2-methylphenoxy}ethyl)pyrrolidin-2-yl]methanol

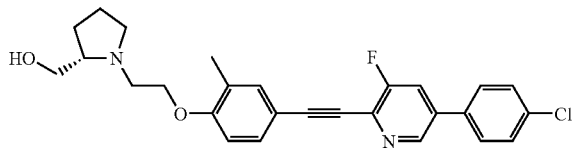

8.1a. 2-(4-iodo-2-methylphenoxy)ethanol

The product was prepared analogously to Example 1.1a. Yield: 11.4 g (96% of theoretical); $C_9H_{11}IO_2$ (M=278.087); $R_f$ value: 0.40 (silica gel, PE/EtOAc 3:2).

8.1b. 2-{4-[5-(4-chlorophenyl)-3-fluoropyridin-2-ylethynyl]-2-methylphenoxy}ethanol The product was obtained analogously to Example 7.1e starting from 2-(4-iodo-2-methylphenoxy)ethanol and 5-(4-chlorophenyl)-2-ethynyl-3-fluoropyridine. Yield: 1.40 g (68% of theoretical); $C_{22}H_{17}ClFNO_2$ (M=381.827); calc.: molpeak (M+H)$^+$: 382/384 (Cl); found: molpeak (M+H)$^+$: 382/384 (Cl); HPLC-MS: 6.29 minutes (method B).

8.1c. 2-{4-[5-(4-chlorophenyl)-3-fluoropyridin-2-ylethynyl]-2-methylphenoxy}ethyl methanesulfonate The product was obtained analogously to Example 7.1f starting from 2-{4-[5-(4-chlorophenyl)-3-fluoropyridin-2-ylethynyl]-2-methylphenoxy}ethanol. Yield: 0.77 g (46% of theoretical); $C_{23}H_{19}ClFNO_4S$ (M=459.918); calc.: molpeak (M+H)$^+$: 460/462 (Cl); found: molpeak (M+H)$^+$: 460/462 (Cl); HPLC-MS: 6.51 minutes (method B).

8.1d. [(S)-1-(2-{4-[5-(4-chlorophenyl)-3-fluoropyridin-2-ylethynyl]-2-methylphenoxy}ethyl)pyrrolidin-2-yl]methanol The product was obtained analogously to Example 7.1g starting from 2-{4-[5-(4-chlorophenyl)-3-fluoropyridin-2-ylethynyl]-2-methylphenoxy}ethyl methanesulfonate and (S)-1-pyrrolidin-2-ylmethanol. Yield: 36 mg (59% of theoretical); $C_{27}H_{26}ClFN_2O_2$ (M=464.959); calc.: molpeak (M+H)$^+$: 465/467 (Cl); found: molpeak (M+H)$^+$: 465/467 (Cl); HPLC-MS: 5.60 minutes (method D).

The following Examples were prepared analogously starting from 2-{4-[5-(4-chlorophenyl)-3-fluoropyridin-2-ylethynyl]-2-methylphenoxy}ethyl methanesulfonate (Example 8.1c).

| Example | R | Yield (%) | empirical formula | mass spectrum | retention time HPLC in minutes (method) |
|---|---|---|---|---|---|
| 8.2 | (S)-2-(methoxymethyl)pyrrolidin-1-yl | 74 | $C_{28}H_{28}ClFN_2O_2$ | 479/481 [M + H]$^+$ | 5.83 (D) |
| 8.3 | 4-methylpiperidin-1-yl | 70 | $C_{28}H_{28}ClFN_2O$ | 463/465 [M + H]$^+$ | 6.01 (D) |
| 8.4 | 3-hydroxy-8-azabicyclo[3.2.1]octan-8-yl | 69 | $C_{29}H_{28}ClFN_2O_2$ | 491/493 [M + H]$^+$ | 5.66 (method D) |

-continued

| Example | R | Yield (%) | empirical formula | mass spectrum | retention time HPLC in minutes (method) |
|---|---|---|---|---|---|
| 8.5 | 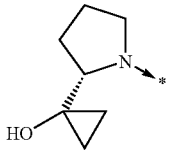 | 34 | $C_{29}H_{28}ClFN_2O_2$ | 491/493 $[M + H]^+$ | 5.79 (method D) |
| 8.6 | 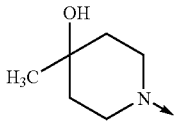 | 78 | $C_{28}H_{28}ClFN_2O_2$ | 479/481 $[M + H]^+$ | 5.60 (method D) |

EXAMPLE 9.1

[(S)-1-(2-{2-bromo-4-[5-(4-chlorophenyl)-3-fluoropyridin-2-ylethynyl]phenoxy}ethyl)pyrrolidin-2-yl]methanol

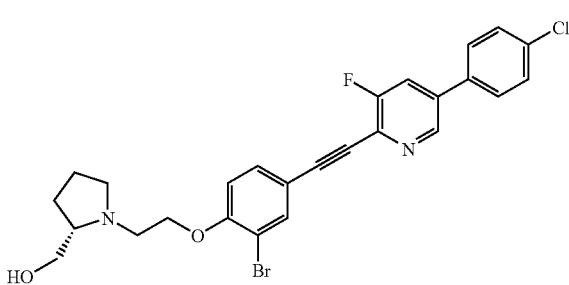

9.1a. 2-(2-bromo-4-iodophenoxy)ethanol

The product was obtained analogously to Example 1.1a. Yield: 18.5 g (52% of theoretical); $C_8H_8BrIO_2$ (M=342.956); $R_f$ value: 0.18 (silica gel, PE/EtOAc 4:1).

9.1b. 2-{2-bromo-4-[5-(4-chlorophenyl)-3-fluoropyridin-2-ylethynyl]phenoxy}ethanol The product was prepared analogously to Example 7.1e starting from 2-(2-bromo-4-iodophenoxy)ethanol and 5-(4-chlorophenyl)-2-ethynyl-3-fluoropyridine. Yield: 1.60 g (82% of theoretical); $C_{21}H_{14}BrClFNO_2$ (M=446.697); calc.: molpeak $(M+H)^+$: 446/448/450 (BrCl); found: molpeak $(M+H)^+$: 446/448/450 (BrCl); HPLC-MS: 6.38 minutes (method B).

9.1c. 2-{2-bromo-4-[5-(4-chlorophenyl)-3-fluoropyridin-2-ylethynyl]phenoxy}ethyl methanesulfonate The product was prepared analogously to Example 7.1f starting from 2-{2-bromo-4-[5-(4-chlorophenyl)-3-fluoropyridin-2-ylethynyl]phenoxy}ethanol. Yield: 1.00 g (53% of theoretical); $C_{22}H_{16}BrClFNO_4S$ (M=524.788); calc.: molpeak $(M+H)^+$: 524/526/528 (BrCl); found: molpeak $(M+H)^+$: 524/526/528 (BrCl); HPLC-MS: 6.58 minutes (method B).

9.1d. [(S)-1-(2-{2-bromo-4-[5-(4-chlorophenyl)-3-fluoropyridin-2-ylethynyl]phenoxy}ethyl)pyrrolidin-2-yl]methanol The product was obtained analogously to Example 7.1g starting from 2-{2-bromo-4-[5-(4-chlorophenyl)-3-fluoropyridin-2-ylethynyl]phenoxy}ethyl methanesulfonate and (S)-1-pyrrolidin-2-ylmethanol. Yield: 37 mg (61% of theoretical); $C_{26}H_{23}BrClFN_2O_2$ (M=529.828); calc.: molpeak $(M+H)^+$: 529/531/533 (BrCl); found: molpeak $(M+H)^+$: 529/531/533 (BrCl); HPLC-MS: 5.69 minutes (method D).

The following Examples were prepared analogously starting from 2-{2-bromo-4-[5-(4-chlorophenyl)-3-fluoropyridin-2-ylethynyl]phenoxy}ethyl methanesulfonate (Example 9.1c).

| Example | R | yield (%) | empirical formula | mass spectrum | retention time HPLC in minutes (method) |
|---|---|---|---|---|---|
| 9.2 | (S)-2-(hydroxycyclopropyl)pyrrolidin-1-yl | 17 | $C_{28}H_{25}BrClFN_2O_2$ | 555/557/559 $[M+H]^+$ | 5.88 (D) |
| 9.3 | (S)-2-(methoxymethyl)pyrrolidin-1-yl | 63 | $C_{27}H_{25}BrClFN_2O_2$ | 543/545/547 $[M+H]^+$ | 6.00 (D) |
| 9.4 | 4-hydroxy-4-methylpiperidin-1-yl | 64 | $C_{27}H_{25}BrClFN_2O_2$ | 543/545/547 $[M+H]^+$ | 5.68 (D) |
| 9.5 | 4-methylpiperidin-1-yl | 55 | $C_{27}H_{25}BrClFN_2O$ | 527/529/531 $[M+H]^+$ | 6.12 (D) |
| 9.6 | 3-hydroxy-8-azabicyclo[3.2.1]octan-8-yl | 69 | $C_{28}H_{25}BrClFN_2O_2$ | 555/557/559 $[M+H]^+$ | 5.77 (D) |

EXAMPLE 10.1

5-[5-(4-chlorophenyl)pyridin-2-ylethynyl]-1-[2-(4-methylpiperidin-1-yl)ethyl]-1H-indazole

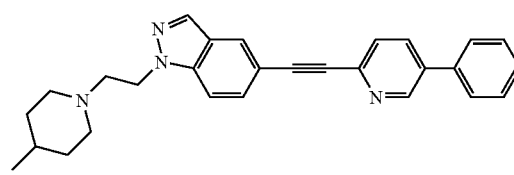

10.1a. 2-(5-iodoindazol-1-yl)ethanol

The product was prepared analogously to Example 1.1a. Yield: 1.70 g (42% of theoretical); $C_9H_9IN_2O$ (M=288.085); calc.: molpeak $(M+H)^+$: 289; found: molpeak $(M+H)^+$: 289.

10.1b. 2-{5-[5-(4-chlorophenyl)pyridin-2-ylethynyl]indazol-1-yl}ethanol

The product was prepared analogously to Example 7.1e starting from 2-(5-iodoindazol-1-yl)ethanol and 5-(4-chlorophenyl)-2-ethynylpyridine. Yield: 1.60 g (73% of theoretical); $C_{22}H_{16}ClN_3O$ (M=373.835); calc.: molpeak $(M+H)^+$: 374/376 (Cl); found: molpeak $(M+H)^+$: 374/376 (Cl).

10.1c. 2-{5-[5-(4-chlorophenyl)pyridin-2-ylethynyl]indazol-1-yl}ethyl methanesulfonate The product was prepared analogously to Example 7.1f starting from 2-{5-[5-(4-chlorophenyl)pyridin-2-ylethynyl]indazol-1-yl}ethanol. Yield: 1.80 g (77% of theoretical); $C_{23}H_{18}ClN_3O_3S$ (M=451.926); calc.: molpeak $(M+H)^+$: 452/454 (Cl); found: molpeak $(M+H)^+$: 452/454 (Cl); HPLC-MS: 5.87 minutes (method B).

10.1d. 5-[5-(4-chlorophenyl)pyridin-2-ylethynyl]-1-[2-(4-methylpiperidin-1-yl)ethyl]-1H-indazole The product was obtained analogously to Example 7.1g starting from 2-{5-[5-(4-chlorophenyl)pyridin-2-ylethynyl]indazol-1-yl}ethyl methanesulfonate and 4-methylpiperidine. Yield: 78 mg (78% of theoretical); $C_{28}H_{27}ClN_4$ (M=454.994); calc.: molpeak (M+H)$^+$: 455/457 (Cl); found: molpeak (M+H)$^+$: 455/457 (Cl); HPLC-MS: 5.53 minutes (method D).

The following Examples were prepared analogously starting from 2-{5-[5-(4-chlorophenyl)pyridin-2-ylethynyl]indazol-1-yl}ethyl methanesulfonate (Example 10.1c).

of N,N'-dimethylethane-1,2-diamine was added and the mixture was stirred for 8 hours at 110° C. The reaction mixture was cooled to RT, acidified with 12% aqueous HCl, and stirred for 30 minutes. The aqueous phase was exhaustively extracted with EtOAc, and the organic phase was washed with dilute aqueous ammonia solution and water, dried over magnesium sulfate, and evaporated down in vacuo. Yield: 9.78 g

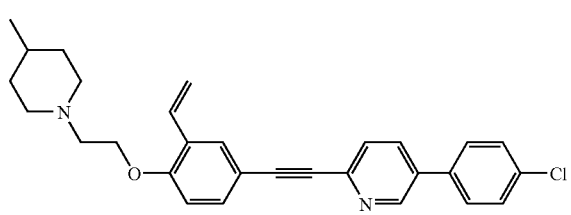

| Example | R | Yield (%) | empirical formula | mass spectrum | retention time HPLC in minutes (method) |
|---|---|---|---|---|---|
| 10.2 | (2-hydroxymethylpyrrolidinyl) | 92 | $C_{27}H_{25}ClN_4O$ | 457/459 [M + H]$^+$ | 5.16 (D) |
| 10.3 | (4-hydroxy-4-methylpiperidinyl) | 77 | $C_{28}H_{27}ClN_4O$ | 470/472 [M + H]$^+$ | 5.17 (D) |
| 10.4 | (2,6-dimethylpiperidinyl) | 35 | $C_{29}H_{29}ClN_4$ | 469/471 [M + H]$^+$ | 5.54 (D) |

EXAMPLE 11.1

5-(4-chlorophenyl)-2-{4-[2-(4-methylpiperidin-1-yl)ethoxy]-3-vinylphenylethynyl}pyridine

11.1a. 2-(2-hydroxyethoxy)-5-iodobenzaldehyde

Under an argon atmosphere 0.91 g (4.80 mmol) of CuI, 14.37 g (95.89 mmol) of NaI, and 6.13 mL (57.53 mmol) of N,N-dimethylethane-1,2-diamine were added to a solution of 11.75 g (47.945 mmol) of 5-bromo-2-(2-hydroxyethoxy)benzaldehyde in 50 mL of 1,4-dioxane and the mixture was stirred for 16 hours at 110° C. Another 6.13 mL (57.53 mmol) (52% of theoretical); $C_9H_9IO_3$ (M=292.070); calc.: molpeak (M+H)$^+$: 292; found: molpeak (M+H)$^+$: 292.

11.1b. 2-(4-iodo-2-vinylphenoxy)ethanol

Under an argon atmosphere 6.85 mL (17.12 mmol) of n-BuLi (2.5 M in hexane) was added to a solution of 6.36 g (17.80 mmol) of methyltriphenylphosphonium bromide in absolute THF at 0° C. and the mixture was stirred for 15 minutes at 0° C. 2.00 g (6.85 mmol) of 5-bromo-2-(2-hydroxyethoxy)benzaldehyde was added and the mixture was stirred for 16 hours at RT.

Saturated aqueous ammonium chloride solution was added and the aqueous phase was exhaustively extracted with EtOAc. The crude product was purified by column chromatography (silica gel, PE/EtOAc 3:2). Yield: 0.53 g (27% of theoretical); $C_{10}H_{11}IO_2$ (M=290.098); calc.: molpeak (M+H)$^+$: 291; found: molpeak (M+H)$^+$: 291; $R_f$ value: 0.23 (silica gel, PE/EtOAc 3:2).

11.1c. 2-{4-[5-(4-chlorophenyl)pyridin-2-ylethynyl]-2-vinylphenoxy}ethanol

The product was obtained analogously to Example 7.1e starting from 2-(4-iodo-2-vinylphenoxy)ethanol and 5-(4-chlorophenyl)-2-ethynylpyridine. Yield: 0.66 g (96% of theoretical); $C_{23}H_{18}ClNO_2$ (M=375.847); calc.: molpeak (M+H)⁺: 376/378 (Cl); found: molpeak (M+H)⁺: 376/378 (Cl); HPLC-MS: 6.21 minutes (method B).

11.1d. ethyl methanesulfonate 2-{4-[5-(4-chlorophenyl)pyridin-2-ylethynyl]-2-vinylphenoxy}ethyl ester The product was obtained analogously to Example 7.1f starting from 2-{4-[5-(4-chlorophenyl)pyridin-2-ylethynyl]-2-vinylphenoxy}ethanol. Yield: 0.23 g (29% of theoretical); $C_{24}H_{20}ClNO_4S$ (M=453.939); calc.: molpeak (M+H)⁺: 454/456 (Cl); found: molpeak (M+H)⁺: 454/456 (Cl); HPLC-MS: 6.40 minutes (method B)

11.1e. 5-(4-chlorophenyl)-2-{4-[2-(4-methylpiperidin-1-yl)ethoxy]-3-vinylphenylethynyl}pyridine The product was obtained analogously to Example 7.1g starting from 2-{4-[5-(4-chlorophenyl)pyridin-2-ylethynyl]-2-vinylphenoxy}ethyl methanesulfonate and 4-methylpiperidine. Yield: 40 mg (72% of theoretical); $C_{29}H_{29}ClN_2O$ (M=457.006); calc.: molpeak (M+H)⁺: 457/459 (Cl); found: molpeak (M+H)⁺: 457/459 (Cl); HPLC-MS: 6.06 minutes (method A).

The following Examples were prepared analogously starting from 2-{4-[5-(4-chlorophenyl)pyridin-2-ylethynyl]-2-vinylphenoxy}ethyl methanesulfonate (Example 11.1d).

EXAMPLE 12.1

5-(4-chlorophenyl)-2-{3-isopropenyl-4-[2-(4-methylpiperidin-1-yl)ethoxy]phenylethynyl}pyridine

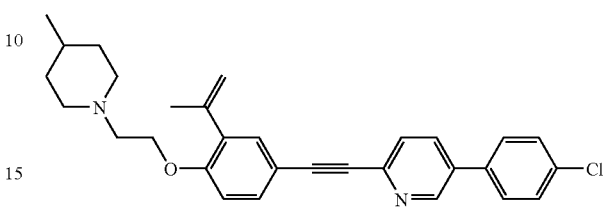

12.1a.
1-[5-bromo-2-(2-hydroxyethoxy)phenyl]ethanone

The product was prepared analogously to Example 1.1a starting from 1-(5-bromo-2-hydroxyphenyl)ethanone. Yield: 7.30 g (30% of theoretical); $C_{10}H_{11}BrO_3$ (M=259.097); calc.: molpeak (M+H)⁺: 259/261 (Br); found: molpeak (M+H)⁺: 259/261 (Br); $R_f$ value: 0.25 (silica gel, PE/EtOAc 1:1).

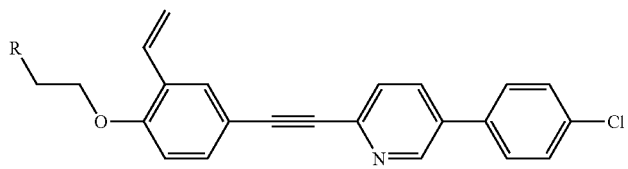

| Example | R | Yield (%) | empirical formula | mass spectrum | retention time HPLC in minutes (method) |
|---|---|---|---|---|---|
| 11.2 | 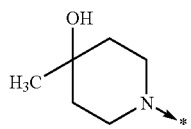 | 35 | $C_{29}H_{29}ClN_2O_2$ | 473/475 [M + H]⁺ | 5.68 (A) |
| 11.3 | 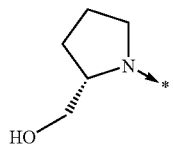 | 72 | $C_{28}H_{27}ClN_2O_2$ | 459/461 [M + H]⁺ | 5.67 (A) |
| 11.4 | 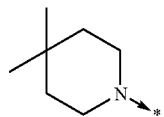 | 16 | $C_{30}H_{31}ClN_2O$ | 471/473 [M + H]⁺ | 6.64 (A) |

12.1b.
1-[2-(2-hydroxyethoxy)-5-iodophenyl]ethanone

The product was prepared analogously to Example 11.1a starting from 1-[5-bromo-2-(2-hydroxyethoxy)phenyl]ethanone. Yield: 7.50 g (87% of theoretical); $C_{10}H_{11}IO_3$ (M=306.097); calc.: molpeak $(M+H)^+$: 307; found: molpeak $(M+H)^+$: 307; HPLC-MS: 4.79 minutes (method B).

12.1c. 2-(4-iodo-2-isopropenylphenoxy)ethanol

The product was prepared analogously to Example 11.1b starting from 1-[2-(2-hydroxyethoxy)-5-iodophenyl]ethanone and using potassium tert-butoxide as base. Yield: 2.50 g (43% of theoretical); $C_{11}H_{13}IO_2$ (M=304.124); calc.: molpeak $(M+H)^+$: 305; found: molpeak $(M+H)^+$: 305; HPLC-MS: 5.65 minutes (method B).

12.1d. 2-{4-[5-(4-chlorophenyl)pyridin-2-ylethynyl]-2-isopropenylphenoxy}ethanol The product was prepared analogously to Example 7.1e starting from 2-(4-iodo-2-isopropenylphenoxy)ethanol and 5-(4-chlorophenyl)-2-ethynylpyridine. Yield: 1.00 g (60% of theoretical); $C_{24}H_{20}ClNO_2$ (M=389.874); calc.: molpeak $(M+H)^+$: 390/392 (Cl); found: molpeak $(M+H)^+$: 390/392 (Cl); $R_f$ value: 0.30 (silica gel, PE/EtOAc 1:1).

12.1e. 2-{4-[5-(4-chlorophenyl)pyridin-2-ylethynyl]-2-isopropenylphenoxy}ethyl methanesulfonate The product was prepared analogously to Example 7.1f starting from 2-{4-[5-(4-chlorophenyl)pyridin-2-ylethynyl]-2-isopropenylphenoxy}ethanol. Yield: 0.95 g (79% of theoretical); $C_{25}H_{22}ClNO_4S$ (M=467.965); calc.: molpeak $(M+H)^+$: 468/470 (Cl); found: molpeak $(M+H)^+$: 468/470 (Cl); $R_f$ value: 0.95 (silica gel, DCM/MeOH 9:1).

12.1f. 5-(4-chlorophenyl)-2-{3-isopropenyl-4-[2-(4-methylpiperidin-1-yl)ethoxy]phenylethynyl}pyridine The product was prepared analogously to Example 7.1g starting from 2-{4-[5-(4-chlorophenyl)pyridin-2-ylethynyl]-2-isopropenylphenoxy}ethyl methanesulfonate and 4-methylpiperidine. Yield: 53 mg (75% of theoretical); $C_{30}H_{31}ClN_2O$ (M=471.033); calc.: molpeak $(M+H)^+$: 471/473 (Cl); found: molpeak $(M+H)^+$: 471/473 (Cl); HPLC-MS: 6.15 minutes (method D).

The following Examples were prepared analogously starting from 2-{4-[5-(4-chlorophenyl)pyridin-2-ylethynyl]-2-isopropenylphenoxy}ethyl methanesulfonate (Example 12.1f).

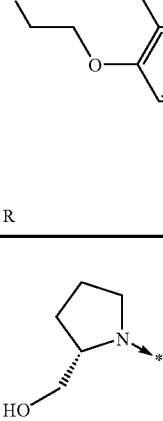

| Example | R | Yield (%) | empirical formula | mass spectrum | retention time HPLC in minutes (method) |
|---|---|---|---|---|---|
| 12.2 | 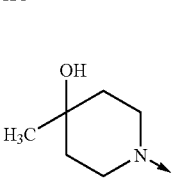 | 83 | $C_{29}H_{29}ClN_2O_2$ | 473/475 $[M+H]^+$ | 5.80 (D) |
| 12.3 | 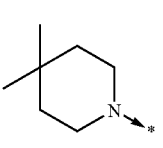 | 82 | $C_{30}H_{31}ClN_2O_2$ | 487/489 $[M+H]^+$ | 5.80 (D) |
| 12.4 | 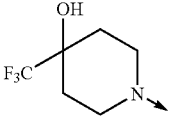 | 30 | $C_{31}H_{33}ClN_2O$ | 485/487 $[M+H]^+$ | 6.30 (D) |
| 12.5 |  | 53 | $C_{33}H_{28}ClF_3N_2O_2$ | 541/543 $[M+H]^+$ | 6.15 (D) |

EXAMPLE 13.1

1-{5-[5-(4-chlorophenyl)pyridin-2-ylethynyl]-2-[2-(4-methylpiperidin-1-yl)ethoxy]phenyl}ethanone

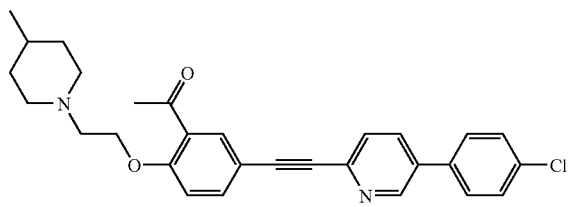

13.1a. 1-[5-[5-(4-chlorophenyl)pyridin-2-ylethynyl]-2-(2-hydroxyethoxy)phenyl]ethanone The product was prepared analogously to Example 7.1e starting from 1-[2-(2-hydroxyethoxy)-5-iodophenyl]ethanone and 5-(4-chlorophenyl)-2-ethynylpyridine. Yield: 0.90 g (70% of theoretical); $C_{23}H_{18}ClNO_3$ (M=391.847); calc.: molpeak $(M+H)^+$: 392/394 (Cl); found: molpeak $(M+H)^+$: 392/394 (Cl); $R_f$ value: 0.55 (silica gel, DCM/MeOH 9:1).

13.1b. 2-{2-acetyl-4-[5-(4-chlorophenyl)pyridin-2-ylethynyl]phenoxy}ethyl methanesulfonate The product was prepared analogously to Example 7.1f starting from 1-[5-[5-(4-chlorophenyl)pyridin-2-ylethynyl]-2-(2-hydroxyethoxy)phenyl]ethanone. Yield: 0.90 g (83% of theoretical); $C_{24}H_{20}ClNO_5S$ (M=469.938); calc.: molpeak $(M+H)^+$: 470/472 (Cl); found: molpeak $(M+H)^+$: 470/472 (Cl); $R_f$ value: 0.65 (silica gel, DCM/MeOH 9:1).

13.1c. 1-{5-[5-(4-chlorophenyl)pyridin-2-ylethynyl]-2-[2-(4-methylpiperidin-1-yl)ethoxy]phenyl}ethanone The product was prepared analogously to Example 7.1g starting from 2-{2-acetyl-4-[5-(4-chlorophenyl)pyridin-2-ylethynyl]phenoxy}ethyl methanesulfonate and 4-methylpiperidine. Yield: 0.40 g (88% of theoretical); $C_{29}H_{29}ClN_2O_2$ (M=473.006); calc.: molpeak $(M+H)^+$: 473/375 (Cl); found: molpeak $(M+H)^+$: 473/475 (Cl); $R_f$ value: 0.30 (silica gel, DCM/MeOH 9:1).

The following Examples were prepared analogously starting from 2-{2-acetyl-4-[5-(4-chlorophenyl)pyridin-2-ylethynyl]phenoxy}ethyl methanesulfonate (Example 13.1b).

| Example | R | Yield (%) | empirical formula | mass spectrum | retention time HPLC in minutes (method) |
|---|---|---|---|---|---|
| 13.2 | (S)-2-(hydroxymethyl)pyrrolidin-1-yl | 54 | $C_{28}H_{27}ClN_2O_3$ | 475/477 $[M+H]^+$ | 4.92 (B) |
| 13.3 | 4-hydroxy-4-methylpiperidin-1-yl | 55 | $C_{29}H_{29}ClN_2O_3$ | 489/491 $[M+H]^+$ | 4.88 (B) |
| 13.4 | 4,4-dimethylpiperidin-1-yl | 30 | $C_{30}H_{31}ClN_2O_3$ | 487/489 $[M+H]^+$ | 5.79 (D) |
| 13.5 | 4-hydroxy-4-(trifluoromethyl)piperidin-1-yl | 60 | $C_{29}H_{26}ClF_3N_2O_3$ | 543/545 $[M+H]^+$ | 5.70 (D) |

EXAMPLE 14.1

5-[5-(4-chlorophenyl)pyridin-2-ylethynyl]-2-[2-(4-methylpiperidin-1-yl)ethoxy]benzaldehyde-O-methyloxime

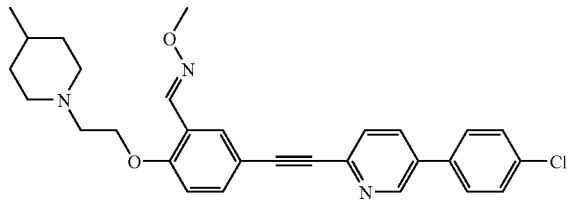

14.1a. 5-[5-(4-chlorophenyl)pyridin-2-ylethynyl]-2-(2-hydroxyethoxy)benzaldehyde The product was prepared analogously to Example 7.1e starting from 2-(2-hydroxyethoxy)-5-iodobenzaldehyde and 5-(4-chlorophenyl)-2-ethynylpyridine. Yield: 5.53 g (86% of theoretical); $C_{22}H_{16}ClNO_3$ (M=377.820); calc.: molpeak $(M+H)^+$: 378/380 (Cl); found: molpeak $(M+H)^+$: 378/380 (Cl); HPLC-MS: 5.79 minutes (method B).

14.1b. 2-{4-[5-(4-chlorophenyl)pyridin-2-ylethynyl]-2-formylphenoxy}ethyl methanesulfonate The product was prepared analogously to Example 7.1f starting from 5-[5-(4-chlorophenyl)pyridin-2-ylethynyl]-2-(2-hydroxyethoxy)benzaldehyde. Yield: 3.40 g (50% of theoretical); $C_{23}H_{18}ClNO_5S$ (M=455.911); calc.: molpeak $(M+H)^+$: 456/458 (Cl); found: molpeak $(M+H)^+$: 456/458 (Cl); HPLC-MS: 6.05 minutes (method B).

14.1c. 5-[5-(4-chlorophenyl)pyridin-2-ylethynyl]-2-[2-(4-methylpiperidin-1-yl)ethoxy]benzaldehyde The product was prepared analogously to Example 7.1g starting from 2-{4-[5-(4-chlorophenyl)pyridin-2-ylethynyl]-2-formylphenoxy}ethyl methanesulfonate and 4-methylpiperidine. Yield: 186 mg (62% of theoretical); $C_{28}H_{27}ClN_2O_2$ (M=458.979); calc.: molpeak $(M+H)^+$: 459/461 (Cl); found: molpeak $(M+H)^+$: 459/461 (Cl); HPLC-MS: 5.45 minutes (method B).

The following intermediate products were prepared analogously starting from 2-{4-[5-(4-chlorophenyl)pyridin-2-ylethynyl]-2-formylphenoxy}ethyl methanesulfonate (Example 14.1b).

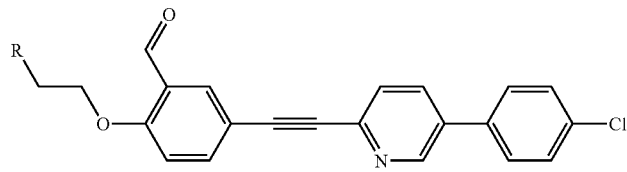

| Example | R | Yield (%) | empirical formula | mass spectrum | retention time HPLC in minutes (method) |
|---|---|---|---|---|---|
| 14.2c | | 86 | $C_{27}H_{25}ClN_2O_3$ | 461/463 $[M+H]^+$ | 7.47 (B) |
| 14.3c | | 66 | $C_{27}H_{25}ClN_2O_3$ | 461/463 $[M+H]^+$ | 4.86 (B) |
| 14.4c | | 92 | $C_{29}H_{29}ClN_2O_2$ | 473/475 $[M+H]^+$ | 5.48 (D) |
| 14.5c | | 48 | $C_{29}H_{29}ClN_2O_2$ | 473/475 $[M+H]^+$ | 5.60 (B) |

-continued

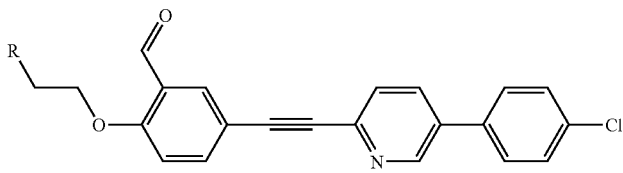

| Example | R | Yield (%) | empirical formula | mass spectrum | retention time HPLC in minutes (method) |
|---|---|---|---|---|---|
| 14.6c | pyrrolidin-1-yl | 37 | $C_{26}H_{23}ClN_2O_2$ | 431/433 $[M+H]^+$ | 4.90 (B) |

14.1d. 5-[5-(4-chlorophenyl)pyridin-2-ylethynyl]-2-[2-(4-methylpiperidin-1-yl)ethoxy]benzaldehyde-O-methyloxime 22 mg (0.257 mmol) of O-methylhydroxylamine hydrochloride and 36 μL (0.257 mmol) of triethylamine were added to a solution of 85 mg (0.185 mmol) of 5-[5-(4-chlorophenyl)pyridin-2-ylethynyl]-2-[2-(4-methylpiperidin-1-yl)ethoxy]benzaldehyde (Example 14.1c) in 2 mL of acetonitrile/EtOH (1:1) and the mixture was stirred for 16 hours at 75° C. The reaction mixture was diluted with water and the aqueous phase exhaustively extracted with DCM. The combined organic phases were dried over magnesium sulfate and evaporated down in vacuo. Yield: 40 mg (44% of theoretical); $C_{29}H_{30}ClNO_3O_2$ (M=488.020); calc.: molpeak $(M+H)^+$: 488/490 (Cl); found: molpeak $(M+H)^+$: 488/490 (Cl); HPLC-MS: 6.04 minutes (method A).

The following Examples were prepared analogously.

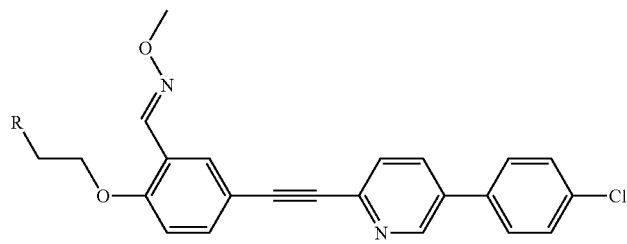

| Example | R | Yield (%) | empirical formula | mass spectrum | retention time HPLC in minutes (method) |
|---|---|---|---|---|---|
| 14.2 (from 14.2c) | (2-hydroxymethyl)pyrrolidin-1-yl | 92 | $C_{28}H_{28}ClN_3O_3$ | 490/492 $[M+H]^+$ | 5.04 (A) |
| 14.3 (from 14.3c) | 4-hydroxypiperidin-1-yl | 14 | $C_{28}H_{28}ClN_3O_3$ | 490/492 $[M+H]^+$ | 5.60 (A) |
| 14.4 (from 14.4c) | 2,6-dimethylpiperidin-1-yl | 26 | $C_{30}H_{32}ClN_3O_2$ | 502/504 $[M+H]^+$ | 6.04 (A) |

-continued

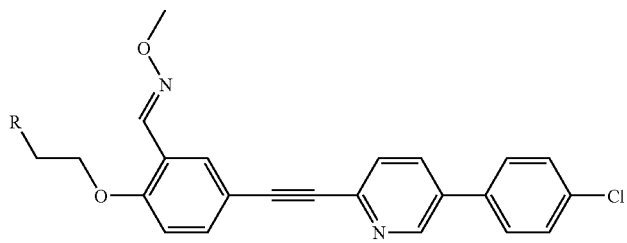

| Example | R | Yield (%) | empirical formula | mass spectrum | retention time HPLC in minutes (method) |
|---|---|---|---|---|---|
| 14.5 (from 14.5c) | 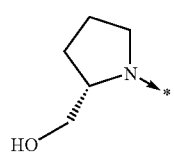 | 31 | $C_{30}H_{32}ClN_3O_2$ | 502/504 $[M + H]^+$ | 6.19 (A) |

EXAMPLE 15.1

5-[5-(4-chlorophenyl)pyridin-2-ylethynyl]-2-[2-(4-methylpiperidin-1-yl)ethoxy]benzaldehydeoxime

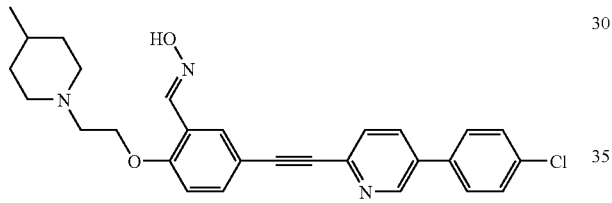

The product was obtained analogously to Example 14.1d starting from 5-[5-(4-chlorophenyl)pyridin-2-ylethynyl]-2-[2-(4-methylpiperidin-1-yl)ethoxy]benzaldehyde (Example 14.1c) and hydroxylamine. Yield: 40 mg (46% of theoretical); $C_{28}H_{28}ClN_3O_2$ (M=473.994); calc.: molpeak $(M+H)^+$: 474/476 (Cl); found: molpeak $(M+H)^+$: 474/476 (Cl); HPLC-MS: 5.68 minutes (method A).

The following Examples were prepared analogously.

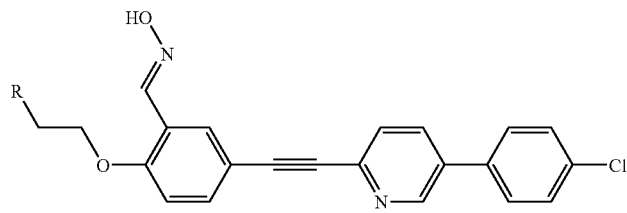

| Example | R | Yield (%) | empirical formula | mass spectrum | retention time HPLC in minutes (method) |
|---|---|---|---|---|---|
| 15.2 (from 14.2c) | | 54 | $C_{27}H_{26}ClN_3O_3$ | 476/478 $[M + H]^+$ | 6.31 (A) |

-continued

| Example | R | Yield (%) | empirical formula | mass spectrum | retention time HPLC in minutes (method) |
|---|---|---|---|---|---|
| 15.3 (from 14.3c) | HO-[piperidin-4-yl] | 10 | C$_{27}$H$_{26}$ClN$_3$O$_3$ | 476/478 [M + H]$^+$ | 5.23 (A) |
| 15.4 (from 14.4c) | 2,6-dimethylpiperidin-1-yl | 30 | C$_{29}$H$_{30}$ClN$_3$O$_2$ | 488/490 [M + H]$^+$ | 5.67 (A) |
| 15.5 (from 14.5c) | 3,5-dimethylpiperidin-1-yl | 28 | C$_{29}$H$_{30}$ClN$_3$O$_2$ | 488/490 [M + H]$^+$ | 5.85 (A) |

EXAMPLE 16.1

3-bromo-5-(4-chlorophenyl)-2-{4-[2-(4-methylpiperidin-1-yl)ethoxy]phenylethynyl}pyridine

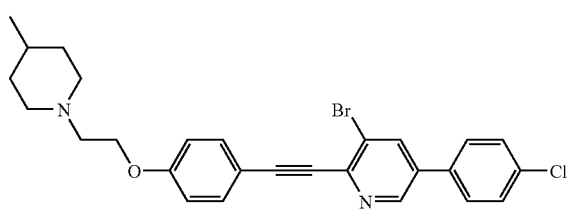

16.1a. 5-(4-chlorophenyl)-3-nitropyridin-2-ol

Under an argon atmosphere a mixture of 22.10 g (100.91 mmol) of 5-bromo-3-nitropyridin-2-ol, 23.46 g (150.00 mmol) of 4-chlorophenylboric acid, 0.73 g (1.00 mmol) of bis(diphenylphosphine)ferrocene]palladium (II) chloride, and 200 mL of 2N aqueous sodium carbonate solution in 400 mL of acetone was stirred for 16 hours at 60° C. and then evaporated down in vacuo. The aqueous phase was neutralized with 160 mL of 1M citric acid solution and exhaustively extracted with EtOAc and a little MeOH. The combined organic phases were dried over magnesium sulfate and evaporated down in vacuo. The residue was triturated with a little EtOAc, the precipitate was filtered off and dried. Yield: 9.70 g (22% of theoretical); C$_{11}$H$_7$ClN$_2$O$_3$ (M=250.638); calc.: molpeak (M−H)$^-$: 249/251 (Cl); found: molpeak (M−H)$^-$: 249/251 (Cl); HPLC-MS: 6.83 minutes (method A).

16.1b. 2-bromo-5-(4-chlorophenyl)-3-nitropyridine 13.20 g (93.00 mmol) of phosphorus pentoxide were added to a solution of 9.70 g (38.70 mmol) of 5-(4-chlorophenyl)-3-nitropyridin-2-ol and 14.51 g (45.00 mmol) of tetrabutylammonium bromide in 100 mL of toluene and the mixture was stirred for 1.5 hours at 95° C. The organic phase was decanted off and the residue was washed 2× with toluene. The combined organic phases were washed with sat. aqueous sodium bicarbonate solution, dried over magnesium sulfate, and evaporated down in vacuo. Yield: 4.90 g (40% of theoretical); C$_{11}$H$_6$BrClN$_2$O$_2$ (M=313.534); calc.: molpeak (M+H)$^+$: 313/315/317 (BrCl); found: molpeak (M+H)$^+$: 313/315/317 (BrCl); HPLC-MS: 6.01 minutes (method B).

16.1c. 2-bromo-5-(4-chlorophenyl)pyridin-3-ylamine

A mixture of 5.60 g (17.861 mmol) of 2-bromo-5-(4-chlorophenyl)-3-nitropyridine, 20.31 g (90.00 mmol) of tin (II) chloride, and 18.90 g (225.00 mmol) of sodium bicarbonate in 300 mL of glacial acetic acid was refluxed for 30 hours, then cooled to RT and filtered. The filtrate was evaporated down in vacuo and triturated with a little DCM. The precipitate was filtered off and dried in vacuo. Yield: 3.50 g (69% of theoretical); C$_{11}$H$_8$BrClN$_2$ (M=283.551); calc.: molpeak (M+H)⁺: 283/285/287 (BrCl); found: molpeak (M+H)⁺: 283/285/287 (BrCl); HPLC-MS: 5.45 minutes (method B).

16.1d. 2,3-dibromo-5-(4-chlorophenyl)pyridine

A solution of 0.33 g (4.85 mmol) of sodium nitrite in 1.9 mL of water was added at 0° C. with vigorous stirring to a suspension of 1.25 g (4.41 mmol) of 2-bromo-5-(4-chlorophenyl)pyridin-3-ylamine in 9.90 mL (88.16 mmol) of 48% aqueous HBr and 9.90 mL of water and stirred for a further 10 minutes at 0° C. Subsequently a solution of 0.95 g (6.61 mmol) of CuBr in 3.47 mL of 48% aqueous HBr was added and the mixture was stirred for I hour at 60° C. The reaction mixture was diluted with water and exhaustively extracted with EtOAc. The combined organic extracts were washed with saturated aqueous sodium bicarbonate solution and water, dried over magnesium sulfate, and evaporated down in vacuo. The residue was purified by column chromatography (silica gel, PE/DCM 1:1). Yield: 1.00 g (65% of theoretical); $C_{11}H_6Br_2ClN$ (M=347.433); calc.: molpeak (M+H)⁺:346/348/350/352 (2BrCl); found: molpeak (M+H)⁺: 346/348/350/352 (2BrCl).

16.1e. 3-bromo-5-(4-chlorophenyl)-2-trimethylsilanylethynylpyridine

The product was prepared analogously to Example 7.1b starting from 2,3-dibromo-5-(4-chlorophenyl)pyridine and trimethylsilylacetylene. Yield: 1.00 g (95% of theoretical); $C_{16}H_{15}BrClNSi$ (M=364.739); calc.: molpeak (M+H)⁺: 364/366/368 (BrCl); found: molpeak (M+H)⁺: 364/366/368 (BrCl).

16.1f 3-bromo-5-(4-chlorophenyl)-2-ethynylpyridine

The product was prepared analogously to Example 7.1d starting from 3-bromo-5-(4-chlorophenyl)-2-trimethylsilanylethynylpyridine. Yield: 0.44 g (55% of theoretical); $C_{13}H_7BrClN$ (M=292.558); calc.: molpeak (M+H)⁺: 292/294/296 (BrCl); found: molpeak (M+H)⁺: 292/294/296 (BrCl); HPLC-MS: 6.21 minutes (method B).

16.1g. 2-{4-[3-bromo-5-(4-chlorophenyl)pyridin-2-ylethynyl]phenoxy}ethanol

The product was prepared analogously to Example 7.1e starting from 3-bromo-5-(4-chlorophenyl)-2-ethynylpyridine and 2-(4-iodophenoxy)ethanol. Yield: 0.18 g (28% of theoretical); $C_{21}H_{15}BrClNO_2$ (M=428.706); calc.: molpeak (M+H)⁺: 428/430/432 (BrCl); found: molpeak (M+H)⁺: 428/430/432 (BrCl).

16.1h. methanesulfonate 2-{4-[3-bromo-5-(4-chlorophenyl)pyridin-2-ylethynyl]phenoxy}ethyl The product was obtained analogously to Example 7.1f starting from 2-{4-[3-bromo-5-(4-chlorophenyl)pyridin-2-ylethynyl]phenoxy}ethanol. Yield: 0.17 g (80% of theoretical); $C_{22}H_{17}BrClNO_4S$ (M=506.797); calc.: molpeak (M+H)⁺: 506/508/510 (BrCl); found: molpeak (M+H)⁺: 506/508/510 (BrCl); HPLC-MS: 6.58 minutes (method B).

16.1i. 3-bromo-5-(4-chlorophenyl)-2-{4-[2-(4-methylpiperidin-1-yl)ethoxy]phenylethynyl}pyridine The product was obtained analogously to Example 7.1g starting from 2-{4-[3-bromo-5-(4-chlorophenyl)pyridin-2-ylethynyl]phenoxy}ethyl methanesulfonate and 4-methylpiperidine. Yield: 0.15 g (88% of theoretical); $C_{27}H_{26}BrClN_2O$ (M=509.865); calc.: molpeak (M+H)⁺: 509/511/513 (BrCl); found: molpeak (M+H)⁺: 509/511/513 (BrCl); HPLC-MS: 6.11 minutes (method A).

EXAMPLE 17.1

5-(4-chlorophenyl)-3-methyl-2-{4-[2-(4-methylpiperidin-1-yl)ethoxy]phenylethynyl}pyridine

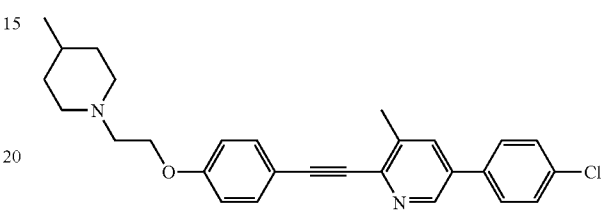

2.5 n-L of 2M aqueous sodium carbonate solution and 15 mg (0.013 mmol) of tetrakis(triphenylphosphane)palladium were added under argon to a suspension of 130 mg (0.255 mmol) of 3-bromo-5-(4-chlorophenyl)-2-{4-[2-(4-methylpiperidin-1-yl)ethoxy]phenylethynyl}pyridine and 18.9 mg (0.306 mmol) of methylboric acid in 5 mL of 1,4-dioxane and the mixture was refluxed for 5 hours. A further 18.9 mg (0.306 mmol) of methylboric acid was added and again the mixture was refluxed for 2 hours. The reaction mixture was exhaustively extracted with EtOAc, the combined organic phases were washed with saturated aqueous sodium bicarbonate solution, dried over magnesium sulfate, and evaporated down in vacuo. The residue was purified by HPLC-MS (Symmetry C18, gradient 0.15% formic acid in water/acetonitrile 10/90→50/50 v/v) and the product fractions were lyophilized. Product fraction 1: Yield: 12 mg (11% of theoretical); $C_{28}H_{29}ClN_2O$ (M=444.995); calc.: molpeak (M+H)⁺: 445/447 (Cl); found: molpeak (M+H)⁺: 445/447 (Cl); HPLC-MS: 4.00 minutes (method E).

EXAMPLE 18.1

3-methyl-2-{4-[2-(4-methylpiperidin-1-yl)ethoxy]phenylethynyl}-5-p-tolylpyridine

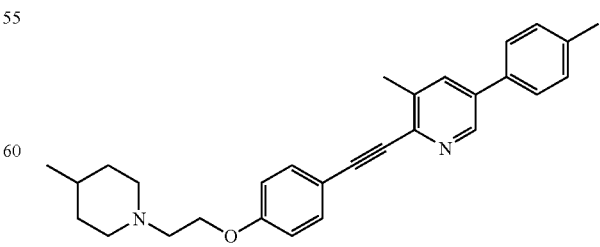

The product was obtained as a by-product in Example 17.1 and was isolated as product fraction 2. Yield: 1.5 mg (1% of theoretical); C$_{29}$H$_{32}$N$_2$O (M=424.577); calc.: molpeak (M+H)$^+$425; found: molpeak (M+H)$^+$: 425; HPLC-MS: 3.73 minutes (method E).

EXAMPLE 19.1

5-(4-chlorophenyl)-2-{4-[2-(4-methylpiperidin-1-yl)ethoxy]phenylethynyl}pyridin-3-ylamine

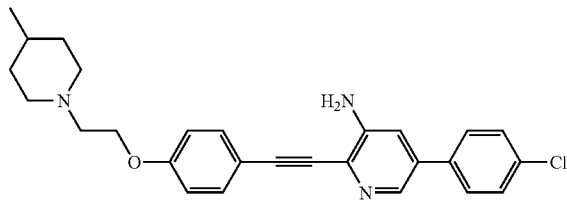

19.1a.
1-[2-(4-iodophenoxy)ethyl]-4-methylpiperidine

A suspension of 1.55 g (52.50 mmol) of 4-iodophenol, 8.50 g (52.57 mmol) of 1-(2-chloroethyl)-4-methylpiperidine, and 14.51 g (105.00 mmol) of potassium carbonate in 200 mL of DMF was stirred for 6 hours at 80° C., the reaction mixture was cooled to RT, filtered, and the filtrate was evaporated down in vacuo. The residue was taken up in EtOAc, and the organic phase was washed with 2M aqueous NaOH solution, dried over magnesium sulfate, and evaporated down in vacuo. The crude product was purified by column chromatography (silica gel, gradient EtOAc/MeOH/sat. aqueous ammonia 100:0:0→95:5:0.5). Yield: 12.90 g (71% of theoretical); C$_{14}$H$_{20}$INO (M=345.219); calc.: molpeak (M+H)$^+$: 346; found: molpeak (M+H)$^+$: 346; R$_f$ value: 0.30 (silica gel, DCM/MeOH/sat. aqueous ammonia 95:5:0.5).

19.1b. 5-(4-chlorophenyl)-2-trimethylsilanylethynylpyridin-3-ylamine

The product was obtained analogously to Example 7.1b starting from 2-bromo-5-(4-chlorophenyl)pyridin-3-ylamine (Example 16.1c) and trimethylsilylacetylene. Yield: 1.09 g (51% of theoretical); C$_{16}$H$_{17}$ClN$_2$Si (M=300.858); calc.: molpeak (M+H)$^+$: 301/303 (Cl); found: molpeak (M+H)$^+$: 301/303 (Cl).

19.1c.
5-(4-chlorophenyl)-2-ethynylpyridin-3-ylamine

The product was prepared analogously to Example 7.1d starting from 5-(4-chlorophenyl)-2-trimethylsilanylethynylpyridin-3-ylamine. Yield: 0.45 (quant. yield); C$_{13}$H$_9$ClN$_2$ (M=228.677); calc.: molpeak (M+H)$^+$: 229/231 (Cl); found: molpeak (M+H)$^+$: 229/231 (Cl); HPLC-MS: 4.93 minutes (method B).

19.1d. 5-(4-chlorophenyl)-2-{4-[2-(4-methylpiperidin-1-yl)ethoxy]phenylethynyl}pyridin-3-ylamine The product was prepared analogously to Example 7.1e starting from 5-(4-chlorophenyl)-2-ethynylpyridin-3-ylamine and 1-[2-(4-iodophenoxy)ethyl]-4-methylpiperidine. Yield: 0.63 (75% of theoretical); C$_{27}$H$_{28}$ClN$_3$O (M=445.984); calc.: molpeak (M+H)$^+$: 446/448 (Cl); found: molpeak (M+H)$^+$: 446/448 (Cl); HPLC-MS: 5.05 minutes (method D).

EXAMPLE 20.1

{4-[5-(4-chlorophenyl)pyridin-2-ylethynyl]-2-methylphenyl}-[2-(4-methylpiperidin-1-yl)ethyl]amine

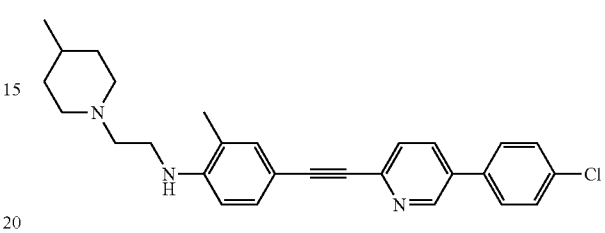

20.1a. (4-bromo-2-methylphenyl)-[2-(4-methylpiperidin-1-yl)ethyl]amine 5.00 g (35.00 mmol) of 2-(4-methylpiperidin-1-yl)ethylamine was added under argon to a mixture of 10.39 g (35.00 mmol) of 4-bromo-1-iodo-2-methylbenzene, 0.33 g (1.75 mmol) of CuI, 30.0 g (141.00 mmol) of potassium phosphate, and 4.34 g (70.00 mmol) of ethylene glycol in 35 mL of isopropanol and the mixture was refluxed for 15 hours. The reaction mixture was evaporated down in vacuo and the residue taken up in EtOAc. The organic phase was washed with 5% aqueous ammonia, dried over magnesium sulfate, and evaporated down in vacuo. The crude product was purified by column chromatography (silica gel, EtOAc). Yield: 1.20 g (11% of theoretical); C$_{15}$H$_{23}$BrN$_2$ (M=311.261); calc.: molpeak (M+H)$^+$: 311/313 (Br); found: molpeak (M+H)$^+$: 311/313 (Br); HPLC-MS: 4.24 minutes (method B).

20.1b. (4-iodo-2-methylphenyl)-[2-(4-methylpiperidin-1-yl)ethyl]amine 73 mg (0.386 mmol) of CuI, 1.16 g (7.71 mmol) of NaI, and N,N'-dimethylethane-1,2-diamine were added under argon to a solution of 1.20 g (3.86 mmol) of (4-bromo-2-methylphenyl)-[2-(4-methylpiperidin-1-yl)ethyl]amine in 3.9 mL of 1,4-dioxane and the mixture was stirred for 20 hours at 110° C. The reaction mixture was cooled to RT and diluted with EtOAc. The organic phase was washed with 10% aqueous ammonia, dried over magnesium sulfate, and evaporated down in vacuo. Yield: 1.22 g (88% of theoretical); C$_{15}$H$_{23}$IN$_2$ (M=358.261); calc.: molpeak (M+H)$^+$: 359; found: molpeak (M+H)$^+$: 359; HPLC-MS: 6.24 minutes (method A).

20.1c. {4-[5-(4-chlorophenyl)pyridin-2-ylethynyl]-2-methylphenyl}-[2-(4-methylpiperidin-1-yl)ethyl]amine The product was prepared analogously to Example 7.1e starting from (4-iodo-2-methylphenyl)-[2-(4-methylpiperidin-1-yl)ethyl]amine and 5-(4-chlorophenyl)-2-ethynylpyridine. Yield: 60 mg (20% of theoretical); C$_{28}$H$_{30}$ClN$_3$ (M=444.011); calc.: molpeak (M+H)$^+$444/446 (Cl); found molpeak (M+H)$^+$: 444/446 (Cl); HPLC-MS: 5.53 minutes (method B).

EXAMPLE 21.1

3-chloro-5-(4-chlorophenyl)-2-{4-[2-(4-methylpiperidin-1-yl)ethoxy]phenylethynyl}pyridine

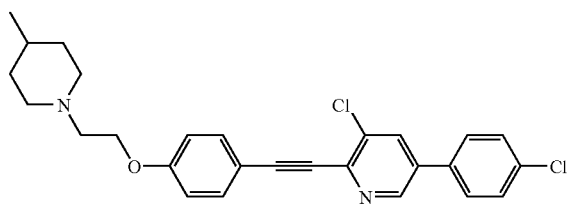

21.1a. 2-bromo-3-chloro-5-(4-chlorophenyl)pyridine

The product was obtained analogously to Example 16.1d starting from 2-bromo-5-(4-chlorophenyl)pyridin-3-ylamine. Yield: 0.54 g (51% of theoretical); $C_{11}H_6BrCl_2N$ (M=302.981); calc.: molpeak (M+H)$^+$: 301/303/305/307 (Br2Cl); found: molpeak (M+H)$^+$: 301/303/305/307 (Br2Cl); HPLC-MS: 6.64 minutes (method B).

21.1b. 3-chloro-5-(4-chlorophenyl)-2-trimethylsilanylethynylpyridine

The product was obtained analogously to Example 7.1b starting from 2-bromo-3-chloro-5-(4-chlorophenyl)pyridine and trimethylsilylacetylene. Yield: 0.57 g (quant. yield); $C_{16}H_{15}Cl_2NSi$ (M=320.288); calc.: molpeak (M+H)$^+$: 320/322/324 (2Cl); found: molpeak (M+H)$^+$: 320/322/324 (2Cl); HPLC-MS: 8.02 minutes (method B).

21.1c. 3-chloro-5-(4-chlorophenyl)-2-ethynylpyridine

The product was obtained analogously to Example 7.1d starting from 3-chloro-5-(4-chlorophenyl)-2-trimethylsilanylethynylpyridine. Yield: 0.40 g (91% of theoretical); $C_{13}H_7Cl_2N$ (M=248.107); calc.: molpeak (M+H)$^+$: 247/249/251 (2Cl); found: molpeak (M+H)$^+$: 247/249/251 (2Cl).

21.1d. 2-{4-[3-chloro-5-(4-chlorophenyl)pyridin-2-ylethynyl]phenoxy}ethanol

The product was prepared analogously to Example 7.1e starting from 3-chloro-5-(4-chlorophenyl)-2-ethynylpyridine and 2-(4-iodophenoxy)ethanol. Yield: 0.48 g (66% of theoretical); $C_{21}H_{15}Cl_2NO_2$ (M=384.255); calc.: molpeak (M+H)$^+$ 384/386/388 (2Cl); found: molpeak (M+H)$^+$: 384/386/388 (2Cl); HPLC-MS: 6.24 minutes (method B).

21.1e. ethyl 2-{4-[3-chloro-5-(4-chlorophenyl)pyridin-2-ylethynyl]phenoxy}-methanesulfonate The product was obtained analogously to Example 7.1f starting from 2-{4-[3-chloro-5-(4-chlorophenyl)pyridin-2-ylethynyl]phenoxy}ethanol. Yield: 0.36 g (73% of theoretical); $C_{22}H_{17}Cl_2NO_4S$ (M=462.346); calc.: molpeak (M+H)$^+$: 462/464/466 (2Cl); found: molpeak (M+H)$^+$: 462/464/466 (2Cl).

21.1f. 3-chloro-5-(4-chlorophenyl)-2-{4-[2-(4-methylpiperidin-1-yl)ethoxy]phenylethynyl}pyridine The product was obtained analogously to Example 7.1g starting from 2-{4-[3-chloro-5-(4-chlorophenyl)pyridin-2-ylethynyl]phenoxy}ethyl methanesulfonate and 4-methylpiperidine. Yield: 70 mg (58% of theoretical); $C_{27}H_{26}Cl_2N_2O$ (M=465.414); calc.: molpeak (M+H)$^+$: 465/467/469 (2Cl); found: molpeak (M+H)$^+$: 465/467/469 (2Cl); HPLC-MS: 5.99 minutes (method D).

The following Examples were prepared analogously starting from 2-{4-[3-chloro-5-(4-chlorophenyl)pyridin-2-ylethynyl]phenoxy}ethyl methanesulfonate (Example 21.1e).

| Example | R | yield (%) | empirical formula | mass spectrum | retention time HPLC in minutes (method) |
|---|---|---|---|---|---|
| 21.2 | (2-hydroxymethyl-pyrrolidinyl) | 41 | $C_{26}H_{24}Cl_2N_2O_2$ | 467/469/471 [M + H]$^+$ | 5.66 (D) |
| 21.3 | (4-hydroxy-4-methyl-piperidinyl) | 72 | $C_{27}H_{26}Cl_2N_2O_2$ | 481/483/485 [M + H]$^+$ | 5.65 (D) |

EXAMPLE 22.1

5-(4-chlorophenyl)-2-[2-(4-methylpiperidin-1-ylmethyl)benzo[b]thiophen-5-ylethynyl]pyridine

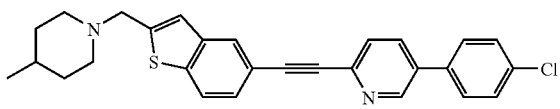

22.1a. methyl 5-iodobenzo[b]thiophen-2-carboxylate

Under an argon atmosphere 0.35 g (1.84 mmol) of CuI, 5.53 g (36.88 mmol) of NaI, and 0.39 mL (3.67 mmol) of N,N'-dimethylethylenediamine were added to a solution of 5.0 g (18.4 mmol) of methyl 5-bromobenzo[b]thiophen-2-carboxylate in 18 mL of 1,4-dioxane and after rinsing again with argon the reaction mixture was heated overnight to 110° C. After cooling, the reaction mixture was combined with 30% aqueous ammonia and water, exhaustively extracted with EtOAc, and the combined organic phases were twice washed with water and dried over magnesium sulfate. After the desiccant and solvent had been eliminated, the residue was triturated with DIPE and MTBE, suction filtered, and dried in the air. Yield: 3.4 g (58% of theoretical); $C_{10}H_7IO_2S$ (M=318.132); calc.: molpeak (M)$^+$: 318; found: molpeak (M)$^+$: 318; HPLC-MS: 6.4 minutes (method B).

22.1b. methyl 5-[5-(4-chlorophenyl)pyridin-2-ylethynyl]benzo[b]thiophen-2-carboxylate Under an argon atmosphere 3.7 mL (26.72 mmol) of triethylamine was added to a solution of 3.4 g (10.69 mmol) of methyl 5-iodobenzo[b]thiophen-2-carboxylate and 2.48 g (10.69 mmol) of 5-(4-chlorophenyl)-2-ethynylpyridine in 20 mL of THF and the reaction mixture was evacuated three times and in each case gassed with argon. Then 195 mg (0.267 mmol) of PdCl$_2$(dppf)*DCM complex and 51 mg (0.267 mmol) of CuI were added and the reaction mixture was stirred for 70 hours at RT. EtOAc was added, and the precipitated product was filtered off, washed with a little EtOAc, and dried in the air. Yield: 3.0 g (70% of theoretical); $C_{23}H_{14}ClNO_2S$ (M=403.881); calc.: molpeak (M+H)$^+$: 404/406 (Cl); found: molpeak (M+H)$^+$: 404/406 (Cl); HPLC-MS: 7.3 minutes (method B).

22.1c. 5-[5-(4-chlorophenyl)pyridin-2-ylethynyl]benzo[b]thiophen-2-carboxylic acid 22.3 mL of 1N NaOH was added to a suspension of 3.0 g (7.43 mmol) of methyl 5-[5-(4-chlorophenyl)pyridin-2-ylethynyl]benzo[b]thiophen-2-carboxylate in 100 mL of EtOH and the reaction mixture was stirred overnight at RT. The reaction solution was cooled to 0° C. and adjusted to pH 6 by the dropwise addition of 1N HCl. The precipitated product was filtered off, washed with EtOH, and dried in the air. As the product still contained educt, the hydrolysis described above was repeated. Yield: 2.7 g (93% of theoretical); $C_{22}HI_2ClNO_2S$ (M=389.855); calc.: molpeak (M+H)$^+$: 390/392 (Cl); found: molpeak (M+H)$^+$: 390/392 (Cl); R$_f$ value: 0.89 (silica gel, PE/EtOAc 1:1).

22.1d. {5-[5-(4-chlorophenyl)pyridin-2-ylethynyl]benzo[b]thiophen-2-yl}methanol 2.37 g (14.62 mmol) CDI was added to a suspension of 1.9 g (4.87 mmol) of 5-[5-(4-chlorophenyl)pyridin-2-ylethynyl]benzo[b]thiophene-2-carboxylic acid in 40 mL of DMF and the reaction mixture was heated to 50° C. overnight. After cooling to RT, the reaction solution was added to a solution of 552 mg (14.62 mmol) NaBH$_4$ in 5 mL of water in such a way that the temperature did not exceed 30° C. The mixture was stirred for 2 hours at RT, carefully mixed with KHSO$_4$ solution until an acidic reaction was obtained, made basic with saturated sodium carbonate solution, extracted exhaustively with DCM, the combined organic phases were washed twice with water and dried over magnesium sulfate. After the desiccant and solvent had been eliminated, the residue was triturated with PE, suction filtered, and dried in the air. Yield: 1.1 g (60% of theoretical); $C_{22}H_{14}ClNOS$ (M=375.871); calc.: molpeak (M+H)$^+$: 376/378 (Cl); found: molpeak (M+H)$^+$: 376/378 (Cl); HPLC-MS: 6.2 minutes (method B).

22.1e. 2-(2-chloromethylbenzo[b]thiophen-5-ylethynyl)-5-(4-chlorophenyl)pyridine 1.07 mL (15 mmol) of thionyl chloride was added to a solution of 1.1 g (2.93 mmol) of {5-[5-(4-chlorophenyl)pyridin-2-ylethynyl]benzo[b]thiophen-2-yl}methanol in 20 mL of DCM cooled to 0° C. and the reaction mixture was stirred for 70 hours at RT. It was evaporated down in vacuo, the residue was combined with semisaturated sodium bicarbonate solution, extracted exhaustively with DCM, and the combined organic phases were washed twice with water and dried over magnesium sulfate. After the desiccant and solvent had been eliminated, the residue was purified by chromatography (silica gel, PE/EtOAc 7:3). Yield: 0.65 g (56% of theoretical); $C_{22}H_{13}Cl_2NS$ (M=394.317); calc.: molpeak (M+H)$^+$: 394/396/398 (2Cl); found: molpeak (M+H)$^+$: 394/396/398 (2Cl); HPLC-MS: 7.6 minutes (method B).

22.1f. 5-(4-chlorophenyl)-2-[2-(4-methylpiperidin-1-ylmethyl)benzo[b]thiophen-5-ylethynyl]pyridine A solution of 105 mg (0.266 mmol) of 2-(2-chloromethylbenzo[b]thiophen-5-ylethynyl)-5-(4-chlorophenyl)pyridine and 0.31 mL (2.66 mmol) of 4-methylpiperidine in 2 mL of DMF was stirred for 2 hours at 60° C. The reaction mixture was diluted with semisaturated aqueous sodium bicarbonate solution and the aqueous phase was exhaustively extracted with EtOAc. The combined organic extracts were dried over magnesium sulfate and evaporated down in vacuo. The crude product was purified by HPLC-MS (Zorbax Bonus C14, gradient 0.15% formic acid in water/acetonitrile 10/90→90/10 v/v). Yield: 9 mg (7% of theoretical); $C_{28}H_{25}ClN_2S$ (M=457.030); calc.: molpeak (M+H)$^+$: 457/459 (Cl); found: molpeak (M+H)$^+$: 457/459 (Cl); HPLC-MS: 5.68 minutes (method A).

The following Examples were prepared analogously starting from 2-(2-chloromethylbenzo[b]thiophen-5-ylethynyl)-5-(4-chlorophenyl)pyridine (Example 22.1e).

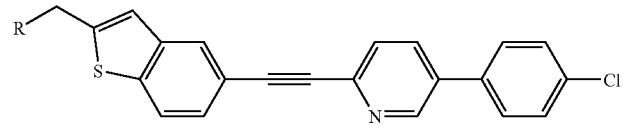

| Example | R | Yield (%) | empirical formula | mass spectrum | retention time HPLC in minutes (method) |
|---|---|---|---|---|---|
| 22.2 | (S)-2-(hydroxymethyl)pyrrolidin-1-yl | 56 | $C_{27}H_{23}ClN_2OS$ | 459/461 [M + H]$^+$ | 5.58 (D) |
| 22.3 | 4-hydroxy-4-methylpiperidin-1-yl | 24 | $C_{28}H_{25}ClN_2OS$ | 473/475 [M + H]$^+$ | 5.56 (D) |
| 22.4 | 4-hydroxy-4-(trifluoromethyl)piperidin-1-yl | 35 | $C_{28}H_{22}ClF_3N_2OS$ | 527/529 [M + H]$^+$ | 5.17 (D) |

EXAMPLE 23.1

5-(4-chlorophenyl)-2-{3-methyl-4-[3-(4-methylpiperidin-1-yl)propyl]phenylethynyl}pyridine

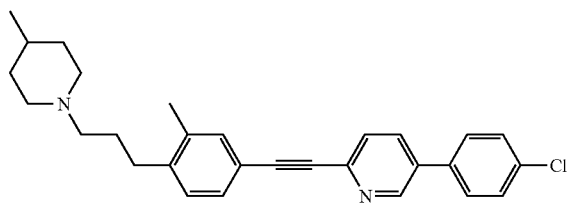

23.1a. 3-(4-bromo-2-methylphenyl)propionaldehyde

A mixture of 1.00 g (3.39 mmol) of 4-bromo-1-iodo-2-methylbenzene, 0.58 g (10.00 mmol) of allyl alcohol, 0.69 g (8.20 mmol) of sodium bicarbonate, 0.92 g (3.30 mmol) of tetrabutylammonium chloride, and 22 mg (0.10 mmol) of palladium (II) acetate in 5 mL of DMF were stirred for 16 hours at 45° C. under argon. The reaction mixture was diluted with EtOAc, and the organic phase was washed with water, dried over magnesium sulfate, and evaporated down in vacuo. The residue was purified by column chromatography (silica gel, PE/EtOAc 4:1). Yield: 0.60 (78% of theoretical); $C_{10}H_{11}BrO$ (M=227.098); calc.: molpeak (M+H)$^+$: 226/228 (Br); found: molpeak (M+H)$^+$: 226/228 (Br); $R_f$ value: 0.45 (silica gel, PE/EtOAc 4:1).

23.1b. 1-[3-(4-bromo-2-methylphenyl)propyl]-4-methylpiperidine 0.70 g (3.30 mmol) of sodium triacetoxyborohydride and 0.16 mL of glacial acetic acid were added to a solution of 0.32 mL (2.70 mmol) of 4-methylpiperidine and 0.60 g (2.64 mmol) of 3-(4-bromo-2-methylphenyl)propionaldehyde in 10 mL of THF and the mixture was stirred for 2 hours at RT. The reaction mixture was diluted with EtOAc, and the organic phase was washed with semisaturated aqueous sodium bicarbonate solution washed, dried over magnesium sulfate, and evaporated down in vacuo. Yield: 0.65 (78% of theoretical); $C_{16}H_{24}BrO$ (M=310.273); calc.: molpeak (M+H)$^+$: 310/312 (Br); found: molpeak (M+H)$^+$: 310/312 (Br); $R_f$ value: 0.28 (silica gel, PE/EtOAc 3:2).

23.1c. 1-[3-(4-iodo-2-methylphenyl)propyl]-4-methylpiperidine

The product was obtained analogously to Example 20.1b starting from 1-[3-(4-bromo-2-methylphenyl)propyl]-4-methylpiperidine. Yield: 0.70 g (94% of theoretical); $C_{16}H_{24}IO$ (M=357.273); calc.: molpeak (M+H)$^+$: 358; found: molpeak (M+H)$^+$: 358; HPLC-MS: 6.42 minutes (method A).

23.1d. 5-(4-chlorophenyl)-2-{3-methyl-4-[3-(4-methylpiperidin-1-yl)propyl]phenylethynyl}pyridine The product was obtained analogously to Example 7.1e starting from 1-[3-(4-iodo-2-methylphenyl)propyl]-4-methylpiperidine and 5-(4-chlorophenyl)-2-ethynylpyridine. Yield: 29 mg (9% of theoretical); $C_{29}H_{31}ClN_2$ (M=443.023);

calc.: molpeak (M+H)$^+$: 443/445 (Cl); found: molpeak (M+H)$^+$: 443/445 (Cl); HPLC-MS: 8.55 minutes (method A).

EXAMPLE 24.1

5-(4-chlorophenyl)-2-[3-ethyl-4-(2-pyrrolidin-1-ylethoxy)phenylethynyl]pyridine

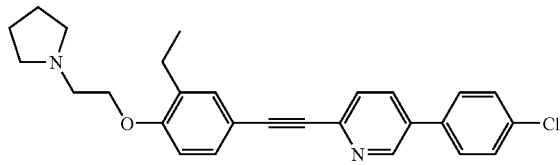

24.1a.
5-bromo-2-(2-pyrrolidin-1-ylethoxy)benzaldehyde

A suspension of 6.00 g (29.85 mmol) of 5-bromo-2-hydroxybenzaldehyde, 5.84 g (3.43 mmol) of 1-(2-chloroethyl)pyrrolidine, and 12.38 g (89.54 mmol) of potassium carbonate was stirred for 2 hours at 50° C. and for 2 hours at 75° C., cooled to RT, filtered, and evaporated down in vacuo. The crude product was purified by column chromatography (silica gel, gradient EtOAc/MeOH 100:0→85:15). Yield: 5.89 g (66% of theoretical); $C_{13}H_{16}BrNO_2$ (M=298.176); calc.: molpeak (M+H)$^+$: 298/300 (Br); found: molpeak (M+H)$^+$: 298/300 (Br); HPLC-MS: 4.82 minutes (method A).

24.1b.
1-[2-(4-bromo-2-vinylphenoxy)ethyl]pyrrolidine

The product was obtained analogously to Example 11.1b starting from 5-bromo-2-(2-pyrrolidin-1-ylethoxy)benzaldehyde. The crude product was purified by column chromatography (silica gel, PE/EtOAc 3:2). Yield: 1.03 g (35% of theoretical); $C_{14}H_{18}BrNO$ (M=296.203); calc.: molpeak (M+H)$^+$: 296/298 (Br); found: molpeak (M+H)$^+$: 296/298 (Br); HPLC-MS: 6.00 minutes (method A).

24.1c. 1-[2-(2-ethylphenoxy)ethyl]pyrrolidine

A solution of 0.41 g (1.38 mmol) of 1-[2-(4-bromo-2-vinylphenoxy)ethyl]pyrrolidine and 0.41 mL (2.94 mmol) of triethylamine in 25 mL of MeOH was degassed with argon and then combined with 35.5 mg (0.072 mmol) of bis(1,5-cyclooctadiene)dirhodium (I) dichloride and 57.1 mg (0.138 mmol) of 1,3-bis(diphenylphosphino)propane. The mixture was hydrogenated at RT and 3 bar hydrogen pressure. The reaction mixture was evaporated down in vacuo, and the residue was stirred with EtOAc, filtered, and the filtrate was evaporated down in vacuo. Yield: 0.26 g (87% of theoretical); $C_{14}H_{21}NO$ (M=219.330); calc.: molpeak (M+H)$^+$: 220; found: molpeak (M+H)$^+$: 220.

24.1d.
1-[2-(4-iodo-2-ethylphenoxy)ethyl]pyrrolidine

A finely triturated mixture of 0.8 g of silica gel (0.2-0.5 mm) and 0.41 g (1.00 mmol) of iron (II) nitrate nonahydrate was added to a solution of 0.44 g (2.01 mmol) of 1-[2-(2-ethylphenoxy)ethyl]pyrrolidine and 0.28 g (1.10 mmol) of iodine in 5 mL of DCM and the mixture was stirred for 12 hours at RT. The reaction mixture was filtered and the filtrate was evaporated down in vacuo. The residue was purified by column chromatography (silica gel, DCM/MeOH/sat. aqueous ammonia 9:1:0.1). Yield: 0.286 g (41% of theoretical); $C_{14}H_{20}INO$ (M=345.219); calc.: molpeak (M+H)$^+$: 346; found: molpeak (M+H)$^+$: 346; HPLC-MS: 6.74 minutes (method A).

24.1e. 5-(4-chlorophenyl)-2-[3-ethyl-4-(2-pyrrolidin-1-ylethoxy)phenylethynyl]pyridine The product was obtained analogously to Example 7.1e starting from 1-[2-(4-iodo-2-ethylphenoxy)ethyl]pyrrolidine and 5-(4-chlorophenyl)-2-ethynylpyridine. Yield: 44 mg (12% of theoretical); $C_{27}H_{27}ClN_2O$ (M=430.969); calc.: molpeak (M+H)$^+$: 431/433 (Cl); found: molpeak (M+H)$^+$: 431/433 (Cl); HPLC-MS: 5.74 minutes (method A).

EXAMPLE 25.1

4-(6-{4-[2-(4-methylpiperidin-1-yl)ethoxy]phenylethynyl}pyridin-3-yl)benzaldehyde

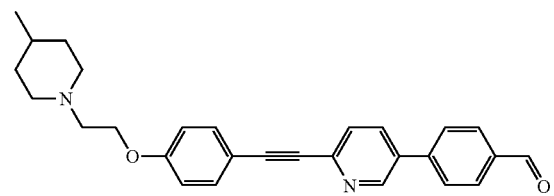

25.1a. 5-bromo-2-{4-[2-(4-methylpiperidin-1-yl)ethoxy]phenylethynyl}pyridine The product was prepared analogously to Example 7.1e starting from 1-[2-(4-iodophenoxy)ethyl]-4-methylpiperidine and 5-bromo-2-ethynylpyridine. Yield: 1.00 g (62% of theoretical); $C_{21}H_{23}BrN_2O$ (M=399.324); calc.: molpeak (M+H)$^+$: 399/401 (Br); found: molpeak (M+H)$^+$: 399/401 (Br); HPLC-MS: 4.64 minutes (method A).

25.1b. 4-(6-{4-[2-(4-methylpiperidin-1-yl)ethoxy]phenylethynyl}pyridin-3-yl)benzaldehyde The product was obtained analogously to Example 1.1e starting from 5-bromo-2-{4-[2-(4-methylpiperidin-1-yl)ethoxy]phenylethynyl}pyridine and 4-formylphenylboric acid. Yield: 0.20 g (47% of theoretical); $C_{28}H_{28}N_2O_2$ (M=424.534); calc.: molpeak (M+H)$^+$425; found: molpeak (M+H)$^+$: 425; $R_f$ value: 0.40 (silica gel, DCM/MeOH 9:1).

EXAMPLE 26.1

1-[5-[5-(4-chlorophenyl)pyridin-2-ylethynyl]-2-(2-pyrrolidin-1-ylethoxy)phenyl]ethanol

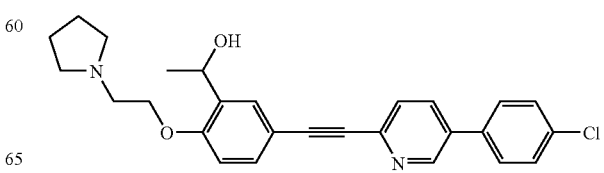

Under argon 200 μL (0.60 mmol) of methylmagnesium bromide (3M in diethyl ether) was added slowly at RT to a suspension of 107 mg (0.25 mmol) of 5-[5-(4-chlorophenyl)pyridin-2-ylethynyl]-2-(2-pyrrolidin-1-ylethoxy)benzaldehyde (Example 14.6c) in 1 mL of diethyl ether and the mixture was stirred for 16 hours at RT. The reaction mixture was poured onto cold, 5% aqueous ammonium chloride solution and the aqueous phase was extracted with DCM and a little MeOH. The combined organic extracts were washed with water, dried over magnesium sulfate, and evaporated down in vacuo. The residue was triturated with MTBE and a little isopropanol, the precipitate was filtered off and dried in vacuo. The product was isolated as the hydrochloride salt. Yield: 30 mg (25% of theoretical); $C_{27}H_{27}ClN_2O_2 \cdot HCl$ (M=483.429); calc.: molpeak (M+H)$^+$: 447/449 (Cl); found: molpeak (M+H)$^+$: 447/449 (Cl); HPLC-MS: 7.40 minutes (method A).

EXAMPLE 27.1

1-{5-[5-(4-chlorophenyl)pyridin-2-ylethynyl]-2-[2-(4-methylpiperidin-1-yl)ethoxy]phenyl}ethanol

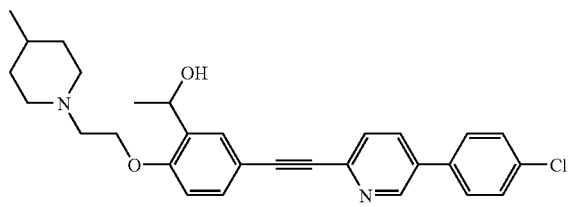

A solution of 30 mg (0.74 mmol) of sodium borohydride in 3 mL of water was added to a solution of 0.32 g (0.68 mmol) of 1-{5-[5-(4-chlorophenyl)pyridin-2-ylethynyl]-2-[2-(4-methylpiperidin-1-yl)ethoxy]phenyl}ethanone (Example 13.1) in 8 mL of EtOH and the mixture was stirred for 30 minutes at 50° C. The reaction mixture was evaporated down in vacuo, and the residue was stirred for 5 minutes with 4 mL of 1N aqueous HCl, diluted with EtOAc, and neutralized with saturated aqueous sodium bicarbonate solution. The phases were separated and the aqueous phase was extracted with EtOAc. The combined organic extracts were dried over magnesium sulfate and evaporated down in vacuo. The residue was triturated with acetonitrile and a little EtOAc, the precipitate was filtered off, and dried in the air. Yield: 100 mg (31% of theoretical); $C_{29}H_{31}ClN_2O_2$ (M=475.021); calc.: molpeak (M+H)$^+$: 475/477 (Cl); found: molpeak (M+H)$^+$: 475/477 (Cl); HPLC-MS: 5.20 minutes (method A).

EXAMPLE 28.1

{5-[5-(4-chlorophenyl)pyridin-2-ylethynyl]thiophen-3-yl}-[2-(4-methylpiperidin-1-yl)ethyl]amine

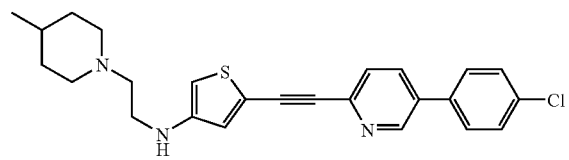

28.1a. 2-(4-bromothiophen-2-ylethynyl)-5-(4-chlorophenyl)pyridine

The product was obtained analogously to Example 7.1e starting from 2,4-dibromothiophene and 5-(4-chlorophenyl)-2-ethynylpyridine. Yield: 0.78 g (50% of theoretical); $C_{17}H_9BrClNS$ (M=374.683); calc.: molpeak (M+H)$^+$: 374/376/378 (BrCl); found: molpeak (M+H)$^+$: 374/376/378 (BrCl); HPLC-MS: 7.40 minutes (method B).

28.1b. 5-(4-chlorophenyl)-2-(4-iodothiophen-2-ylethynyl)pyridine

The product was obtained analogously to Example 20.1b starting from 2-(4-bromothiophen-2-ylethynyl)-5-(4-chlorophenyl)pyridine. The crude product was used in the following reaction step without any further purification. Yield: 0.20 g (90% of theoretical); $C_{17}H_9ClINS$ (M=421.683); $R_f$ value: 0.90 (silica gel, PE/EtOAc 3:2).

28.1c. {5-[5-(4-chlorophenyl)pyridin-2-ylethynyl]thiophen-3-yl}-[2-(4-methylpiperidin-1-yl)ethyl]amine The product was obtained analogously to Example 20.1a starting from 5-(4-chlorophenyl)-2-(4-iodothiophen-2-ylethynyl)pyridine and 2-(4-methylpiperidin-1-yl)ethylamine. Yield: 3 mg (1% of theoretical); $C_{25}H_{26}ClN_3S$ (M=436.013); calc.: molpeak (M+H)$^+$: 436/438 (Cl); found: molpeak (M+H)$^+$: 436/438 (Cl); HPLC-MS: 5.10 minutes (method B).

EXAMPLE 29.1

5-(4-difluoromethylphenyl)-2-{4-[2-(4-methylpiperidin-1-yl)ethoxy]phenylethynyl}pyridine

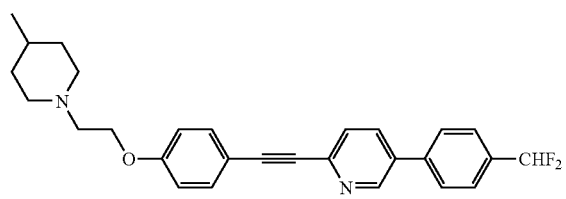

74 μL (0.200 mmol) of New-DAST (50% in toluene) was added to a solution of 50 mg (0.118 mmol) of 4-(6-{4-[2-(4-methylpiperidin-1-yl)ethoxy]phenylethynyl}pyridin-3-yl)benzaldehyde (Example 25.1) in 0.5 mL of DCM and the mixture was stirred for 16 hours at 35° C. A further 74 μL (0.200 mmol) of New-DAST (50% in toluene) were added and the mixture was stirred for 24 hours at 35° C. The reaction mixture was combined with 5 mL of 2M aqueous sodium carbonate solution and exhaustively extracted with DCM. The combined organic phases were washed with semisaturated aqueous sodium carbonate solution, dried over magnesium sulfate and evaporated down in vacuo. The residue was purified by MPLC (Zorbax Stable Bond C18, gradient 0.15% formic acid in water/acetonitrile 10/90→90/10 v/v). Yield: 1.2 mg (2% of theoretical); $C_{28}H_{28}F_2N_2O$ (M=446.532); calc.: molpeak (M+H)$^+$: 447; found: molpeak (M+H) 447; HPLC-MS: 8.00 minutes (method A).

EXAMPLE 30.1

5-[5-(4-chlorophenyl)pyridin-2-ylethynyl]-2-(2-pyrrolidin-1-ylethoxy)benzylamine

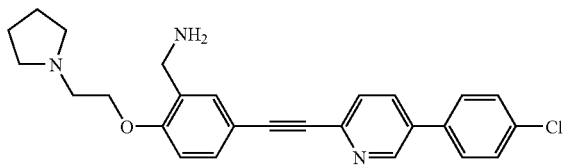

30.1a. [5-bromo-2-(2-pyrrolidin-1-ylethoxy)phenyl]methanol 3.4 mL (3.40 mmol) of a lithium aluminum hydride solution (1M in THF) was added under argon at 0° C. to a solution of 1.00 g (3.35 mmol) of 5-bromo-2-(2-pyrrolidin-1-ylethoxy)benzaldehyde (Example 24.1a) in 20 mL of THF and the mixture was stirred for 2 hours at RT. A further 6.8 mL of lithium aluminum hydride solution (1M in THF) was added and the mixture was stirred for 2 hours at RT. The reaction mixture was slowly combined with sat. aqueous ammonium chloride solution and the aqueous phase was exhaustively extracted with EtOAc. The combined organic extracts were dried over magnesium sulfate and evaporated down in vacuo. As some starting material could still be detected, the reaction was repeated with 1.7 mL of lithium aluminum hydride solution (1M in THF) and the working up was repeated. Yield: 0.82 g (81% of theoretical); $C_{13}H_{18}BrNO_2$ (M=300.192); calc.: molpeak $(M+H)^+$: 300/302 (Br); found: molpeak $(M+H)^+$: 300/302 (Br); HPLC-MS: 4.62 minutes (method A).

30.1b. 1-[2-(4-bromo-2-chloromethylphenoxy)ethyl]pyrrolidine 0.16 mL (2.20 mmol) of thionyl chloride was added at −10° C. to a solution of 0.60 g (2.00 mmol) of [5-bromo-2-(2-pyrrolidin-1-ylethoxy)phenyl]methanol and 0.42 mL (3.00 mmol) of triethylamine in 30 mL of THF and the mixture was stirred for 16 hours at RT. Ice and dilute aqueous sodium bicarbonate solution was added to the reaction mixture and the phases were separated. The aqueous phase was exhaustively extracted with DCM, and the combined organic phases were washed with water, dried over magnesium sulfate, and evaporated down in vacuo. Yield: 0.39 g (62% of theoretical); $C_{13}H_{17}BrClNO$ (M=318.637); calc.: molpeak $(M+H)^+$: 318/320/322 (BrCl); found: molpeak $(M+H)^+$: 318/320/322 (BrCl); HPLC-MS: 5.84 minutes (method A).

30.1c. 1-[2-(2-azidomethyl-4-bromophenoxy)ethyl]pyrrolidine 0.33 g (5.00 mmol) of sodium azide were added to a solution of 500 mg (1.57 mmol) of 1-[2-(4-bromo-2-chloromethylphenoxy)ethyl]pyrrolidine in 5 mL of DMF and the mixture was stirred for 16 hours at 35° C. Water was added and the phases were separated. The aqueous phase was exhaustively extracted with DCM, and the combined organic extracts were washed with saturated aqueous sodium bicarbonate solution, dried over magnesium sulfate, and evaporated down in vacuo. The crude product was used in the next reaction step without any further purification. Yield: 0.42 g (82% of theoretical); $C_{13}H_{17}BrN_4O$ (M=325.204); HPLC-MS: 5.62 minutes (method A).

30.1d. 5-bromo-2-(2-pyrrolidin-1-ylethoxy)benzylamine 0.66 g (2.50 mmol) of triphenylphosphine was added to a solution of 0.40 g (1.23 mmol) 1-[2-(2-azidomethyl-4-bromophenoxy)ethyl]pyrrolidine in 5 mL of THF and the mixture was stirred for 30 minutes at RT. Water was added and the aqueous phase was exhaustively extracted with DCM. The combined organic extracts were dried over magnesium sulfate and evaporated down in vacuo. Yield: 0.185 g (50% of theoretical); $C_{13}H_{19}BrN_2O$ (M=299.207); calc.: molpeak $(M+H)^+$: 299/301 (Br); found: molpeak $(M+H)^+$: 299/301 (Br); HPLC-MS: 1.38 minutes (method A).

30.1e. 5-iodo-2-(2-pyrrolidin-1-ylethoxy)benzylamine

The product was obtained analogously to Example 20.1 b starting from 5-bromo-2-(2-pyrrolidin-1-ylethoxy)benzylamine. Yield: 74 mg (36% of theoretical); $C_{13}H_{19}IN_2O$ (M=346.207); calc.: molpeak $(M+H)^+$: 347; found: molpeak $(M+H)^+$: 347; HPLC-MS: 2.77 minutes (method A).

30.1f 5-[5-(4-chlorophenyl)pyridin-2-ylethynyl]-2-(2-pyrrolidin-1-ylethoxy)benzylamine The product was obtained analogously to Example 7.1e starting from 5-iodo-2-(2-pyrrolidin-1-ylethoxy)benzylamine and 5-(4-chlorophenyl)-2-ethynylpyridine. Yield: 28 mg (11% of theoretical); $C_{26}H_{26}ClN_3O$ (M=431.957); calc.: molpeak $(M+H)^+$: 432/434 (Cl); found: molpeak $(M+H)^+$: 432/434 (Cl); HPLC-MS: 3.90 minutes (method B).

EXAMPLE 31.1

N-(5-(4-chlorophenyl)-2-{4-[2-(4-methylpiperidin-1-yl)ethoxy]phenylethynyl}pyridin-3-yl)acetamide

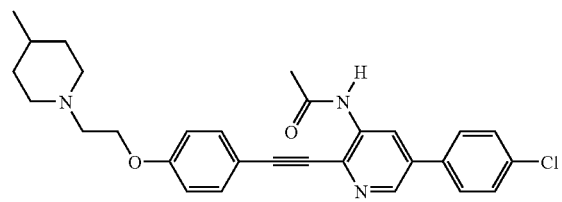

125 μL (1.345 mmol) of acetic anhydride was added at RT to a solution of 100 mg (0.224 mmol) of 5-(4-chlorophenyl)-2-{4-[2-(4-methylpiperidin-1-yl)ethoxy]phenylethynyl}pyridin-3-ylamine (Example 19.1d) and 62 μL (0.448 mmol) of triethylamine in 5 mL of DCM and the mixture was refluxed for 72 hours. The reaction mixture was diluted with DCM, and the organic phase was washed with saturated aqueous sodium bicarbonate solution, water, and 12% aqueous HCl, dried over magnesium sulfate, and evaporated down in vacuo. The residue was triturated with DIPE, and the precipitate was filtered off and dried in vacuo. The crude product was purified by HPLC-MS (Zorbax Stable Bond C18, gradient 0.15% formic acid in water/acetonitrile 10/90→90/10 v/v). Yield: 23 mg (21% of theoretical);

$C_{29}H_{30}ClN_3O_2$ (M=488.020); calc.: molpeak (M+H)⁺: 488/490 (Cl); found: molpeak (M+H)⁺: 488/490 (Cl); HPLC-MS: 5.01 minutes (method B).

EXAMPLE 32.1

6-[5-(4-chlorophenyl)pyridin-2-ylethynyl]-4-methyl-2-(4-methylpiperidin-1-ylmethyl)quinoline

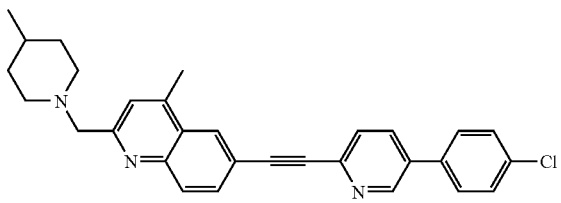

32.1a. methyl 6-bromo-4-methylquinoline-2-carboxylate

A solution of 1.10 g (4.29 mmol) of 6-bromo-2-chloro-4-methylquinoline, 0.24 g (0.43 mmol) of 1,1'-bis(diphenylphosphino)ferrocene, 97 mg (0.43 mmol) of palladium (II) acetate, and 1.25 mL (9.00 mmol) of triethylamine in 60 mL of DMF/MeOH (1:1) was stirred for 10 minutes at 50° C. and under 2 bar CO pressure. The reaction mixture was evaporated down in vacuo, the residue was combined with EtOAc, the precipitate was filtered off, and the filtrate was evaporated down. The residue was purified by column chromatography (silica gel, gradient PE/EtOAc 8:2→6:4). Yield: 0.65 g (54% of theoretical); $C_{12}H_{10}BrNO_2$ (M=280.117); calc: molpeak (M+H)⁺: 280/282 (Br); found: molpeak (M+H)⁺: 280/282 (Br); HPLC-MS: 8.55 minutes (method A).

32.1b. (6-bromo-4-methylquinolin-2-yl)methanol

Under a nitrogen atmosphere at 0C, 1.50 mL (1.50 mmol) of a lithium aluminum hydride solution (1M in THF) was slowly added to a solution of 0.65 g (2.32 mmol) of methyl 6-bromo-4-methylquinoline-2-carboxylate in 30 mL of THF and the mixture was stirred for 30 minutes at 0° C. A further 0.25 mL of lithium aluminum hydride solution (1M in THF) was added and the mixture was stirred for 20 minutes at 0° C. The reaction mixture was combined with a few drops of EtOAc, worked up using the Fieser-Fieser method, and the precipitate was filtered off and washed with EtOAc. The filtrate was evaporated down in vacuo. Yield: 0.25 g (43% of theoretical); $C_{11}H_{10}BrNO$ (M=252.107); calc.: molpeak (M+H)⁺: 252/254 (Br); found: molpeak (M+H)⁺: 252/254 (Br); $R_f$ value: 0.25 (silica gel, PE/EtOAc 3:2).

32.1c. (6-iodo-4-methylquinolin-2-yl)methanol

The product was obtained analogously to Example 11.1 a starting from (6-bromo-4-methylquinolin-2-yl)methanol. Yield: 0.20 g (67% of theoretical); $C_{11}H_{10}INO$ (M=299.108); calc.: molpeak (M+H)⁺: 300; found: molpeak (M+H)⁺: 300; HPLC-MS: 3.98 minutes (method B).

32.1d. {6-[5-(4-chlorophenyl)pyridin-2-ylethynyl]-4-methylquinolin-2-yl}methanol The product was obtained analogously to Example 7.1 e starting from (6-iodo-4-methylquinolin-2-yl)methanol and 5-(4-chlorophenyl)-2-ethynylpyridine. Yield: 50 mg (19% of theoretical); $C_{24}H_{17}ClN_2O$ (M=384.857); calc.: molpeak (M+H)⁺: 385/387 (Cl); found: molpeak (M+H)⁺: 385/387 (Cl); HPLC-MS: 5.50 minutes (method B).

32.1e. 6-[5-(4-chlorophenyl)pyridin-2-ylethynyl]-4-methyl-2-(4-methylpiperidin-1-ylmethyl)quinoline 16 µL (0.20 mmol) of thionyl chloride was added at RT to a solution of 50 mg (0.13 mmol) of {6-[5-(4-chlorophenyl)pyridin-2-ylethynyl]-4-methylquinolin-2-yl}methanol and 52 µL (0.65 mmol) of pyridine in 3 mL of DCM and the mixture was stirred for 2 hours at RT. The reaction mixture was diluted with DCM, and the organic phase was washed with saturated aqueous sodium bicarbonate solution, dried over magnesium sulfate, and evaporated down in vacuo. The residue was taken up in 3 mL of DMF, combined with 60 µL (0.51 mmol) of 4-methylpiperidine and stirred for 16 hours at RT. The reaction mixture was evaporated down in vacuo, diluted with DCM, and the organic phase was washed with saturated aqueous sodium bicarbonate solution, dried over magnesium sulfate and evaporated down in vacuo. The crude product was purified by column chromatography (silica gel, gradient DCM/MeOH/sat. aqueous ammonia 100:0:0 95:5:0.5) and HPLC-MS (Zorbax Bonus C18 amide-phase 5 µm, gradient 0.15% formic acid in water/acetonitrile 10/90→90/10 v/v). Yield: 4 mg (7% of theoretical); $C_{30}H_{28}ClN_3$ (M=466.016); calc.: molpeak (M+H)⁺: 466/468 (Cl); found: molpeak (M+H)⁺: 466/468 (Cl); $R_f$ value: 0.38 (silica gel, DCM/MeOH/sat. aqueous ammonia 9:1:0.1).

EXAMPLE 33.1

5-[5-(4-chlorophenyl)pyridin-2-ylethynyl]-2-(2-pyrrolidin-1-ylethoxy)phenol

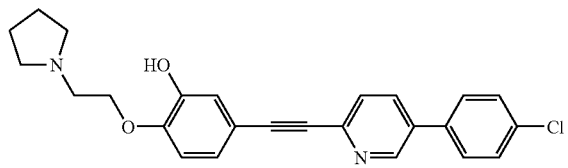

33.1a. 1-[2-(4-bromo-2-methoxyphenoxy)ethyl]pyrrolidine

The product was obtained analogously to Example 24.1a starting from 4-bromo-2-methoxyphenol and 1-(2-chloroethyl)pyrrolidine hydrochloride. Yield: 3.96 g (45% of theoretical); $C_{13}H_{19}BrNO_2$ (M=300.192); calc.: molpeak (M+H)⁺: 300/302 (Br); found: molpeak (M+H)⁺: 300/302 (Br); HPLC-MS: 4.67 minutes (method A).

33.1b. 1-[2-(4-iodo-2-methoxyphenoxy)ethyl]pyrrolidine

The product was obtained analogously to Example 20.1b starting from 1-[2-(4-bromo-2-methoxyphenoxy)ethyl]pyrrolidine. Yield: 4.19 g (93% of theoretical); $C_{13}H18INO_2$ (M=347.192); calc.: molpeak (M+H)⁺: 348; found: molpeak (M+H)⁺: 348; HPLC-MS: 4.65 minutes (method A).

33.1c. 5-iodo-2-(2-pyrrolidin-1-ylethoxy)phenol

A mixture of 3.10 g (8.93 mmol) of 1-[2-(4-iodo-2-methoxyphenoxy)ethyl]pyrrolidine and 4.50 g (38.94 mmol) of pyridinium hydrochloride was heated to 200° C.-250° C. for 5 minutes, cooled to RT, and combined with DCM. The organic phase was washed with water and saturated aqueous NaCl solution, dried over sodium sulfate, and evaporated down in vacuo. The residue was stirred with acetonitrile, and the precipitate was filtered off and dried in vacuo. Yield: 0.75 g (25% of theoretical); $C_{12}H_{16}INO_2$ (M=333.165); calc.: molpeak (M+H)+334; found: molpeak (M+H)+: 334; HPLC-MS: 5.02 minutes (method A).

33.1d. 5-[5-(4-chlorophenyl)pyridin-2-ylethynyl]-2-(2-pyrrolidin-1-ylethoxy)phenol The product was obtained analogously to Example 7.1e starting from 5-iodo-2-(2-pyrrolidin-1-ylethoxy)phenol and 5-(4-chlorophenyl)-2-ethynylpyridine. Yield: 0.75 g (48% of theoretical); $C_{25}H_{23}ClN_2O_2$ (M=418.915); calc.: molpeak (M+H)+: 419/421 (Cl); found: molpeak (M+H)+: 419/421 (Cl); HPLC-MS: 7.33 minutes (method A).

EXAMPLE 34.1

5-(4-chlorophenyl)-2-[3-propoxy-4-(2-pyrrolidin-1-ylethoxy)phenylethynyl]pyridine

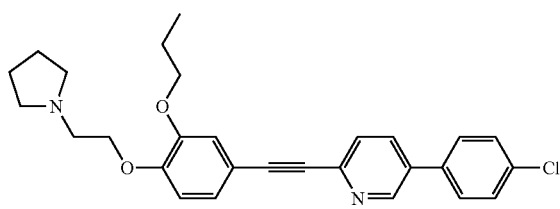

A suspension of 0.15 g (0.36 mmol) of 5-[5-(4-chlorophenyl)pyridin-2-ylethynyl]-2-(2-pyrrolidin-1-ylethoxy)phenol (Example 33.1d), 38 µL (0.43 mmol) of 1-bromopropane, and 148 mg (1.07 mmol) of potassium carbonate in 2 mL of acetonitrile was stirred for 2 hours at 75° C. The reaction mixture was diluted with water and the aqueous phase exhaustively extracted with DCM. The combined organic extracts were washed with saturated aqueous sodium bicarbonate solution, dried over magnesium sulfate, and evaporated down in vacuo. The residue was purified by HPLC-MS (Zorbax Bonus C 18 amide-phase 5 µm, gradient 0.15% formic acid in water/acetonitrile 10/90→90/10 v/v). Yield: 4 mg (2% of theoretical); $C_{28}H_{29}ClN_2O_2$ (M=460.995); calc.: molpeak (M+H)+: 461/463 (Cl); found: molpeak (M+H)+: 461/463 (Cl); HPLC-MS: 9.68 minutes (method A).

The following Example was prepared analogously, starting from 5-[5-(4-chlorophenyl)pyridin-2-ylethynyl]-2-(2-pyrrolidin-1-ylethoxy)phenol (Example 33.1d).

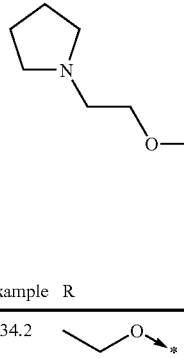

| Example | R | Yield (%) | empirical formula | mass spectrum | retention time HPLC in minutes (method) |
|---|---|---|---|---|---|
| 34.2 | (see structure) | 42 | $C_{27}H_{27}ClN_2O_2$ | 447/449 [M + H]+ | 7.91 (A) |

EXAMPLE 35.1

5-(4-chlorophenyl)-2-[3-isopropoxy-4-(2-pyrrolidin-1-ylethoxy)phenylethynyl]pyridine

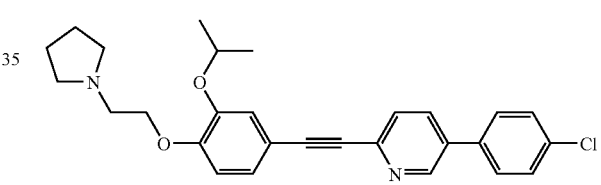

35.1a. 1-[2-(4-iodo-2-isopropoxyphenoxy)ethyl]pyrrolidine

A suspension of 0.15 g (0.45 mmol) of 5-iodo-2-(2-pyrrolidin-1-ylethoxy)phenol (Example 33.1c), 52 µL (0.55 mmol) of 2-bromopropane, and 186 mg (1.35 mmol) of potassium carbonate in 2 mL of acetonitrile was stirred for 2 hours at 75° C. The reaction mixture was diluted with water and the aqueous phase exhaustively extracted with DCM. The combined organic extracts were washed with saturated aqueous sodium bicarbonate solution, dried over magnesium sulfate, and evaporated down in vacuo. Yield: 77 mg (46% of theoretical); $C_{15}H_{22}INO_2$ (M=375.245); calc.: molpeak (M+H)+: 376; found: molpeak (M+H)+: 376; HPLC-MS: 5.86 minutes (method A).

35.1b. 5-(4-chlorophenyl)-2-[3-isopropoxy-4-(2-pyrrolidin-1-ylethoxy)phenylethynyl]pyridine The product was obtained analogously to Example 7.1e starting from 1-[2-(4-iodo-2-isopropoxyphenoxy)ethyl]pyrrolidine and 5-(4-chlorophenyl)-2-ethynylpyridine. Yield: 7 mg (8% of theoretical); $C_{28}H_{29}ClN_2O_2$ (M=460.995); calc.: molpeak (M+H)+:461/463 (Cl); found: molpeak (M+H)+: 461/463 (Cl); HPLC-MS: 10.50 minutes (method A).

EXAMPLE 36.1

(3-{5-[5-(4-chlorophenyl)pyridin-2-ylethynyl]pyridin-2-yl}propyl)-4-methylpiperidine

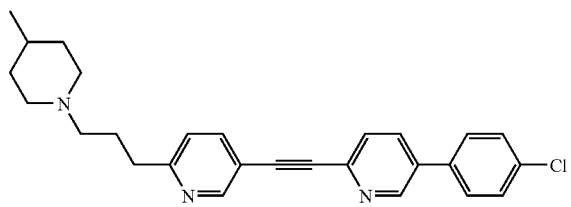

36.1a. 3-(5-iodopyridin-2-yl)propan-1-ol

The product was obtained analogously to Example 11.1a starting from 3-(5-bromopyridin-2-yl)propan-1-ol. Yield: 0.83 g (68% of theoretical); $C_8H_{10}INO$ (M=263.076); calc.: molpeak (M+H)$^+$: 264; found: molpeak (M+H)$^+$: 264; HPLC-MS: 4.84 minutes (method A).

36.1b. 3-{5-[5-(4-chlorophenyl)pyridin-2-ylethynyl]pyridin-2-yl}propan-1-ol

The product was obtained analogously to Example 7.1e starting from 3-(5-iodopyridin-2-yl)propan-1-ol and 5-(4-chlorophenyl)-2-ethynylpyridine. Yield: 0.80 g (74% of theoretical); $C_{21}H_{17}ClN_2O$ (M=348.825); calc.: molpeak (M+H)$^+$: 349/351 (Cl); found: molpeak (M+H)$^+$: 349/351 (Cl); HPLC-MS: 8.24 minutes (method A).

36.1c. 3-{5-[5-(4-chlorophenyl)pyridin-2-ylethynyl]pyridin-2-yl}propionaldehyde 1.62 mL (20.07 mmol) of pyridine and 8.51 g (3.01 mmol) of Dess-Martin periodinane solution (15% in DCM) were added to a solution of 0.70 g (2.01 mmol) of 3-{5-[5-(4-chlorophenyl)pyridin-2-ylethynyl]pyridin-2-yl}propan-1-ol in 50 mL of DCM and the mixture was stirred for 16 hours at RT. Semisaturated aqueous sodium bicarbonate solution was added and the aqueous phase was extracted with MTBE. The combined organic extracts were dried over magnesium sulfate and evaporated down in vacuo. The residue was purified by HPLC-MS (Zorbax Bonus C18 amide-phase 5 µm, gradient 0.15% formic acid in water/acetonitrile 10/90→90/10 v/v). Yield: 115 mg (17% of theoretical); $C_{21}H_{15}ClN_2O$ (M=346.809); calc.: molpeak (M+H)$^+$: 347/349 (Cl); found: molpeak (M+H)$^+$: 347/349 (Cl); HPLC-MS: 6.70 minutes (method A).

36.1d. (3-{5-[5-(4-chlorophenyl)pyridin-2-ylethynyl]pyridin-2-yl}propyl)-4-methylpiperidine 74 mg (0.35 mmol) of sodium triacetoxyborohydride and 41 µL (0.73 mmol) of HOAc were added to a solution of 100 mg (0.288 mmol) of 3-{5-[5-(4-chlorophenyl)pyridin-2-ylethynyl]pyridin-2-yl}propionaldehyde and 34 µL (0.288 mmol) of 4-methylpiperidine in 6 mL of THF and the mixture was stirred for 16 hours at RT. Saturated aqueous sodium bicarbonate solution was added and the aqueous phase was extracted with EtOAc. The combined organic extracts were dried over magnesium sulfate and evaporated down in vacuo. Yield: 44 mg (35% of theoretical); $C_{27}H_{28}ClN_3$ (M=429.984); calc.: molpeak (M+H)$^+$: 430/432 (Cl); found: molpeak (M+H)$^+$: 430/432 (Cl); HPLC-MS: 7.65 minutes (method A).

EXAMPLE 37.1 tert-butyl (S)-2-({4-[5-(4-chlorophenyl)pyridin-2-ylethynyl]phenylamino}methyl)pyrrolidine-1-carboxylate

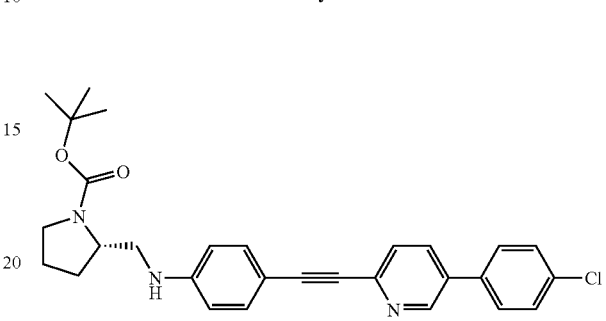

37.1a. 2-(4-bromophenylethynyl)-5-(4-chlorophenyl)pyridine

The product was obtained analogously to Example 7.1e starting from 4-bromoiodobenzene and 5-(4-chlorophenyl)-2-ethynylpyridine. Yield: 7.10 g (90% of theoretical); $C_{19}H_{11}BrClN$ (M=368.654); calc.: molpeak (M+H)$^+$: 368/370/372 (BrCl); found: molpeak (M+H)$^+$: 368/370/372 (BrCl); HPLC-MS: 7.60 minutes (method A).

37.1b. 5-(4-chlorophenyl)-2-(4-iodophenylethynyl)pyridine

The product was obtained analogously to Example 20.1b starting from 2-(4-bromophenylethynyl)-5-(4-chlorophenyl)pyridine. Yield: 0.80 g (64% of theoretical); $C_{19}H_{11}ClIN$ (M=415.655); calc.: molpeak (M+H)$^+$: 416/418 (Cl); found: molpeak (M+H)$^+$: 416/418 (Cl); HPLC-MS: 7.90 minutes (method B).

37.1c. tert-butyl (S)-2-({4-[5-(4-chlorophenyl)pyridin-2-ylethynyl]phenylamino}methyl)pyrrolidine-1-carboxylate 4.90 g (20.00 mmol) of potassium phosphate monohydrate were added under argon to a mixture of 4.16 g (10.00 mmol) of 5-(4-chlorophenyl)-2-(4-iodophenylethynyl)pyridine, 3.10 g (15.00 mmol) of tert-butyl (S)-2-aminomethylpyrrolidine-1-carboxylate, 194 mg (1.00 mmol) of CuI, 0.77 g (4.00 mmol) of N,N-diethylsalicylamide in 10 mL of DMF and the mixture was stirred for 16 hours at 100° C. The reaction mixture was combined with 100 mL of 5% aqueous ammonia, stirred, and the precipitate was filtered off. The precipitate was purified by MPLC (Hyperprep HS C18, 8 µm, gradient 0.15% formic acid in water/acetonitrile 10/90→90/10 v/v). 2 fractions were isolated. Fraction 1: yield: 0.48 g (10% of theoretical); $C_{29}H_{30}ClN_3O_2$ (M=488.020) molpeak (M+H)$^+$: 488/490 (Cl); found: molpeak (M+H)$^+$: 488/490 (Cl); $R_f$ value: 0.60 (silica gel, PE/EtOAc 1:1).

EXAMPLE 38.1

2-{4-[5-(4-chlorophenyl)pyridin-2-ylethynyl]phenoxy}-N,N-diethylbenzamide

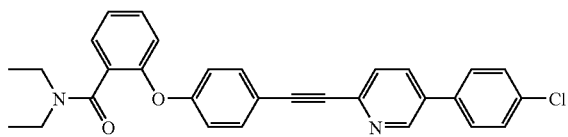

The product was obtained as fraction 2 in the synthesis of Example 37.1. Fraction 2: yield: 0.30 g (6% of theoretical); $C_{30}H_{25}ClN_2O_2$ (M=480.984); calc.: molpeak (M+H)$^+$: 481/483 (Cl); found: molpeak (M+H)$^+$: 481/483 (Cl); R$_f$ value: 0.40 (silica gel, PE/EtOAc 1:1).

EXAMPLE 39.1 cis-4-methyl-1-(6-{4-[2-(4-methylpiperidin-1-yl)ethoxy]phenylethynyl}pyridin-3-yl)cyclohexanol

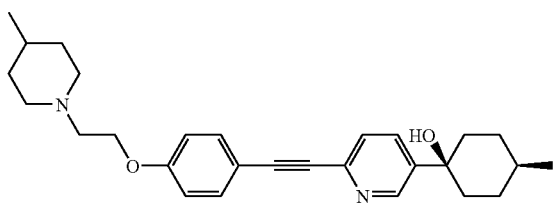

39.1a. 1-{6-[(tert-butyldimethylsilanyl)ethynyl]pyridin-3-yl}-4-methylcyclohexanol 9.5 mL (16.19 mmol) of n-BuLi (1.6 M in THF) was slowly added under argon at −70° C. to a solution of 4.50 g (15.19 mmol) of 5-bromo-2-[(tert-butyldimethylsilanyl)ethynyl]pyridine in 50 mL of diethyl ether and 60 mL of THF and after the addition had ended the mixture was stirred for another 2 minutes. 1.86 mL (15.19 mmol) of 4-methylcyclohexanone was added and the mixture was slowly heated to RT. 150 mL of saturated aqueous ammonium chloride solution were added and the aqueous phase was exhaustively extracted with EtOAc. The combined organic extracts were with washed with semisaturated aqueous sodium bicarbonate solution, dried over magnesium sulfate, and evaporated down in vacuo. The residue was purified by chromatography (silica gel, PE/EtOAc 4:1). 2 fractions were isolated. Fraction 1: cis-1-{6-[(tert-butyldimethylsilanyl)ethynyl]pyridin-3-yl}-4-methylcyclohexanol; yield: 1.40 g (28% of theoretical); $C_{20}H_{31}NOSi$ (M=329.552); calc.: molpeak (M+H)$^+$: 330; found: molpeak (M+H)$^+$: 330; R$_f$ value: 0.40 (silica gel, PE/EtOAc 4:1). Fraction 2: trans-1-{6-[(tert-butyldimethylsilanyl)ethynyl]pyridin-3-yl}-4-methylcyclohexanol; yield: 1.00 g (20% of theoretical); $C_{20}H_{31}NOSi$ (M=329.552); calc.: molpeak (M+H)$^+$: 330; found: molpeak (M+H)$^+$: 330; R$_f$ value: 0.30 (silica gel, PE/EtOAc 4:1).

39.1b. cis-1-(6-ethynylpyridin-3-yl)-4-methylcyclohexanol

The product was obtained analogously to Example 7.1d starting from cis-1-{6-[(tert-butyldimethylsilanyl)ethynyl]pyridin-3-yl}-4-methylcyclohexanol (Example 30.1a, fraction 1). Yield: 1.10 g (99% of theoretical); $C_{14}H_{17}NO$ (M=215.291); calc.: molpeak (M+H)$^+$: 216; found: molpeak (M+H)$^+$: 216; R$_f$ value: 0.55 (silica gel, PE/EtOAc 1:1).

39.1c. cis-4-methyl-1-(6-{4-[2-(4-methylpiperidin-1-yl)ethoxy]phenylethynyl}pyridin-3-yl)cyclohexanol The product was obtained analogously to Example 7.1e starting from 1-[2-(4-iodophenoxy)ethyl]-4-methylpiperidine and cis-1-(6-ethynylpyridin-3-yl)-4-methylcyclohexanol. Yield: 1.10 g (50% of theoretical); $C_{28}H_{36}N_2O_2$ (M=432.598); calc.: molpeak (M+H)$^+$: 433; found: molpeak (M+H)$^+$: 433; HPLC-MS: 4.70 minutes (method B).

EXAMPLE 40.1 trans-4-methyl-1-(6-{4-[2-(4-methylpiperidin-1-yl)ethoxy]phenylethynyl}pyridin-3-yl)cyclohexanol

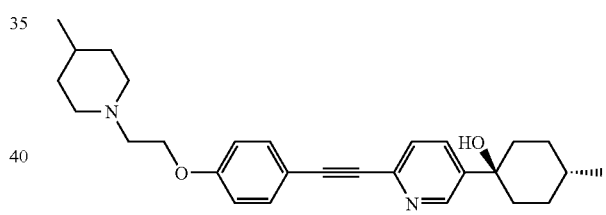

40.1b. trans-1-(6-ethynylpyridin-3-yl)-4-methylcyclohexanol

The product was obtained analogously to Example 7.1d starting from trans-1-{6-[(tert-butyldimethylsilanyl)ethynyl]pyridin-3-yl}-4-methylcyclohexanol (Example 39.1a, fraction 2). Yield: 0.50 g (77% of theoretical); $C_{14}H_{17}NO$ (M=215.291); calc.: molpeak (M+H)$^+$:216; found: molpeak (M+H)$^+$:216; R$_f$ value: 0.45 (silica gel, PE/EtOAc 1:1).

40.1c. trans-4-methyl-1-(6-{4-[2-(4-methylpiperidin-1-yl)ethoxy]phenylethynyl}pyridin-3-yl)cyclohexanol The product was obtained analogously to Example 7.1e starting from 1-[2-(4-iodophenoxy)ethyl]-4-methylpiperidine and trans-1-(6-ethynylpyridin-3-yl)-4-methylcyclohexanol. Yield: 0.40 g (40% of theoretical); $C_{28}H_{36}N_2O_2$ (M=432.598); calc.: molpeak (M+H)$^+$:433; found: molpeak (M+H)$^+$:433; HPLC-MS: 4.60 minutes (method B).

EXAMPLE 41.1

1-{5-[5-(4-chlorophenyl)pyridin-2-ylethynyl]-2-[2-(4-methylpiperidin-1-yl)ethoxy]phenyl}-2,2,2-trifluoroethanol

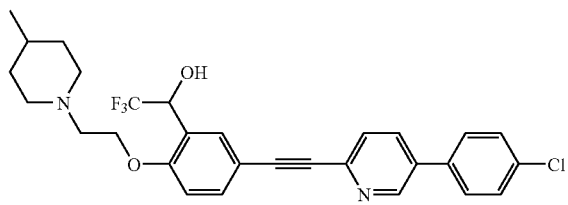

0.523 mL (1.05 mmol) of trimethyltrifluoromethylsilane (2M in THF) was slowly added dropwise at −10° C. to a solution of 0.39 g (0.85 mmol) of 5-[5-(4-chlorophenyl)pyridin-2-ylethynyl]-2-[2-(4-methylpiperidin-1-yl)ethoxy]benzaldehyde (Example 14.1c) and 13 mg (0.087 mmol) of cesium fluoride in 10 mL of THF and the reaction mixture was stirred for 2 hours at −10° C. 7 mL of 1M aqueous HCl were added and the mixture was stirred. The reaction mixture was made alkaline by the addition of saturated aqueous potassium carbonate solution and the phases were separated. The aqueous phase was extracted with EtOAc, and the combined organic extracts were dried over magnesium sulfate and evaporated down in vacuo. The crude product was purified by chromatography (silica gel, EtOAc/MeOH/sat. aqueous ammonia 95:5:0.5). Yield: 25 mg (5% of theoretical); $C_{29}H_{28}ClF_3N_2O_2$ (M=528.993); calc.: $(M+H)^+$:529/531 (Cl); found: molpeak $(M+H)^+$:529/531 (Cl); HPLC-MS: 5.95 minutes (method B).

EXAMPLE 42.1

{4-[5-(4-chlorophenyl)pyridin-2-ylethynyl]phenyl}-(S)-1-pyrrolidin-2-ylmethylamine

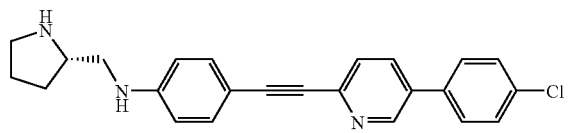

42.1a.
(4-bromophenyl)-(S)-1-pyrrolidin-2-ylmethylamine 2.45 g (10.00 mmol) of potassium phosphate monohydrate was added under argon to a mixture of 1.42 g (5.00 mmol) of 1-bromo-4-iodobenzene, 1.00 g (5.00 mmol) of tert-butyl (S)-2-aminomethylpyrrolidine-1-carboxylate, 48 mg (0.25 mmol) of CuI, and 97 mg (0.50 mmol) of N,N-diethylsalicylamide in 5 mL of DMF and the mixture was stirred for 160 hours at 100° C. The reaction mixture was cooled to RT, combined with 100 mL of 4M aqueous HCl, and stirred for 1 hour at RT. The aqueous phase was washed with MTBE, made basic with concentrated aqueous ammonia, and exhaustively extracted with MTBE. The combined organic extracts were dried over magnesium sulfate, filtered through activated charcoal, and evaporated down in vacuo. The crude product was purified by MPLC (Hyperprep HS C18, 8 µm, gradient 0.15% formic acid in water/acetonitrile 10/90→90/10 v/v). The eluates were evaporated down in vacuo and the residue was neutralized with sat. aqueous sodium bicarbonate solution. The aqueous phase was extracted with DCM, dried over magnesium sulfate and evaporated down in vacuo. Yield: 0.20 g (16% of theoretical); $C_{11}H_{15}BrN_2$ (M=255.2); calc.: molpeak $(M+H)^+$: 255/257 (Br); found: molpeak $(M+H)^+$:255/257 (Br); HPLC-MS: 3.90 minutes (method B).

42.1b.
(4-iodophenyl)-(S)-1-pyrrolidin-2-ylmethylamine

The product was prepared analogously to Example 20.1b starting from (4-bromophenyl)-(S)-1-pyrrolidin-2-ylmethylamine. Yield: 0.24 g (quant. yield); $C_{11}H_{15}IN_2$ (M=302.2); calc.: molpeak $(M+H)^+$:303; found: molpeak $(M+H)^+$:303; HPLC-MS: 5.50 minutes (method A).

42.1c. {4-[5-(4-chlorophenyl)pyridin-2-ylethynyl]phenyl}-(S)-1-pyrrolidin-2-ylmethylamine The product was obtained analogously to Example 7.1e starting from (4-iodophenyl)-(S)-1-pyrrolidin-2-ylmethylamine and 5-(4-chlorophenyl)-2-ethynylpyridine. The crude product was purified by MPLC (Hyperprep HS C18, 8 µm, gradient 0.15% formic acid in water/acetonitrile 10/90→90/10 v/v). The eluates were evaporated down in vacuo and the residue was neutralized with sat. aqueous sodium bicarbonate solution. The aqueous phase was extracted with DCM, dried over magnesium sulfate and evaporated down in vacuo. Yield: 35 mg (11% of theoretical); $C_{24}H_{22}ClN_3$ (M=387.904); calc.: molpeak $(M+H)^+$:388/390 (Cl); found: molpeak $(M+H)^+$: 388/390 (Cl); HPLC-MS: 5.0 minutes (method B).

EXAMPLE 43.1

(5-(4-chlorophenyl)-2-{4-[2-(4-methylpiperidin-1-yl)ethoxy]phenylethynyl}pyridin-3-yl)methylamine

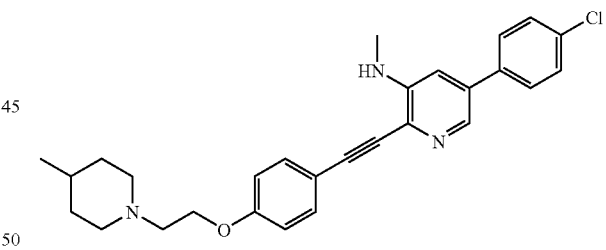

43.1a. [2-bromo-5-(4-chlorophenyl)pyridin-3-yl]methylamine 1.32 mL (17.63 mmol) of formalin solution (37% in water) and 443 mg (7.05 mmol) of sodium cyanoborohydride were added to a solution of 0.50 g (1.76 mmol) of 2-bromo-5-(4-chlorophenyl)pyridin-3-ylamine (Example 16.1c) in 20 mL of acetonitrile, the mixture was acidified to pH 4 with HOAc, and stirred for 16 hours at RT. The reaction mixture was acidified with 4M aqueous HCl and stirred for 1 hour at RT. It was made alkaline with sat. aqueous sodium carbonate solution and the aqueous phase was exhaustively extracted with DCM. The combined organic phases were dried over magnesium sulfate and evaporated down in vacuo. The residue was purified by chromatography (silica gel, gradient PE/DCM 50:50→100:0). Yield: 0.24 g (46% of theoretical); $C_{12}H_{10}BrClN_2$ (M=297.578); calc.: molpeak $(M+H)^+$: 297/299/301 (BrCl); found: molpeak $(M+H)^+$:297/299/301 (BrCl); HPLC-MS: 6.09 minutes (method B).

43.1b. [5-(4-chlorophenyl)-2-trimethylsilanylethynylpyridin-3-yl]methylamine

The product was prepared analogously to Example 7.1c starting from [2-bromo-5-(4-chlorophenyl)pyridin-3-yl]methylamine and trimethylsilylacetylene. Yield: 0.23 g (91% of theoretical); $C_{17}H_{19}ClN_2Si$ (M=314.884); calc.: molpeak $(M+H)^+$:315/317 (Cl); found: molpeak $(M+H)^+$:315/317 (Cl).

43.1c. [5-(4-chlorophenyl)-2-ethynylpyridin-3-yl]methylamine

The product was prepared analogously to Example 7.1d starting from [5-(4-chlorophenyl)-2-trimethylsilanylethynylpyridin-3-yl]methylamine. Yield: 0.18 g (quant. yield); $C_{14}H_{11}ClN_2$ (M=242.703); calc.: molpeak $(M+H)^+$:243/245 (Cl); found: molpeak $(M+H)^+$:243/345 (Cl); HPLC-MS: 5.40 minutes (method B).

43.1d. (5-(4-chlorophenyl)-2-{4-[2-(4-methylpiperidin-1-yl)ethoxy]phenylethynyl}pyridin-3-yl)methylamine The product was prepared analogously to Example 7.1e starting from 1-[2-(4-iodophenoxy)ethyl]-4-methylpiperidine and [5-(4-chlorophenyl)-2-ethynylpyridin-3-yl]methylamine. Yield: 70 mg (21% of theoretical); $C_{28}H_{30}ClN_3O$ (M=460.010); calc.: molpeak $(M+H)^+$:460/462 (Cl); found: molpeak $(M+H)^+$:460/462 (Cl); HPLC-MS: 5.30 minutes (method D).

EXAMPLE 44.1

(5-(4-chlorophenyl)-2-{4-[2-(4-methylpiperidin-1-yl)ethoxy]phenylethynyl}pyridin-3-yl)dimethylamine

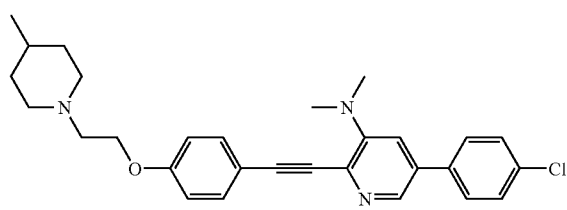

44.1a. [2-bromo-5-(4-chlorophenyl)pyridin-3-yl]dimethylamine 169 mg (3.88 mmol) of sodium hydride (55% suspension) was added batchwise under a nitrogen atmosphere to a solution of 0.50 g (1.76 mmol) of 2-bromo-5-(4-chlorophenyl)pyridin-3-ylamine (Example 16.1c) in 10 mL of DMF and the mixture was stirred for 15 minutes at RT. A solution of 0.22 mL (3.53 mmol) of methyl iodide in 0.5 mL of DMF was added and the mixture was stirred for 16 hours at RT. The reaction mixture was diluted with semisaturated aqueous sodium bicarbonate solution and the aqueous phase was extracted with EtOAc. The combined organic extracts were washed with water, dried over magnesium sulfate, and evaporated down in vacuo. Yield: 0.47 g (85% of theoretical); $C_{13}H_{12}BrClN_2$ (M=311.605); calc.: molpeak $(M+H)^+$: 311/313/315 (BrCl); found: molpeak$(M+H)^+$:311/313/315 (BrCl).

44.1b. [5-(4-chlorophenyl)-2-trimethylsilanylethynylpyridin-3-yl]dimethylamine

The product was prepared analogously to Example 7.1c starting from [2-bromo-5-(4-chlorophenyl)pyridin-3-yl]dimethylamine and trimethylsilylacetylene. Yield: 0.50 g (quant. yield); $C_{18}H_{21}ClN_2Si$ (M=328.911); calc.: molpeak $(M+H)^+$: 329/331 (Cl); found: molpeak $(M+H)^+$:329/331 (Cl); HPLC-MS: 7.41 minutes (method B).

44.1c. [5-(4-chlorophenyl)-2-ethynylpyridin-3-yl]dimethylamine

The product was prepared analogously to Example 7.1d starting from [5-(4-chlorophenyl)-2-trimethylsilanylethynylpyridin-3-yl]dimethylamine. Yield: 0.39 g (quant. yield); $C_{15}H_{13}ClN_2$ (M=256.730); calc.: molpeak $(M+H)^+$:257/259 (Cl); found: molpeak $(M+H)^+$:257/259 (Cl); HPLC-MS: 5.80 minutes (method B).

44.1d. (5-(4-chlorophenyl)-2-{4-[2-(4-methylpiperidin-1-yl)ethoxy]phenylethynyl}pyridin-3-yl)dimethylamine The product was prepared analogously to Example 7.1 e starting from 1-[2-(4-iodophenoxy)ethyl]-4-methylpiperidine and [5-(4-chlorophenyl)-2-ethynylpyridin-3-yl]dimethylamine. Yield: 34 mg (5% of theoretical); $C_{29}H_{32}ClN_3O$ (M=474.037); calc.: molpeak $(M+H)^+$:474/476 (Cl); found: molpeak $(M+H)^+$:474/476 (Cl); HPLC-MS: 5.40 minutes (method D).

EXAMPLE 45.1

5-(4-methylcyclohex-1-enyl)-2-{4-[2-(4-methylpiperidin-1-yl)ethoxy]phenylethynyl}pyridine

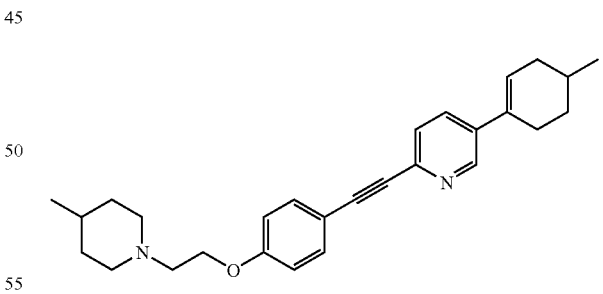

0.15 mL (2.08 mmol) of thionyl chloride was added at RT to a solution of 0.30 g (0.69 mmol) of cis-4-methyl-1-(6-{4-[2-(4-methylpiperidin-1-yl)ethoxy]phenylethynyl}pyridin-3-yl)cyclohexanol (Example 40.1c) in 40 mL of toluene and the mixture was heated to 100° C. for 2 hours. The reaction mixture was cooled to RT, filtered, and the filtrate was diluted with DCM. The organic phase was washed with semisaturated aqueous sodium bicarbonate solution, dried over magnesium sulfate, and evaporated down in vacuo. The residue was triturated with acetonitrile and a little MeOH, and the precipitate was filtered off and dried in vacuo. Yield: 90 mg (31% of theoretical); $C_{28}H_{34}N_2O$ (M=414.582); calc.: molpeak $(M+H)^+$:415; found: molpeak $(M+H)^+$:415; $R_f$ value: 0.35 (silica gel, DCM/MeOH 9:1).

EXAMPLE 46.1

N'-{5-[5-(4-chlorophenyl)pyridin-2-ylethynyl]pyridin-2-yl}-N,N-bis-cyclopropylmethylethane-1,2-diamine

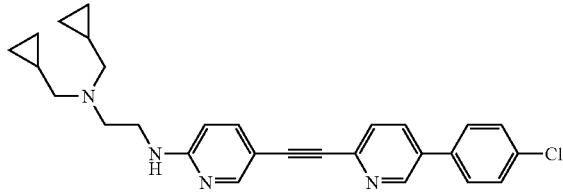

46.1a. tert-butyl [2-(5-bromopyridin-2-ylamino)ethyl]carbamate

A mixture of 8.86 g (31.20 mmol) of 5-bromo-2-iodopyridine and 10.00 g (62.42 mmol) of tert-butyl (2-aminoethyl) carbamate was stirred for 3 hours at 170° C. The reaction mixture was cooled to RT and diluted with EtOAc. The organic phase was washed with saturated aqueous sodium bicarbonate solution, dried over magnesium sulfate, and evaporated down in vacuo. The crude product was purified by chromatography (silica gel, cyc/EtOAc 4:1). Yield: 2.37 g (24% of theoretical); $C_{12}H_{18}BrN_3O_2$ (M=316.194); calc.: molpeak $(M+H)^+$:316/318 (Br); found: molpeak $(M+H)^+$: 316/318 (Br); $R_f$ value: 0.22 (silica gel, cyc/EtOAc 2:1).

46.1b. [2-(5-iodopyridin-2-ylamino)ethyl]carbamate tert-butyl

The product was obtained analogously to Example 20.1b starting from tert-butyl [2-(4-bromophenylamino)ethyl]carbamate. Yield: 2.76 g (quant. yield); $C_{12}H_{18}IN_3O_2$ (M=363.195); calc.: molpeak $(M+H)^+$:364; found: molpeak $(M+H)^+$:364; HPLC-MS: 6.20 minutes (method A).

46.1c. tert-butyl (2-{5-[5-(4-chlorophenyl)pyridin-2-ylethynyl]pyridin-2-ylamino}ethyl)carbamate The product was obtained analogously to Example 7.1 e starting from tert-butyl [2-(4-iodophenylamino)ethyl]carbamate and 5-(4-chlorophenyl)-2-ethynylpyridine. Yield: 2.39 g (70% of theoretical); $C_{25}H_{25}ClN_4O_2$ (M=448.944); calc.: molpeak $(M+H)^+$449/451 (Cl); molpeak $(M+H)^+$:449/451 (Cl); HPLC-MS: 8.90 minutes (method A).

46.1d. $N^1$-{5-[5-(4-chlorophenyl)pyridin-2-ylethynyl]pyridin-2-yl}ethan-1,2-diamine A solution of 2.39 g (5.32 mmol) of tert-butyl (2-{4-[5-(4-chlorophenyl)pyridin-2-ylethynyl]phenylamino}ethyl)carbamate and 8.15 mL (106.50 mmol) of TFA in 100 mL of DCM was stirred for 7.5 hours at RT and then made alkaline with 15% aqueous NaOH and saturated aqueous potassium carbonate solution. The precipitate formed was filtered off, washed with water, and stirred with DIPE. Yield: 1.43 g (77% of theoretical); $C_{20}H_{17}ClN_4$ (M=348.829); calc.: molpeak $(M+H)^+$:348/350 (Cl); found: molpeak $(M+H)^+$:348/350 (Cl); HPLC-MS: 6.70 minutes (method A).

46.1e. N'-{5-[5-(4-chlorophenyl)pyridin-2-ylethynyl]pyridin-2-yl}-N,N-bis-cyclopropylmethylethan-1,2-diamine A solution of 0.75 g (2.15 mmol) of N'-{4-[5-(4-chlorophenyl)pyridin-2-ylethynyl]phenyl}ethan-1,2-diamine and 0.16 mL (2.15 mmol) of cyclopropanecarbaldehyde in 60 mL of THF was stirred for 1 hour at RT, then combined with 1.82 g (8.60 mmol) of sodium triacetoxyborohydride, and 0.49 mL (8.60 mmol) of glacial acetic acid and stirred for a further 16 hours at RT. The reaction mixture was evaporated down in vacuo, combined with DCM, and filtered. The filtrate was washed with semisaturated aqueous sodium bicarbonate solution, dried over sodium sulfate, and evaporated down in vacuo. The crude product was purified by HPLC-MS (Zorbax Bonus C18 amide-phase 5 µm, gradient 0.15% formic acid in water/acetonitrile 10/90→90/10 v/v) and the product fractions were lyophilized. Yield: 212 mg (22% of theoretical); $C_{28}H_{29}ClN_4$ (M=457.010); calc.: molpeak $(M+H)^+$:457/459 (Cl); found: molpeak $(M+H)^+$:457/459 (Cl); HPLC-MS: 5.80 minutes (method B).

EXAMPLE 47.1

4-{4-[5-(4-chlorophenyl)pyridin-2-ylethynyl]phenyl}-1-cyclopropylmethylpiperidin-4-ol

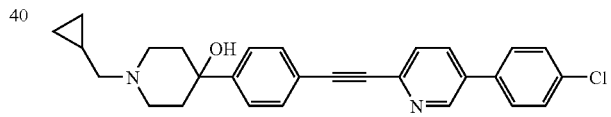

47.1a. 4-(4-iodophenyl)piperidin-4-ol

The product was obtained analogously to Example 20.1b starting from 4-(4-bromophenyl)piperidin-4-ol. Yield: 3.54 g (60% of theoretical); $C_{11}H_{14}INO$ (M=303.139); calc.: molpeak $(M+H)^+$:304; found: molpeak $(M+H)^+$:304; $R_f$ value: 0.17 (silica gel, EtOAc/MeOH/sat. aqueous ammonia 6:4: 0.4).

47.1b. 4-{4-[5-(4-chlorophenyl)pyridin-2-ylethynyl]phenyl}piperidin-4-ol

The product was obtained analogously to Example 7.1e starting from 4-(4-iodophenyl)piperidin-4-ol and 5-(4-chlorophenyl)-2-ethynylpyridine. Yield: 0.78 g (61% of theoretical); $C_{24}H_{21}ClN_2O$ (M=388.889); calc.: molpeak $(M+H)^+$: 389/391 (Cl); found: molpeak $(M+H)^+$:389/391 (Cl); $R_f$ value: 0.86 (silica gel, EtOAc/cyc 4:1).

47.1c. 4-{4-[5-(4-chlorophenyl)pyridin-2-ylethynyl]phenyl}-1-cyclopropylmethylpiperidin-4-ol A solution of 0.78 g (2.02 mmol) of 4-{4-[5-(4-chlorophenyl)pyridin-2-ylethynyl]phenyl}piperidin-4-ol and 0.59 mL (8.06 mmol) of cyclopropanecarbaldehyde in 40 mL of THF was stirred for 30 minutes at RT, then combined with 1.71 g (8.06 mmol) of sodium triacetoxyborohydride and 0.46 mL (8.06 mmol) of glacial acetic acid and stirred for a further 2 days at RT. The reaction mixture was combined with DCM, and the organic phase was washed with semisaturated aqueous sodium bicarbonate solution, dried over sodium sulfate, and evaporated down in vacuo. The crude product was stirred with isopropanol, and the precipitate was filtered off and dried in vacuo. Yield: 0.19 g (21% of theoretical); $C_{28}H_{27}ClN_2O$ (M=442.980); calc.: molpeak $(M+H)^+$:443/445 (Cl); found: molpeak $(M+H)^+$:443/445 (Cl); HPLC-MS: 7.26 minutes (method A).

EXAMPLE 48.1

1-(2-{4-[5-(4-chlorophenyl)pyrazin-2-ylethynyl]phenoxy}ethyl)-4-trifluoromethylpiperidin-4-ol

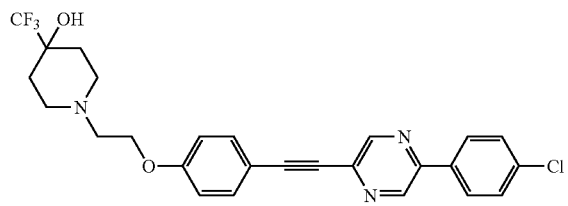

48.1a. 5-(4-chlorophenyl)pyrazin-2-ylamine 50 mL of 2N sodium carbonate solution and 1.16 g (1.00 mmol) of $Pd(PPh_3)_4$ were added to a solution of 8.70 g (174 mmol) of 5-bromopyrazin-2-ylamine and 7.98 g (156 mmol) of 4-chlorophenylboric acid in 150 mL of 1,4-dioxane and 50 mL of MeOH and the mixture was heated to 110° C. for 2.5 hours. The reaction mixture was evaporated down in vacuo and diluted with EtOAc. The organic phase was washed with water, dried over sodium sulfate, and evaporated down in vacuo. The residue was purified by column chromatography (silica gel, DCM→DCM/MeOH 20:1). Yield: 8.30 g (81% of theoretical); $C_{10}H_8ClN_3$ (M=205.643); calc.: molpeak $(M+H)^+$:206/208 (Cl); found: molpeak $(M+H)^+$:206/208 (Cl); HPLC-MS: 7.15 minutes (method G).

48.1b. 2-(4-chlorophenyl)-5-iodopyrazine

In a flask protected from light, 4.90 mL (40.0 mmol) of tert-butylnitrite and 7.61 g (30.0 mmol) of iodine were added to a solution of 4.80 g (23.5 mmol) of 5-(4-chlorophenyl)pyrazin-2-ylamine in 100 mL of carbon tetrachloride and 50 mL of DCM. The mixture was stirred overnight at RT and then combined with 100 mL of water. The organic phase was washed twice with 50 mL of 10% aqueous sodium thiosulfate solution and 50 mL of water, dried over magnesium sulfate, filtered through activated charcoal, and evaporated down in vacuo. The residue was purified by column chromatography (silica gel, PE→PE/EtOAc 8:2). Yield: 3.40 g (46% of theoretical); $C_{10}H_6ClIN_2$ (M=316.525); calc.: molpeak $(M+H)^+$:317/319 (Cl); found: molpeak $(M+H)^+$:317/319 (Cl); $R_f$ value: 0.55 (silica gel, PE/EtOAc 9:1).

48.1c. 2-{4-[5-(4-chlorophenyl)pyrazin-2-ylethynyl]phenoxy}ethanol

Under an argon atmosphere 49 mg (0.06 mmol) of $PdCl_2$(dppf) and 11 mg (0.06 mmol) of CuI were added to a repeatedly degassed solution of 535 mg (3.30 mmol) of 2-(4-chlorophenyl)-5-iodopyrazine, 950 mg (3.30 mmol) of 2-(4-ethynylphenoxy)ethanol, and 0.59 mL (6.00 mmol) of piperidine in 50 mL of THF and the mixture was stirred for 4 hours at RT. The precipitate was suction filtered and washed with acetonitrile. The mother liquor was concentrated, and the precipitate formed was filtered off and washed with acetonitrile. The precipitates were combined. Yield: 700 mg (67% of theoretical); $C_{20}H_{15}ClN_2O_2$ (M=350.798); calc.: molpeak $(M+H)^+$:351/353 (Cl); found: molpeak $(M+H)^+$:351/353 (Cl); $R_f$ value: 0.30 (silica gel, PE/EtOAc 1:1).

48.1d. 2-{4-[5-(4-chlorophenyl)pyrazin-2-ylethynyl]phenoxy}ethyl methanesulfonate 0.62 mL (7.98 mmol) of methanesulfonic acid chloride was added dropwise at RT to a solution of 700 mg (2.00 mmol) of 2-{4-[5-(4-chlorophenyl)pyrazin-2-ylethynyl]phenoxy}ethanol and 0.65 mL (7.98 mmol) of pyridine in 20 mL of DCM and the mixture was then stirred overnight at RT. After the addition of another 0.33 mL (3.99 mmol) of pyridine and 0.32 mL (4.12 mmol) of methanesulfonic acid chloride, the reaction mixture was stirred for a further 2 hours at RT in the ultrasound bath. The solution was diluted with 30 mL DCM, and the organic phase was separated off, washed three times with 60 mL of water, and dried over magnesium sulfate. After the desiccant and solvent had been eliminated, the residue was purified by chromatography (silica gel, DCM). Yield: 600 mg (70% of theoretical); $C_{21}H_{17}ClN_2O_4S$ (M=428.889); calc.: molpeak $(M+H)^+$:429/431 (Cl); found: molpeak $(M+H)^+$:429/431 (Cl); $R_f$ value: 0.30 (silica gel, DCM/MeOH 9:1).

48.1e. 1-(2-{4-[5-(4-chlorophenyl)pyrazin-2-ylethynyl]phenoxy}ethyl)-4-trifluoromethylpiperidin-4-ol The product was prepared analogously to Example 1.1g starting from 64 mg (0.15 mmol) 2-{4-[5-(4-chlorophenyl)pyrazin-2-ylethynyl]phenoxy}ethyl methanesulfonate and 76 mg (0.45 mmol) 4-trifluoromethylpiperidin-4-ol. Yield: 33 mg (44% of theoretical); $C_{26}H_{23}ClF_3N_3O$ (M=501.928); calc.: molpeak $(M+H)^+$:502/504; found: molpeak $(M+H)^+$: 502/504; HPLC-MS: 5.25 minutes (method G).

The following Examples were prepared analogously starting from 2-{4-[5-(4-chlorophenyl)pyrazin-2-ylethynyl]phenoxy}ethyl methanesulfonate (Example 48.1d).

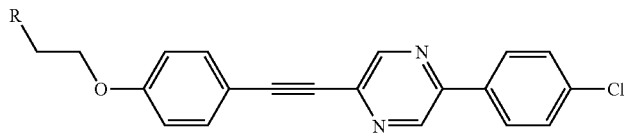

| Example | R | Yield (%) | empirical formula | mass spectrum | retention time HPLC in minutes (method) |
|---|---|---|---|---|---|
| 48.2 | HO-[4-methylpiperidinyl] | 36 | $C_{26}H_{26}ClN_3O_2$ | 448/450 $[M+H]^+$ | 5.0 (G) |
| 48.3 | 4,4-dimethylpiperidinyl | 33 | $C_{27}H_{28}ClN_3O$ | 446/448 $[M+H]^+$ | 5.9 (G) |
| 48.4 | 4-methylpiperidinyl | 54 | $C_{26}H_{26}ClN_3O$ | 432/434 $[M+H]^+$ | 5.7 (G) |
| 48.5 | cyclopentylamino | 37 | $C_{25}H_{24}ClN_3O$ | 418/420 $[M+H]^+$ | 5.8 (G) |

EXAMPLE 48.6

1-(2-{4-[5-(2,4-dichlorophenyl)pyrazin-2-ylethynyl]phenoxy}ethyl)-4-methylpiperidin-4-ol

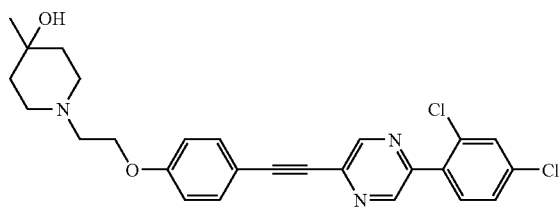

48.6a. 5-(2,4-dichlorophenyl)pyrazin-2-ylamine

The product was prepared analogously to Example 48.1a from 1.74 g (10.0 mmol) of 5-bromopyrazin-2-ylamine and 1.91 g (10.0 mmol) of 2,4-dichlorophenylboric acid. Yield: 800 mg (33% of theoretical); $C_{10}H_7Cl_2N_3$ (M=240.088); calc.: molpeak $(M+H)^+$240/242/244 (2 Cl); found: molpeak $(M+H)^+$:240/242/244 (2 Cl); $R_f$ value: 0.35 (silica gel, PE/EtOAc 7:3).

48.6b. 2-(2,4-dichlorophenyl)-5-iodopyrazine

The product was prepared analogously to Example 48.1b from 800 mg (3.33 mmol) of 5-(2,4-dichlorophenyl)pyrazin-2-ylamine. Yield: 450 mg (38% of theoretical); $C_{10}H_5Cl_2IN_2$ (M=350.970); calc.: molpeak $(M)^+$:350/352/354 (2 Cl); found: molpeak $(M)^+$:350/352/354 (2 Cl); $R_f$ value: 0.75 (silica gel, PE/EtOAc 9:1).

48.6c. 2-(2,4-dichlorophenyl)-5-trimethylsilanyl-ethynylpyrazine

The product was prepared analogously to Example 48.1c from 450 mg (1.28 mmol) of 2-(2,4-dichlorophenyl)-5-iodopyrazine and 0.20 mL (1.41 mmol) of trimethylsilylacetylene (using triethylamine as base). Yield: 300 mg (73% of theoretical); $C_{15}H_{14}Cl_2N_2Si$ (M=321.276); calc.: molpeak $(M+H)^+$:321/323/325 (2 Cl); found: molpeak $(M+H)^+$:321/323/325 (2 Cl); $R_f$ value: 0.6 (silica gel, cyclohexane/EtOAc 9:1).

48.6d. 2-(2,4-dichlorophenyl)-5-ethynylpyrazine

The product was obtained analogously to Example 1.1c from 300 mg (0.93 mmol) of 2-(2,4-dichlorophenyl)-5-trimethylsilanylethynylpyrazine (30 minutes at RT, DCM as solvent). Yield: 180 mg (77% of theoretical); $C_{12}H_6Cl_2N_2$ (M=249.095); calc.: molpeak $(M+H)^+$:249/251/253 (2 Cl); found: molpeak $(M+H)^+$:249/251/253 (2 Cl); $R_f$ value: 0.8 (silica gel, PE/EtOAc 7:3).

48.6e. 1-(2-{4-[5-(2,4-dichlorophenyl)pyrazin-2-ylethynyl]phenoxy}ethyl)-4-methylpiperidin-4-ol The product was prepared analogously to Example 48.1c from 180 mg (0.72 mmol) of 2-(2,4-dichlorophenyl)-5-ethynylpyrazine and 260 mg (0.72 mmol) of 1-[2-(4-iodophenoxy)ethyl]-4-methylpiperidin-4-ol (IP 15) (stirring the reaction mixture overnight at RT). Yield: 16 mg (5% of theoretical); $C_{26}H_{25}Cl_2N_3O_2$ (M=482.401); calc.: molpeak (M+H)+482/484/486 (2 Cl); found: molpeak (M+H)+:482/484/486 (2 Cl); HPLC-MS: 7.5 minutes (method G).

EXAMPLE 48.7

1-(2-{4-[5-(4-chloro-2-methylphenyl)pyrazin-2-yl-ethynyl]phenoxy}ethyl)-4-methylpiperidin-4-ol

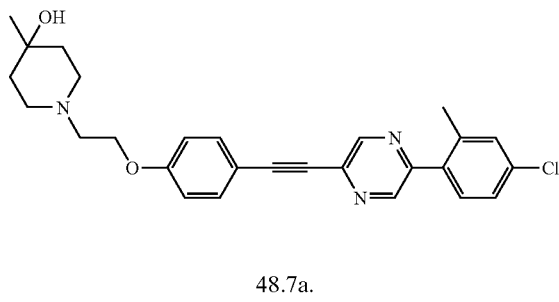

48.7a.
5-(4-chloro-2-methylphenyl)pyrazin-2-ylamine

The product was prepared analogously to Example 48.1a from 2.61 g (15.0 mmol) of 5-bromopyrazin-2-ylamine and 2.56 g (15.0 mmol) of 4-chloro-2-methylphenylboric acid. Yield: 1.70 g (52% of theoretical); $C_{11}H_{10}ClN_3$ (M=219.670); calc.: molpeak (M+H)+:220/222 (Cl); found: molpeak (M+H)+:220/222 (Cl); $R_f$ value: 0.35 (silica gel, PE/EtOAc 7:3).

48.7b. 2-(4-chloro-2-methylphenyl)-5-iodopyrazine

The product was prepared analogously to Example 48.1b from 1.70 g (7.74 mmol) of 5-(4-chloro-2-methylphenyl)pyrazin-2-ylamine. Yield: 1.70 g (66% of theoretical); $C_{11}H_8ClIN_2$ (M=330.552); calc.: molpeak (M+H)+:331/333 (Cl); found: molpeak (M+H)+:331/333 (Cl); $R_f$ value: 0.7 (silica gel, PE).

48.7c. 2-(4-chloro-2-methylphenyl)-5-trimethylsilanylethynylpyrazine

The product was prepared analogously to Example 48.1c from 1.70 g (5.14 mmol) of 2-(4-chloro-2-methylphenyl)-5-iodopyrazine and 0.80 mL (5.66 mmol) of trimethylsilylacetylene (using triethylamine as base). Yield: 700 mg (45% of theoretical); $C_{16}H_{17}ClN_2Si$ (M=300.858); calc.: molpeak (M+H)+:301/303 (Cl); found: molpeak (M+H)+:301/303 (Cl); $R_f$ value: 0.5 (silica gel, PE/EtOAc 9:1).

48.7d.
2-(4-chloro-2-methylphenyl)-5-ethynylpyrazine

The product was prepared analogously to Example 1.1c from 700 mg (2.33 mmol) of 2-(4-chloro-2-methylphenyl)-5-trimethylsilanylethynylpyrazine (40 minutes at RT, DCM as solvent). Yield: 200 mg (38% of theoretical); $C_{13}H_9ClN_2$ (M=228.677); calc.: molpeak (M+H)+:229/231 (Cl); found: molpeak (M+H)+:229/231 (Cl); $R_f$ value: 0.2 (silica gel, PE/EtOAc 9:1).

48.7e. 1-(2-{4-[5-(4-chloro-2-methylphenyl)pyrazin-2-ylethynyl]phenoxy}ethyl)-4-methylpiperidin-4-ol The product was prepared analogously to Example 48.1c from 200 mg (0.88 mmol) of 2-(4-chloro-2-methylphenyl)-5-ethynylpyrazine and 316 mg (0.88 mmol) of 1-[2-(4-iodophenoxy)ethyl]-4-methylpiperidin-4-ol (IP 15) (stirring the reaction mixture overnight at RT). Yield: 30 mg (7% of theoretical); $C_{27}H_{28}ClN_3O_2$ (M=461.983); calc.: molpeak (M+H)+:462/464 (Cl); found: molpeak (M+H)+:462/464 (Cl); HPLC-MS: 5.43 minutes (method G; Zorbax-Bonus).

EXAMPLE 49.1

3-fluoro-5-(4-methylcyclohex-1-enyl)-2-{4-[2-(4-methylpiperidin-1-yl)ethoxy]phenylethynyl}pyridine

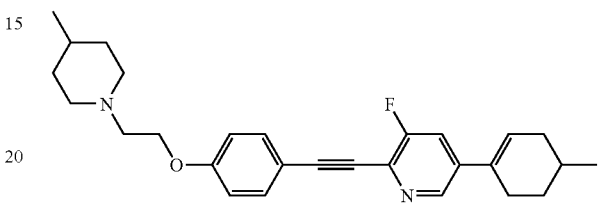

49.1a. 5-bromo-2-[(tert-butyldimethylsilanyl)ethynyl]-3-fluoropyridine

The product was prepared analogously to Example 48.1c from 23.4 g (92.0 mmol) of 2,5-dibromo-3-fluoropyridine and 17.5 mL (92.0 mmol) of tert-butylethynyldimethylsilane (with triethylamine as base and $PdCl_2(PPh_3)_2$ as catalyst). Yield: 23.3 g (81% of theoretical); $C_{13}H_{17}BrFNSi$ (M=314.269); calc.: molpeak (M+H)+:314/316 (Br); found: molpeak (M+H)+:314/316 (Br).

49.1b. 1-{6-[(tert-butyldimethylsilanyl)ethynyl]-5-fluoropyridin-3-yl}-4-methylcyclohexanol Under an argon atmosphere 9.38 mL (15.0 mmol, 1.6 M) of n-butyllithium was slowly added to a solution of 4.71 g (15.0 mmol) of 5-bromo-2-[(tert-butyldimethylsilanyl)ethynyl]-3-fluoropyridine in 100 mL of diethyl ether at –70° C., so that the internal temperature did not rise above –65° C. After 2 minutes, 1.84 mL (15.0 mmol) of 4-methylcyclohexanone was added and then the cooling bath was removed. The reaction solution was heated to RT and then combined with 50 mL of aqueous saturated ammonium chloride solution. The organic phase was separated off, the aqueous phase was extracted twice with MTBE, and the combined organic phases were dried over magnesium sulfate, filtered through activated charcoal, and the solvent was removed in vacuo. The residue was taken up in DIPE, cooled in the cooling bath, and the precipitate formed (1.4 g) was suction filtered. The mother liquor was concentrated in vacuo and the residue was purified by column chromatography (silica gel, PE/EtOAc 8:2). A further 2.1 g were obtained, which were combined with the above precipitate. The product was obtained as a cis/trans mixture. Yield: 3.50 g (67% of theoretical); $C_{20}H_{30}FNOSi$ (M=347.542); calc.: molpeak (M+H)+:348; found: molpeak (M+H)+:348; $R_f$ value: 0.5 (silica gel, PE/EtOAc 8:2).

49.1c. 2-ethynyl-3-fluoro-5-(4-methylcyclohex-1-enyl)pyridine 0.28 mL (2.00 mmol) of triethylamine was added to a solution of 348 mg (1.00 mmol) of 1-{6-[(tert-butyldimethylsilanyl)ethynyl]-5-fluoropyridin-3-yl}-4-methylcyclohexanol in 15 mL of DCM and then 0.15 mL (2.00 mmol) of methanesulfonic acid chloride was added dropwise while the mixture was cooled. The reaction was stirred for 2 hours at RT and then a further 0.15 mL (2.00 mmol) of methanesulfonic acid chloride were added and the mixture was stirred for 1 hour at RT. A further 0.58 mL (4.00 mmol) of triethylamine was added and the mixture was stirred for 1 hour at RT. The reaction mixture was combined with 50 mL of ice water. The organic phase was separated off, washed with water, and the solvent was removed in vacuo. The residue was dissolved in 25 mL of DCM and combined with 315 mg (1.00 mmol) of TBAF. The solution was stirred for 30 minutes at RT and then combined with water. The organic phase was separated off, washed several times with water, dried over magnesium sulfate, and the solvent was eliminated in vacuo. Yield: 130 mg (45% of theoretical; 75% content of product); $C_{14}H_{14}FN$ (M=215.266); calc.: molpeak $(M+H)^+$:216; found: molpeak $(M+H)^+$:216.

49.1d. 3-fluoro-5-(4-methylcyclohex-1-enyl)-2-{4-[2-(4-methylpiperidin-1-yl)ethoxy]phenylethynyl}pyridine The product was prepared analogously to Example 48.1c from 130 mg (0.60 mmol) of 2-ethynyl-3-fluoro-5-(4-methylcyclohex-1-enyl)pyridine and 207 mg (0.60 mmol) of 1-[2-(4-iodophenoxy)ethyl]-4-methylpiperidine (Example 19.1 a) (24 at RT, triethylamine as base). Yield: 15 mg (6% of theoretical); $C_{28}H_{33}FN_2O$ (M=432.573); calc.: molpeak $(M+H)^+$: 433; found: molpeak $(M+H)^+$:433; HPLC-MS: 5.60 minutes (method H).

EXAMPLE 49.2

1-(2-{4-[3-fluoro-5-(4-methylcyclohex-1-enyl)pyridin-2-ylethynyl]phenoxy}ethyl)-4-methylpiperidin-4-ol

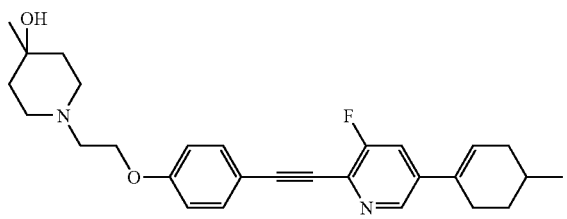

The product was prepared analogously to Example 48.1c from 130 mg (0.60 mmol) of 2-ethynyl-3-fluoro-5-(4-methylcyclohex-1-enyl)pyridine and 217 mg (0.60 mmol) of 1-[2-(4-iodophenoxy)ethyl]-4-methylpiperidin-4-ol (IP 15) (24 at RT, triethylamine as base). Yield: 15 mg (6% of theoretical); $C_{28}H_{33}FN_2O_2$ (M=448.572); calc.: molpeak $(M+H)^+$:449; found: molpeak $(M+H)^+$:449; HPLC-MS: 5.08 minutes (method H).

EXAMPLE 50.1

(2-{4-[5-(4-chlorophenyl)pyridin-2-ylethynyl]phenyl}ethyl)cyclopentylamine

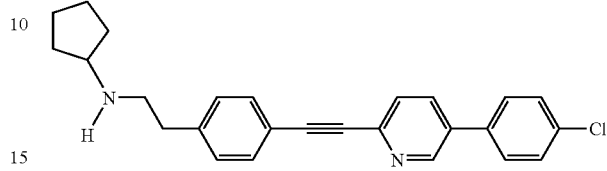

50.1a. 2-{4-[5-(4-chlorophenyl)pyridin-2-ylethynyl]phenyl}ethanol

The product was prepared analogously to Example 48.1c from 1.74 g (8.06 mmol) of 5-(4-chlorophenyl)-2-ethynylpyridine and 2.00 g (8.06 mmol) of 2-(4-iodophenyl)ethanol (24 at RT, triethylamine as base and acetonitrile as solvent). Yield: 1.80 g (67% of theoretical); $C_{21}H_{16}ClNO$ (M=333.811); calc.: molpeak $(M+H)^+$:334/336 (Cl); found: molpeak $(M+H)^+$:334/336 (Cl).

50.1b. 2-{4-[5-(4-chlorophenyl)pyridin-2-ylethynyl]phenyl}ethyl methanesulfonate 0.06 mL (0.75 mmol) of methanesulfonic acid chloride was added dropwise at 0° C. to a solution of 167 mg (0.50 mmol) of 2-{4-[5-(4-chlorophenyl)pyridin-2-ylethynyl]phenyl}ethanol and 0.08 mL (1.00 mmol) of pyridine in 5 mL of DCM and the mixture was then stirred for 1 hour at 0° C. It was combined again with pyridine (0.08 mL) and methanesulfonic acid chloride (0.06 mL) and stirred for 1 hour at RT. Then it was combined with 0.14 mL (1.00 mmol) of triethylamine and after 20 minutes at RT diluted with ice water. The organic phase was separated off, dried over magnesium sulfate, filtered, and the solvent was eliminated in vacuo. Yield: 185 mg (90% of theoretical); $C_{22}H_{18}ClNO_3S$ (M=411.902); calc.: molpeak $(M+H)^+$:412/414 (Cl); found: molpeak $(M+H)^+$:412/414 (Cl); HPLC-MS: 6.27 minutes (method H).

50.1c. (2-{4-[5-(4-chlorophenyl)pyridin-2-ylethynyl]phenyl}ethyl)cyclopentylamine The product was prepared analogously to Example 1.1g from 60 mg (0.15 mmol) of 2-{4-[5-(4-chlorophenyl)pyridin-2-ylethynyl]phenyl}ethyl methanesulfonate and 0.03 mL (0.30 mmol) of cyclopentylamine (6 hours at 50° C., potassium carbonate as base). Yield: 20 mg (34% of theoretical); $C_{26}H_{25}ClN_2$ (M=400.943); calc.: molpeak $(M+H)^+$:401/403 (Cl); found: molpeak $(M+H)^+$:401/403 (Cl); HPLC-MS: 5.0 minutes (method H).

The following Examples were prepared analogously starting from 2-{4-[5-(4-chlorophenyl)pyridin-2-ylethynyl]phenyl)}ethyl methanesulfonate (Example 50.1b):

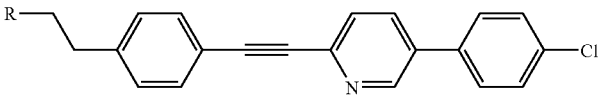

| Example | R | Yield (%) | empirical formula | mass spectrum | retention time HPLC in minutes (method) |
|---|---|---|---|---|---|
| 50.2 | HO-[4-methylpiperidin-1-yl]-* | 48 | $C_{27}H_{27}ClN_2O$ | 431/433 $[M + H]^+$ | 7.2 (G) |
| 50.3 | [4,4-dimethylpiperidin-1-yl]-* | 64 | $C_{28}H_{29}ClN_2$ | 429/31 $[M + H]^+$ | 5.4 (H) |
| 50.4 | [4-methylpiperidin-1-yl]-* | 41 | $C_{27}H_{27}ClN_2$ | 415/417 $[M + H]^+$ | 5.0 (H) |

EXAMPLE 50.5

5-(4-chlorophenyl)-2-{3-methyl-4-[2-(4-methylpiperidin-1-yl)ethyl]phenylethynyl}pyridine

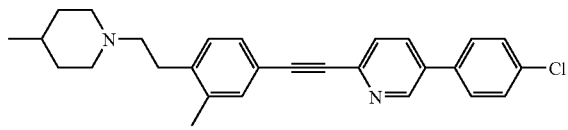

50.5a. tert-butyl(4-bromo-2-methylphenyl)acetate

Under an argon atmosphere 39.6 mL (39.6 mmol; 1M in hexane) of lithium-hexamethyldisilazane was added to a suspension of 145 mg (0.65 mmol) of palladium (II) acetate and 875 mg (2.22 mmol) of 2-dicyclohexylphosphino-2-(N,N-dimethylamino)biphenyl in 40 mL of toluene and the reaction solution was stirred for 10 minutes at RT. Then the mixture was cooled to −10° C. and combined with 3.30 mL (24.5 mmol) of tert-butyl acetate (dried over basic Alox). 4.00 mL (22.2 mmol) of 4-bromo-1-iodo-2-methylbenzene were quickly added at −10° C. and the reaction solution was heated to RT. After the reaction was complete, the reaction solution was diluted with water and EtOAc. The organic phase was separated off, washed with aqueous ammonium chloride solution and water, and dried over magnesium sulfate. After the desiccant and solvent had been eliminated, the residue was purified by chromatography (silica gel, PE/EtOAc 9:1). Yield: 2.0 g (32% of theoretical; 45% content of product according to $^1$H-NMR); $C_{13}H_{17}BrO_2$ (M=285.177).

50.5b. 2-(4-bromo-2-methylphenyl)ethanol 6.31 mL (6.31 mmol, 1M solution in THF) of lithium aluminum hydride was added at −5° C. to a solution of 4.00 g (6.31 mmol) of tert-butyl (4-bromo-2-methylphenyl)acetate in 50 mL of THF. The reaction mixture was heated to RT and stirred at this temperature until the reaction was complete. 0.3 mL of water, 0.3 mL of 15% aqueous sodium hydroxide solution, and 0.9 mL of water were added successively. After filtration, the organic phase was dried over magnesium sulfate and the solvent was eliminated in vacuo. Further purification was carried out by column chromatography on silica gel (PE/EtOAc 8:2). Yield: 1.02 g (75% of theoretical); $C_9H_{11}BrO$ (M=215.087); calc.: molpeak $(M)^+$:214/216 (Br); found: molpeak $(M)^+$:214/216 (Br); $R_f$ value: 0.59 (silica gel, PE/EtOAc 8:2).

50.5c. 2-(4-iodo-2-methylphenyl)ethanol

The product was prepared analogously to Example 11.1a from 1.02 g (4.74 mmol) 2-(4-bromo-2-methylphenyl)ethanol (requiring no second addition of N,N'-dimethylethanediamine). Yield: 940 mg (76% of theoretical); $C_9H_{11}IO$ (M=262.088); calc.: molpeak $(M)^+$:262; found: molpeak $(M)^+$:262.

50.5d. 2-{4-[5-(4-chlorophenyl)pyridin-2-ylethynyl]-2-methylphenyl}ethanol

Under an argon atmosphere 16 mg (0.02 mmol) of PdCl$_2$ (dppf) and 4 mg (0.02 mmol) of CuI were added to a repeatedly degassed solution of 940 mg (1.79 mmol) of 2-(4-iodo-2-methylphenyl)ethanol, 383 mg (1.79 mmol) of 5-(4-chlorophenyl)-2-ethynylpyridine (IP 13), and 0.52 mL (3.77 mmol) of triethylamine in 8 mL of acetonitrile and the mixture was stirred overnight at RT. The precipitate was suction filtered and washed with acetonitrile. Yield: 270 mg (43% of theoretical); $C_{22}H_{18}ClNO$ (M=347.837); calc.: molpeak $(M+H)^+$:348/50 (Cl); found: molpeak $(M+H)^+$:348/50 (Cl); HPLC-MS: 6.15 minutes (method H).

50.5e. 2-{4-[5-(4-chlorophenyl)pyridin-2-ylethynyl]-2-methylphenyl}ethyl methanesulfonate The product was prepared analogously to Example 50.1b from 270 mg (0.78 mmol) 2-{4-[5-(4-chlorophenyl)pyridin-2-ylethynyl]-2-methylphenyl}ethanol. Yield: 225 mg (68% of theoretical); $C_{23}H_{20}ClNO_3S$ (M=425.929); calc.: molpeak $(M+H)^+$:426/428; found: molpeak $(M+H)^+$:426/428; HPLC-MS: 6.44 minutes (method H).

50.5f. 5-(4-chlorophenyl)-2-{3-methyl-4-[2-(4-methylpiperidin-1-yl)ethyl]phenylethynyl}pyridine 0.09 mL (0.77 mmol) of 4-methylpiperidine was added to a solution of 110 mg (0.26 mmol) of 2-{4-[5-(4-chlorophenyl)pyridin-2-ylethynyl]-2-methylphenyl}ethyl methanesulfonate in 2 mL of DMF and heated to 69° C. After the reaction had ended, the reaction solution was cooled and the precipitate formed was suction filtered. Yield: 40 mg (36% of theoretical); $C_{28}H_{29}ClN_2$ (M=428.996) $C_{28}H_{29}ClN_2$; calc.: molpeak $(M+H)^+$:429/431 (Cl); found: molpeak $(M+H)^+$:429/431 (Cl); HPLC-MS: 5.96 minutes (method G).

EXAMPLE 51.1

(5-{4-[5-(4-chlorophenyl)pyridin-2-yl]but-3-inyl}pyridin-2-yl)isopropylamine

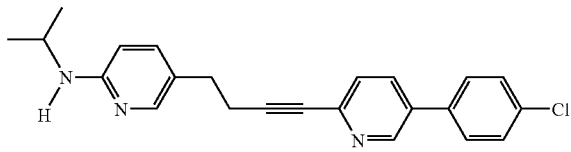

51.1a. (5-iodopyridin-2-yl)isopropylamine

The product was prepared analogously to Example 11.1a from 1.83 g (8.51 mmol) of (5-bromopyridin-2-yl)isopropylamine (requiring no second addition of N,N-dimethylethanediamine). Yield: 1.80 g (81% of theoretical); $C_8H_{11}IN_2$ (M=262.091); calc.: molpeak $(M+H)^+$:263; found: molpeak $(M+H)^+$:263; HPLC-MS: 3.98 minutes (method G).

51.1b. 3-(6-isopropylaminopyridin-3-yl)propionaldehyde

A mixture of 1.80 g (6.87 mmol) of (5-iodopyridin-2-yl)isopropylamine, 1.40 mL (10.7 mmol) of prop-2-en-1-ol, 1.39 g (16.49 mmol) of sodium hydrogen carbonate, 1.72 g (6.18 mmol) of tetrabutylammonium chloride, and 46 mg (0.20 mmol) of palladium (II) acetate in 10 mL of DMF was stirred under argon for 20 hours at 50° C. The reaction mixture was diluted with water and EtOAc, the organic phase was separated off, washed several times with water, and dried over magnesium sulfate. After the desiccant and solvent had been eliminated, the residue was purified by chromatography (silica gel, PE/EtOAc 1:1). Yield: 300 mg (23% of theoretical); $ClIH_{16}N_2O$ (M=192.258); calc.: molpeak $(M+H)^+$:193; found: molpeak $(M+H)^+$:193; HPLC-MS: 3.58 minutes (method G).

51.1c. (5-but-3-ynylpyridin-2-yl)isopropylamine

Under an argon atmosphere 361 mg (1.88 mmol) of dimethyl (1-diazo-2-oxopropyl)phosphonate in 4 mL of MeOH was added to a solution of 300 mg (1.57 mmol) of 3-(6-isopropylaminopyridin-3-yl)propionaldehyde and 434 mg (3.14 mmol) of potassium carbonate in 6 mL of MeOH and the mixture was stirred for 3 hours at RT. The reaction mixture was diluted with water and EtOAc, combined with saturated aqueous sodium hydrogen carbonate solution, and the organic phase was separated off, extracted with water, dried over magnesium sulfate, filtered, and the solvent was removed in vacuo. Yield: 220 mg (75% of theoretical); $C_{12}H_{16}N_2$ (M=188.269); calc.: molpeak $(M+H)^+$:189; found: molpeak $(M+H)^+$:189; HPLC-MS: 4.09 minutes (method G).

51.1d. (5-{4-[5-(4-chlorophenyl)pyridin-2-yl]but-3-ynyl}pyridin-2-yl)isopropylamine The product was prepared analogously to Example 50.5d from 100 mg (0.53 mmol) of (5-but-3-ynylpyridin-2-yl)isopropylamine and 168 mg (0.53 mmol) of 5-(4-chlorophenyl)-2-iodopyridine (purification by preparative HPLC-MS). Yield: 520 mg (54% of theoretical); $C_{23}H_{22}ClN_3$ (M=375.894); calc.: molpeak $(M+H)^+$:376/378; found: molpeak $(M+H)^+$:376/378; HPLC-MS: 5.33 minutes (method G).

Some test methods for determining an MCH-receptor antagonistic activity will now be described. In addition, other test methods known to the skilled man may be used, e.g., by inhibiting the MCH-receptor-mediated inhibition of cAMP production, as described in M. Hoogduijn et al., *Melanin-concentrating hormone and its receptor are expressed and functional in human skin*, Biochem. Biophys. Res Commun. 296 (2002) pp. 698-701, and by biosensory measurement of the binding of MCH to the MCH receptor in the presence of antagonistic substances by plasmon resonance, as described in O. P. Karlsson and S. Lofas, *Flow-Mediated On-Surface Reconstitution of G-Protein Coupled Receptors for Applications in Surface Plasmon Resonance Biosensors*, Anal. Biochem. 300 (2002), pp. 132-138. Other methods of testing antagonistic activity to MCH receptors are contained in the references and patent documents mentioned hereinbefore, and the description of the test methods used is hereby incorporated in this application.

MCH-1 Receptor Binding Test

Method: MCH binding to hMCH-1R transfected cells

Species: Human

Test cell: hMCH-1R stably transfected into CHO/Galpha16 cells

Results: $IC_{50}$ values

Membranes from CHO/Galpha16 cells stably transfected with human hMCH-1R are resuspended using a syringe (needle 0.6×25 mm) and diluted in test buffer (50 mM HEPES, 10 mM $MgCl_2$, 2 mM EGTA, pH 7.00; 0.1% bovine serum albumin (protease-free), 0.021% bacitracin, 1 μg/mL aprotinin, 1 μg/mL leupeptin and 1 μM phosphoramidone) to a concentration of 5 to 15 μg/mL. 200 μL of this membrane fraction (contains 1 to 3 μg of protein) are incubated for 60 minutes at ambient temperature with 100 μM of $^{125}$I-tyrosyl melanin concentrating hormone ($^{125}$I-MCH commercially obtainable from NEN) and increasing concentrations of the test compound in a final volume of 250 μL. After the incubation the reaction is filtered using a cell harvester through 0.5% PEI treated fiberglass filters (GF/B, Unifilter Packard). The membrane-bound radioactivity retained on the filter is then determined after the addition of scintillator substance (Packard Microscint 20) in a measuring device (TopCount of Packard). The non-specific binding is defined as bound radioactivity in the presence of 1 micromolar MCH during the incubation period. The analysis of the concentration binding curve is carried out on the assumption of one receptor binding site. Standard: Non-labeled MCH competes with labeled $^{125}$I-MCH for the receptor binding with an IC50 value of between 0.06 and 0.15 nM. The KD value of the radioligand is 0.156 nM.

MCH-1 Receptor-coupled Ca$^{2+}$ Mobilization Test

Method: Calcium mobilization test with human MCH (FLIPR$^{384}$)

Species: Human

Test cells: CHO/Galpha 16 cells stably transfected with hMCH-R1

Results: 1st measurement: % stimulation of the reference (MCH 10$^{-6}$M); 2nd measurement: pKB value

| Reagents: | |
|---|---|
| HBSS (10×) | (GIBCO) |
| HEPES buffer (1M) | (GIBCO) |
| Pluronic F-127 | (Molecular Probes) |
| Fluo-4 | (Molecular Probes) |
| Probenecid | (Sigma) |
| MCH | (Bachem) |
| bovine serum albumin (protease-free) | (Serva) |
| DMSO | (Serva) |
| Ham's F12 | (BioWhittaker) |
| FCS | (BioWhittaker) |
| L-Glutamine | (GIBCO) |
| Hygromycin B | (GIBCO) |
| PENStrep | (BioWhittaker) |
| Zeocin | (Invitrogen) |

Clonal CHO/Galpha16 hMCH-R1 cells are cultivated in Ham's F12 cell culture medium (with L-glutamine; BioWhittaker; Cat. No.: BE12-615F). This contains per 500 mL: 10% FCS, 1% PENStrep, 5 mL of L-glutamine (200 mM stock solution), 3 mL of hygromycin B (50 mg/mL in 15 PBS), and 1.25 mL of zeocin (100 µg/mL stock solution). One day before the experiment the cells are plated on a 384-well microtiter plate (black-walled with a transparent base, made by Costar) in a density of 2500 cells per cavity and cultivated in the above medium overnight at 37° C., 5% CO$_2$, and 95% relative humidity. On the day of the experiment, the cells are incubated with cell culture medium to which 2 mM Fluo-4 and 4.6 mM Probenicid have been added, at 37° C. for 45 minutes. After charging with fluorescent dye, the cells are washed four times with Hanks buffer solution (1×HBSS, 20 mM HEPES), which has been combined with 0.07% Probenicid. The test substances are diluted in Hanks buffer solution, combined with 2.5% DMSO. The background fluorescence of non-stimulated cells is measured in the presence of substance in the 384-well microtiter plate five minutes after the last washing step in the FLIPR$^{384}$ apparatus (Molecular Devices; excitation wavelength: 488 nm; emission wavelength: bandpass 510 to 570 nm). To stimulate the cells MCH is diluted in Hanks buffer with 0.1% BSA, pipetted into the 384-well cell culture plate 35 minutes after the last washing step and the MCH-stimulated fluorescence is then measured in the FLIPR$^{384}$ apparatus.

Data Analysis:

1st measurement: The cellular Ca$^{2+}$ mobilization is measured as the peak of the relative fluorescence minus the background and is expressed as the percentage of the maximum signal of the reference (MCH 10$^{-6}$M). This measurement serves to identify any possible agonistic effect of a test substance.

2nd measurement: The cellular Ca$^{2+}$ mobilization is measured as the peak of the relative fluorescence minus the background and is expressed as the percentage of the maximum signal of the reference (MCH 10$^{-6}$M, signal is standardized to 100%). The EC50 values of the MCH dosage activity curve with and without test substance (defined concentration) are determined graphically by the GraphPad Prism 2.01 curve program. MCH antagonists cause the MCH stimulation curve to shift to the right in the graph plotted.

The inhibition is expressed as a pKB value:

$$pKB = \log(EC_{50(testsubstance+McH)}/EC_{50(MCH)} - 1) - \log c_{(testsubstance)}$$

The compounds according to the invention, including their salts, exhibit an MCH-receptor antagonistic activity in the tests mentioned above. Using the MCH-1 receptor binding test described above an antagonistic activity is obtained in a dosage range from about 10$^{-10}$ to 10$^{-5}$ M, particularly from 10$^{-9}$ to 10$^{-6}$ M.

The following IC$_{50}$ values were determined using the MCH-1 receptor binding test described above:

| Compound according to Example No. | Name of Substance | IC$_{50}$ value |
|---|---|---|
| 1.9 | (2-{4-[5-(4-chlorophenyl)pyridin-2-ylethynyl]-2-methylphenoxy}ethyl)cyclohexylcyclopentylamine | 6.2 nM |
| 22.3 | 1-{5-[5-(4-chlorophenyl)pyridin-2-ylethynyl]benzo[b]thiophen-2-ylmethyl}-4-methylpiperidin-4-ol | 31 nM |

Some examples of formulations will be described hereinafter, wherein the term "active substance" denotes one or more compounds according to the invention, including their salts. In the case of one of the combinations with one or more active substances described, the term "active substance" also includes the additional active substances.

EXAMPLE A

Capsules for Powder Inhalation Containing 1 mg Active Substance

Composition:

1 capsule for powder inhalation contains:

| active substance | 1.0 mg |
|---|---|
| lactose | 20.0 mg |
| hard gelatin capsules | 50.0 mg |
| | 71.0 mg |

Preparation: The active substance is ground to the particle size required for inhalation. The ground active substance is homogeneously mixed with the lactose. The mixture is packed into hard gelatin capsules.

EXAMPLE B

Inhalable Solution for Respimat® Containing 1 mg Active Substance

| Composition: 1 spray contains: | |
| --- | --- |
| active substance | 1.0 mg |
| benzalkonium chloride | 0.002 mg |
| disodium edetate | 0.0075 mg |
| purified water | to 15.0 µL |

Preparation: The active substance and benzalkonium chloride are dissolved in water and packed into Respimat® cartridges.

EXAMPLE C

Inhalable Solution for Nebulizer Containing 1 mg Active Substance

| Composition: 1 vial contains: | |
| --- | --- |
| active substance | 0.1 g |
| sodium chloride | 0.18 g |
| benzalkonium chloride | 0.002 g |
| purified water | to 20.0 mL |

Preparation: The active substance, sodium chloride, and benzalkonium chloride are dissolved in water.

EXAMPLE D

Propellant Type Metered Dose Aerosol Containing 1 mg Active Substance

| Composition: 1 spray contains: | |
| --- | --- |
| active substance | 1.0 mg |
| lecithin | 0.1% |
| propellant gas | to 50.0 µL |

Preparation: The micronized active substance is homogeneously suspended in the mixture of lecithin and propellant gas. The suspension is transferred into a pressurised container with a metering valve.

EXAMPLE E

Nasal Spray Containing 1 mg Active Substance

| Composition: | |
| --- | --- |
| active substance | 1.0 mg |
| sodium chloride | 0.9 mg |
| benzalkonium chloride | 0.025 mg |
| disodium edetate | 0.05 mg |
| purified water | to 0.1 mL |

Preparation: The active substance and the excipients are dissolved in water and transferred into a corresponding container.

EXAMPLE F

Injectable Solution Containing 5 mg of Active Substance Per 5 mL

| Composition: | |
| --- | --- |
| active substance | 5 mg |
| glucose | 250 mg |
| human serum albumin | 10 mg |
| glycofurol | 250 mg |
| water for injections | to 5 mL |

Preparation: Glycofurol and glucose are dissolved in water for injections (WfI); human serum albumin is added; active ingredient is dissolved with heating; made up to specified volume with WfI; transferred into ampoules under nitrogen gas.

EXAMPLE G

Injectable Solution Containing 100 mg of Active Substance Per 20 mL

| Composition: | |
| --- | --- |
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections | to 20 mL |

Preparation: Polysorbate 80, sodium chloride, monopotassium dihydrogen phosphate, and disodium hydrogen phosphate are dissolved in water for injections (WfI); human serum albumin is added; active ingredient is dissolved with heating; made up to specified volume with WfI; transferred into ampoules.

EXAMPLE H

Lyophilisate Containing 10 mg of Active Substance

| Composition: | |
|---|---|
| Active substance | 10 mg |
| Mannitol | 300 mg |
| human serum albumin | 20 mg |

Preparation: Mannitol is dissolved in water for injections (WfI); human serum albumin is added; active ingredient is dissolved with heating; made up to specified volume with WfI; transferred into vials; freeze-dried.

| Solvent for lyophilisate: | |
|---|---|
| Polysorbate 80 = Tween 80 | 20 mg |
| mannitol | 200 mg |
| water for injections | to 10 mL |

Preparation: Polysorbate 80 and mannitol are dissolved in water for injections (WfI); transferred into ampoules.

EXAMPLE I

Tablets Containing 20 mg of Active Substance

| Composition: | |
|---|---|
| active substance | 20 mg |
| lactose | 120 mg |
| maize starch | 40 mg |
| magnesium stearate | 2 mg |
| Povidone K 25 | 18 mg |

Preparation: Active substance, lactose, and maize starch are homogeneously mixed; granulated with an aqueous solution of povidone; mixed with magnesium stearate; compressed in a tablet press; weight of tablet: 200 mg.

EXAMPLE J

Capsules Containing 20 mg Active Substance

| Composition: | |
|---|---|
| active substance | 20 mg |
| maize starch | 80 mg |
| highly dispersed silica | 5 mg |
| magnesium stearate | 2.5 mg |

Preparation: Active substance, maize starch, and silica are homogeneously mixed; mixed with magnesium stearate; the mixture is packed into size 3 hard gelatin capsules in a capsule filling machine.

EXAMPLE K

Suppositories Containing 50 mg of Active Substance

| Composition: | |
|---|---|
| active substance | 50 mg |
| hard fat (Adeps solidus) | q.s. ad 1700 mg |

Preparation: Hard fat is melted at about 38° C.; ground active substance is homogeneously dispersed in the molten hard fat; after cooling to about 35° C. it is poured into chilled moulds.

EXAMPLE L

Injectable Solution Containing 10 mg of Active Substance Per 1 mL

| Composition: | |
|---|---|
| active substance | 10 mg |
| mannitol | 50 mg |
| human serum albumin | 10 mg |
| water for injections | to 1 mL |

Preparation: Mannitol is dissolved in water for injections (WfI); human serum albumin is added; active ingredient is dissolved with heating; made up to specified volume with WfI; transferred into ampoules under nitrogen gas.

We claim:
1. A compound selected from:
(2-{4-[5-(4-chlorophenyl)pyridin-2-ylethynyl]-2-methylphenoxy}ethyl)cyclopropylmethylamine;
(2-{4-[5-(4-chlorophenyl)pyridin-2-ylethynyl]-2-methylphenoxy}ethyl)cyclopentylamine;
(2-{4-[5-(4-chlorophenyl)pyridin-2-ylethynyl]-2-methylphenoxy}ethyl)cyclopentylmethylamine;
5-(4-chlorophenyl)-2-{4-[2-((S)-2-methoxymethylpyrrolidin-1-yl)ethoxy]-3-methylphenylethynyl}pyridine;
5-(4-chlorophenyl)-2-{4-[2-((R)-2-methoxymethylpyrrolidin-1-yl)ethoxy]-3-methylphenylethynyl}pyridine;
1-(2-{4-[5-(4-chlorophenyl)pyridin-2-ylethynyl]-2-methylphenoxy}ethyl)-4-trifluoromethylpiperidin-4-ol;
1-[1-(2-{4-[5-(4-chlorophenyl)pyridin-2-ylethynyl]-2-methylphenoxy}ethyl)piperidin-4-yl]-2,2,2-trifluoroethanol;
1-[1-(2-{4-[5-(4-chlorophenyl)pyridin-2-ylethynyl]-2-methylphenoxy}ethyl)piperidin-4-yl]-2,2,2-trifluoroethanone;
(2-{4-[5-(4-chlorophenyl)pyridin-2-ylethynyl]-2-methylphenoxy}ethyl)cyclohexylcyclopentylamine;
(3S,4R)-1-(2-{4-[5-(4-chlorophenyl)pyridin-2-ylethynyl]-2-methylphenoxy}ethyl)-4-trifluoromethylpiperidin-3,4-diol;

(3R,4S)-1-(2-{4-[5-(4-chlorophenyl)pyridin-2-ylethynyl]-2-methylphenoxy}ethyl)-4-trifluoromethylpiperidin-3,4-diol;

2-(2-{4-[5-(4-chlorophenyl)pyridin-2-ylethynyl]-2-methylphenoxy}ethylamino)-2-methylpropan-1-ol;

[1-(2-{4-[5-(4-chlorophenyl)pyridin-2-ylethynyl]-2-methylphenoxy}ethylamino)cyclopentyl]methanol;

1-(2-{4-[5-(4-chlorophenyl)pyridin-2-ylethynyl]-2-methylphenoxy}ethyl)-4-isopropylpiperidin-4-ol;

(1R,3R,5S)-8-(2-{4-[5-(4-chlorophenyl)pyridin-2-ylethynyl]-2-methylphenoxy}ethyl)-3-methyl-8-azabicyclo[3.2.1]octan-3-ol;

(1R,3R,5S)-8-(2-{4-[5-(4-chlorophenyl)pyridin-2-ylethynyl]-2-methylphenoxy}ethyl)-3-ethyl-8-azabicyclo[3.2.1]octan-3-ol;

(1R,3S,5S)-8-(2-{4-[5-(4-chlorophenyl)pyridin-2-ylethynyl]-2-methylphenoxy}ethyl)-3-trifluoromethyl-8-azabicyclo [3.2.1]octan-3-ol;

(1R,3R,5S)-8-(2-{4-[5-(4-chlorophenyl)pyridin-2-ylethynyl]-2-methylphenoxy}ethyl)-3-trifluoromethyl-8-azabicyclo [3.2.1]octan-3-ol;

1-(2-{4-[5-(4-chlorophenyl)pyridin-2-ylethynyl]-2-methylphenoxy}ethyl)-4-ethylpiperidin-4-ol;

(2-{4-[5-(4-chlorophenyl)pyridin-2-ylethynyl]-2-methylphenoxy}ethyl)cyclohexylcyclopropylmethylamine;

(2-{4-[5-(4-chlorophenyl)pyridin-2-ylethynyl]-2-methylphenoxy}ethyl)dicyclopentylamine;

(2-{4-[5-(4-chlorophenyl)pyridin-2-ylethynyl]-2-methylphenoxy}ethyl)cyclopentylcyclopropylmethylamine;

(2-{4-[5-(4-chlorophenyl)pyridin-2-ylethynyl]-2-methylphenoxy}ethyl)cyclopentylmethylcyclopropylmethylamine;

(2-{4-[5-(4-chlorophenyl)pyridin-2-ylethynyl]-2-methylphenoxy}ethyl)cyclopentylcyclopentylmethylamine;

(2-{4-[5-(4-chlorophenyl)pyridin-2-ylethynyl]-2-methylphenoxy}ethyl)cyclohexylcyclopentylmethylamine;

2-[(2-{4-[5-(4-chlorophenyl)pyridin-2-ylethynyl]-2-methylphenoxy}ethyl)cyclopentylamino]ethanol;

3-[(2-{4-[5-(4-chlorophenyl)pyridin-2-ylethynyl]-2-methylphenoxy}ethyl)cyclopentylamino]propan-1-ol;

3-[(2-{4-[5-(4-chlorophenyl)pyridin-2-ylethynyl]-2-methylphenoxy}ethyl)cyclopentylmethylamino]propan-1-ol;

2-[(2-{4-[5-(4-chlorophenyl)pyridin-2-ylethynyl]-2-methylphenoxy}ethyl)cyclopentylmethylamino]ethanol;

(2-{4-[5-(4-chlorophenyl)pyridin-2-ylethynyl]phenoxy}ethyl)cyclohexylcyclopropylmethylamine;

1-(2-{4-[5-(4-chlorophenyl)pyridin-2-ylethynyl]phenoxy}ethyl)-4-trifluoromethylpiperidin-4-ol;

1-[1-(2-{4-[5-(4-chlorophenyl)pyridin-2-ylethynyl]phenoxy}ethyl)piperidin-4-yl]-2,2,2-trifluoroethanol 1-[1-(2-{4-[5-(4-chlorophenyl)pyridin-2-ylethynyl]phenoxy}ethyl)piperidin-4-yl]-2,2,2-trifluoroethanone, (2-{4-[5-(4-chlorophenyl)pyridin-2-ylethynyl]phenoxy}ethyl)cyclopropylmethylpropylamine;

(3S,4R)-1-(2-{4-[5-(4-chlorophenyl)pyridin-2-ylethynyl]phenoxy}ethyl)-4-trifluoromethylpiperidin-3,4-diol;

(3R,4S)-1-(2-{4[5-(4-chlorophenyl)pyridin-2-ylethynyl]phenoxy}ethyl)-4-trifluoromethylpiperidin-3,4-diol;

8-(2-{4-[5-(4-chlorophenyl)pyridin-2-ylethynyl]phenoxy}ethyl)-3-methyl-8-azabicyclo[3.2.1]octan-3-ol;

8-(2-{4-[5-(4-chlorophenyl)pyridin-2-ylethynyl]phenoxy}ethyl)-3-ethyl-8-azabicyclo[3.2.1]octan-3-ol;

exo-8-(2-{4-[5-(4-chlorophenyl)pyridin-2-ylethynyl]phenoxy}ethyl)-3-trifluoromethyl-8-azabicyclo[3.2.1]octan-3-ol;

endo-8-(2-{4-[5-(4-chlorophenyl)pyridin-2-ylethynyl]phenoxy}ethyl)-3-trifluoromethyl-8-azabicyclo[3.2.1]octan-3-ol;

(R)-2(2-{4-[5-(4-chlorophenyl)pyridin-2-ylethynyl]phenoxy}ethylamino)propan-1-ol;

2-(2-{4-[5-(4-chlorophenyl)pyridin-2-ylethynyl]phenoxy}ethylamino)-2-methylpropan-1-ol;

[1-(2-{4-[5-(4-chlorophenyl)pyridin-2-ylethynyl]phenoxy}ethylamino)cyclopentyl]methanol;

1-(2-{4-[5-(4-chlorophenyl)pyridin-2-ylethynyl]phenoxy}ethyl)-4-isopropylpiperidin-4-ol;

1-(2-{4[5-(4-chlorophenyl)pyridin-2-ylethynyl]phenoxy}ethyl)4ethylpiperidin-4-ol;

(2-{4-[5-(4-chlorophenyl)pyridin-2-ylethynyl]phenoxy}ethyl)cyclopentylcyclopropylmethylamine;

3-[(2-{4-[5-(4-chlorophenyl)pyridin-2-ylethynyl]phenoxy}ethyl)cyclopropylmethylamino]propan-1-ol;

2-[4-(2-azetidin-1-ylethoxy)phenylethynyl]-5-(4-chlorophenyl)-3-fluoropyridine;

5-(4-chlorophenyl)-3-fluoro-2-{4-[2-((S)-2-methoxymethylpyrrolidin-1-yl)ethoxy]phenylethynyl}pyridine, 8-(2-{4-[5-(4-chlorophenyl)-3-fluoropyridin-2-ylethynyl]phenoxy}ethyl)-8-azabicyclo[3.2.1]octan-3-ol;

[1-(2-{4-[5-(4-chlorophenyl)-3-fluoropyridin-2-ylethynyl]phenoxy}ethyl)piperidin-4-yl]methanol;

1(2-{4-[5-(4-chlorophenyl)-3-fluoropyridin-2-ylethynyl]phenoxy}ethyl)piperidin-3-ol;

(3R,4S)-1-(2-{4-[5-(4-chlorophenyl)-3-fluoropyridin-2-ylethynyl]phenoxy}ethyl)-4-methylpiperidin-3,4-diol;

1-(2-{4-[5-(4-chlorophenyl)-3-fluoropyridin-2-ylethynyl]phenoxy}ethyl)-4-trifluoromethylpiperidin-4-ol;

1-[(S)-1-(2-{4-[5-(4-chlorophenyl)-3-fluoropyridin-2-ylethynyl]phenoxy}ethyl)pyrrolidin-2-yl]cyclopropanol;

[(S)-1-(2-{4-[5-(4-chlorophenyl)-3-fluoropyridin-2-ylethynyl]-2-methylphenoxy}ethyl)pyrrolidin-2-yl]methanol;

5-(4-chlorophenyl)-3-fluoro-2-{4-[2-((S)-2-methoxymethylpyrrolidin-1-yl)ethoxy]-3-methylphenylethynyl}pyridine;

5-(4-chlorophenyl)-3-fluoro-2-{3-methyl-4-[2-(4-methylpiperidin-1-yl)ethoxy]phenylethynyl}pyridine;

8-(2-{4-[5-(4-chlorophenyl)-3-fluoropyridin-2-ylethynyl]-2-methylphenoxy}ethyl)-8-azabicyclo[3.2.1]octan-3-ol;

1-[(S)-1-(2-{4-[5-(4-chlorophenyl)-3-fluoropyridin-2-ylethynyl]-2-methylphenoxy}ethyl)pyrrolidin-2-yl]cyclopropanol;

1-(2-{4-[5-(4-chlorophenyl)-3-fluoropyridin-2-ylethynyl]-2-methylphenoxy}ethyl)-4-methylpiperidin-4-ol;

[(S)-1-(2-{2-bromo-4-[5-(4-chlorophenyl)-3-fluoropyridin-2-ylethynyl]phenoxy}ethyl)pyrrolidin-2-yl]methanol;

1-[(S)-1-(2-{2-bromo-4-[5-(4-chlorophenyl)-3-fluoropyridin-2-ylethynyl]phenoxy}ethyl)pyrrolidin-2-yl]cyclopropanol;

2-{3-bromo-4-[2-((S)-2-methoxymethylpyrrolidin-1-yl)ethoxy]phenylethynyl}-5-(4-chlorophenyl)-3-fluoropyridine;

1-(2-{2-bromo-4-[5-(4-chlorophenyl)-3-fluoropyridin-2-ylethynyl]phenoxy}ethyl)-4-methylpiperidin-4-ol;

2-{3-bromo-4-[2-(4-methylpiperidin-1-yl)ethoxy]phenylethynyl}-5-(4-chlorophenyl)-3-fluoropyridine;

8-(2-{2-bromo-4-[5-(4-chlorophenyl)-3-fluoropyridin-2-ylethynyl]phenoxy}ethyl)-8-azabicyclo[3.2.1]octan-3-ol;

5-[5-(4-chlorophenyl)pyridin-2-ylethynyl]-1-[2-(4-methylpiperidin-1-yl)ethyl]-1H-indazole;

[(S)-1-(2-{5-[5-(4-chlorophenyl)pyridin-2-ylethynyl]indazol-1-yl}ethyl)pyrrolidin-2-yl]methanol;

1-(2-{5-[5-(4-chlorophenyl)pyridin-2-ylethynyl]indazol-1-yl}ethyl)-4-methylpiperidin-4-ol;

5-[5-(4-chlorophenyl)pyridin-2-ylethynyl]-1-[2-(2,6-dimethylpiperidin-1-yl)ethyl]-1H-indazole;

5-(4-chlorophenyl)-2-{4-[2-(4-methylpiperidin-1-yl)ethoxy]-3-vinylphenylethynyl}pyridine;

1-(2-{4-[5-(4-chlorophenyl)pyridin-2-ylethynyl]-2-vinylphenoxy}ethyl)-4-methylpiperidin-4-ol;

[(S)-1-(2-{4-[5-(4-chlorophenyl)pyridin-2-ylethynyl]-2-vinylphenoxy}ethyl)pyrrolidin-2-yl]methanol;

5-(4-chlorophenyl)-2-{4-[2-(4,4-dimethylpiperidin-1-yl)ethoxy]-3-vinylphenylethynyl}pyridine;

5-(4-chlorophenyl)-2-{3-isopropenyl-4-[2-(4-methylpiperidin-1-yl)ethoxy]phenylethynyl}pyridine;

[(S)-1-(2-{4-[5-(4-chlorophenyl)pyridin-2-ylethynyl]-2-isopropenylphenoxy}ethyl)pyrrolidin-2-yl]methanol;

1-(2-{4-[5-(4-chlorophenyl)pyridin-2-ylethynyl]-2-isopropenylphenoxy}ethyl)-4-methylpiperidin-4-ol;

5-(4-chlorophenyl)-2-{4-[2-(4,4-dimethylpiperidin-1-yl)ethoxy]-3-isopropenylphenylethynyl}pyridine;

1-(2-{4-[5-(4-chlorophenyl)pyridin-2-ylethynyl]-2-isopropenylphenoxy}ethyl)-4-trifluoromethylpiperidin-4-ol;

1-{5-[5-(4-chlorophenyl)pyridin-2-ylethynyl]-2-[2-(4-methylpiperidin-1-yl)ethoxy]phenyl}ethanone;

1-{5-[5-(4-chlorophenyl)pyridin-2-ylethynyl]-2-[2-((S)-2-hydroxymethylpyrrolidin-1-yl)ethoxy]phenyl}ethanone;

1-{5-[5-(4-chlorophenyl)pyridin-2-ylethynyl]-2-[2-(4-hydroxy-4-methylpiperidin-1-yl)ethoxy]phenyl}ethanone;

1-{5-[5-(4-chlorophenyl)pyridin-2-ylethynyl]-2-[2-(4,4-dimethylpiperidin-1-yl)ethoxy]phenyl}ethanone;

1-{5-[5-(4-chlorophenyl)pyridin-2-ylethynyl]-2-[2-(4-hydroxy-4-trifluoromethylpiperidin-1-yl)ethoxy]phenyl}ethanone;

5-[5-(4-chlorophenyl)pyridin-2-ylethynyl]-2-[2-(4-methylpiperidin-1-yl)ethoxy]benzaldehyde-O-methyloxime;

5-[5-(4-chlorophenyl)pyridin-2-ylethynyl]-2-[2-((S)-2-hydroxymethylpyrrolidin-1-yl)ethoxy]benzaldehyde-O-methyloxime;

5-[5-(4-chlorophenyl)pyridin-2-ylethynyl]-2-[2-(4-hydroxypiperidin-1-yl)ethoxy]benzaldehyde-O-methyloxime;

5-[5-(4-chlorophenyl)pyridin-2-ylethynyl]-2-[2-(2,6-dimethylpiperidin-1-yl)ethoxy]benzaldehyde-O-methyloxime;

5-[5-(4-chlorophenyl)pyridin-2-ylethynyl]-2-[2-(3,5-dimethylpiperidin-1-yl)ethoxy]benzaldehyde-O-methyloxime;

5-[5-(4-chlorophenyl)pyridin-2-ylethynyl]-2-[2-(4-methylpiperidin-1-yl)ethoxy]benzaldehydeoxime;

5-[5-(4-chlorophenyl)pyridin-2-ylethynyl]-2-[2-((S)-2-hydroxymethylpyrrolidin-1-yl)ethoxy]benzaldehydeoxime;

5-[5-(4-chlorophenyl)pyridin-2-ylethynyl]-2-[2-(4-hydroxypiperidin-1-yl)ethoxy]benzaldehydeoxime;

5-[5-(4-chlorophenyl)pyridin-2-ylethynyl]-2-[2-(2,6-dimethylpiperidin-1-yl)ethoxy]benzaldehydeoxime;

5-[5-(4-chlorophenyl)pyridin-2-ylethynyl]-2-[2-(3,5-dimethylpiperidin-1-yl)ethoxy]benzaldehydeoxime;

3-bromo-5-(4-chlorophenyl)-2-{4-[2-(4-methylpiperidin-1-yl)ethoxy]phenylethynyl}pyridine;

5-(4-chlorophenyl)-3-methyl-2-{4-[2-(4-methylpiperidin-1-yl)ethoxy]phenylethynyl}pyridine;

3-methyl-2-{4-[2-(4-methylpiperidin-1-yl)ethoxy]phenylethynyl}-5-p-tolylpyridine;

5-(4-chlorophenyl)-2-{4-[2-(4-methylpiperidin-1-yl)ethoxy]phenylethynyl}pyridin-3-ylamine;

{4-[5-(4-chlorophenyl)pyridin-2-ylethynyl]-2-methylphenyl}-[2-(4-methylpiperidin-1-yl)ethyl]amine;

3-chloro-5-(4-chlorophenyl)-2-{4-[2-(4-methylpiperidin-1-yl)ethoxy]phenylethynyl}pyridine;

[(S)-1-(2-{4-[3-chloro-5-(4-chlorophenyl)pyridin-2-ylethynyl]phenoxy}ethyl)pyrrolidin-2-yl]methanol;

1-(2-{4-[3-chloro-5-(4-chlorophenyl)pyridin-2-ylethynyl]phenoxy}ethyl)-4-methylpiperidin-4-ol;

5-(4-chlorophenyl)-2-[2-(4-methylpiperidin-1-ylmethyl)benzo[b]thiophen-5-ylethynyl]pyridine;

((S)-1-{5-[5-(4-chlorophenyl)pyridin-2-ylethynyl]benzo[b]thiophen-2-ylmethyl}pyrrolidin-2-yl)methanol;

1-{5-[5-(4-chlorophenyl)pyridin-2-ylethynyl]benzo[b]thiophen-2-ylmethyl}-4-methylpiperidin-4-ol;

1-{5-[5-(4-chlorophenyl)pyridin-2-ylethynyl]benzo[b]thiophen-2-ylmethyl}-4-trifluoromethylpiperidin-4-ol;

5-(4-chlorophenyl)-2-{3-methyl-4-[3-(4-methylpiperidin-1-yl)propyl]phenylethynyl}pyridine;

5-(4-chlorophenyl)-2-[3-ethyl-4-(2-pyrrolidin-1-ylethoxy)phenylethynyl]pyridine;

4-(6-{4-[2-(4-methylpiperidin-1-yl)ethoxy]phenylethynyl}pyridin-3-yl)benzaldehyde;

1-[5-[5-(4-chlorophenyl)pyridin-2-ylethynyl]-2-(2-pyrrolidin-1-ylethoxy)phenyl]ethanol;

1-{5-[5-(4-chlorophenyl)pyridin-2-ylethynyl]-2-[2-(4-methylpiperidin-1-yl)ethoxy]phenyl}ethanol;

{5-[5-(4-chlorophenyl)pyridin-2-ylethynyl]thiophen-3-yl}-[2-(4-methylpiperidin-1-yl)ethyl]amine;

5-(4-difluoromethylphenyl)-2-{4-[2-(4-methylpiperidin-1-yl)ethoxy]phenylethynyl}pyridine;

5-[5-(4-chlorophenyl)pyridin-2-ylethynyl]-2-(2-pyrrolidin-1-ylethoxy)benzylamine;

N-(5-(4-chlorophenyl)-2-{4-[2-(4-methylpiperidin-1-yl)ethoxy]phenylethynyl}pyridin-3-yl)acetamide;

6-[5-(4-chlorophenyl)pyridin-2-ylethynyl]-4-methyl-2-(4-methylpiperidin-1-ylmethyl)quinoline;

5-[5-(4-chlorophenyl)pyridin-2-ylethynyl]-2-(2-pyrrolidin-1-ylethoxy)phenol;

5-(4-chlorophenyl)-2-[3-propoxy-4-(2-pyrrolidin-1-ylethoxy)phenylethynyl]pyridine;

5-(4-chlorophenyl)-2-[3-ethoxy-4-(2-pyrrolidin-1-ylethoxy)phenylethynyl]pyridine;

5-(4-chlorophenyl)-2-[3-isopropoxy-4-(2-pyrrolidin-1-ylethoxy)phenylethynyl]pyridine;

(3-{5-[5-(4-chlorophenyl)pyridin-2-ylethynyl]pyridin-2-yl}propyl)-4-methylpiperidine;

tert-butyl (S)-2-({4-[5-(4-chlorophenyl)pyridin-2-ylethynyl]phenylamino}methyl)pyrrolidine-1-carboxylate;

2-{4-[5-(4-chlorophenyl)pyridin-2-ylethynyl]phenoxy}-N,N-diethylbenzamide;

cis-4-methyl-1-(6-{4-[2-(4-methylpiperidin-1-yl)ethoxy]phenylethynyl}pyridin-3-yl)cyclohexanol;

trans-4-methyl-1-(6-{4-[2-(4-methylpiperidin-1-yl)ethoxy]phenylethynyl}pyridin-3-yl)cyclohexanol;

1-{5-[5-(4-chlorophenyl)pyridin-2-ylethynyl]-2-[2-(4-methylpiperidin-1-yl)ethoxy]phenyl}-2,2,2-trifluoroethanol;

{4-[5-(4-chlorophenyl)pyridin-2-ylethynyl]phenyl}-(S)-1-pyrrolidin-2-ylmethylamine;
(5-(4-chlorophenyl)-2-{4-[2-(4-methylpiperidin-1-yl)ethoxy]phenylethynyl}pyridin-3-yl)methylamine;
(5-(4-chlorophenyl)-2-{4-[2-(4-methylpiperidin-1-yl)ethoxy]phenylethynyl}pyridin-3-yl)dimethylamine;
5-(4-methylcyclohex-1-enyl)-2-{4-[2-(4-methylpiperidin-1-yl)ethoxy]phenylethynyl}pyridine;
N'-{5-[5-(4-chlorophenyl)pyridin-2-ylethynyl]pyridin-2-yl}-N,N-bis-cyclopropylmethylethane-1,2-diamine;
4-{4-[5-(4-chlorophenyl)pyridin-2-ylethynyl]phenyl}-1-cyclopropylmethylpiperidin-4-ol;
1-(2-{4-[5-(4-chlorophenyl)pyrazin-2-ylethynyl]phenoxy}ethyl)-4-trifluoromethylpiperidin-4-ol;
1-(2-{4-[5-(4-chlorophenyl)pyrazin-2-ylethynyl]phenoxy}ethyl)-4-methylpiperidin-4-ol;
2-(4-chlorophenyl)-5-{4-[2-(4,4-dimethylpiperidin-1-yl)ethoxy]phenylethynyl}pyrazine;
2-(4-chlorophenyl)-5-{4-[2-(4-methylpiperidin-1-yl)ethoxy]phenylethynyl}pyrazine;
(2-{4-[5-(4-chlorophenyl)pyrazin-2-ylethynyl]phenoxy}ethyl)cyclopentylamine;
1-(2-{4-[5-(2,4-dichlorophenyl)pyrazin-2-ylethynyl]phenoxy}ethyl)-4-methylpiperidin-4-ol;
1-(2-{4-[5-(4-chloro-2-methylphenyl)pyrazin-2-ylethynyl]phenoxy}ethyl)-4-methylpiperidin-4-ol;
3-fluoro-5-(4-methylcyclohex-1-enyl)-2-{4-[2-(4-methylpiperidin-1-yl)ethoxy]phenylethynyl}pyridine;
1-(2-{4-[3-fluoro-5-(4-methylcyclohex-1-enyl)pyridin-2-ylethynyl]phenoxy}ethyl)-4-methylpiperidin-4-ol;
(2-{4-[5-(4-chlorophenyl)pyridin-2-ylethynyl]phenyl}ethyl)cyclopentylamine;
1-(2-{4-[5-(4-chlorophenyl)pyridin-2-ylethynyl]phenyl}ethyl)-4-methylpiperidin-4-ol;
5-(4-chlorophenyl)-2-{4-[2-(4,4-dimethylpiperidin-1-yl)ethyl]phenylethynyl}pyridine;
5-(4-chlorophenyl)-2-{4-[2-(4-methylpiperidin-1-yl)ethyl]phenylethynyl}pyridine;
5-(4-chlorophenyl)-2-{3-methyl-4-[2-(4-methylpiperidin-1-yl)ethyl]phenylethynyl}pyridine; and
(5-{4-[5-(4-chlorophenyl)pyridin-2-yl]but-3-ynyl}pyridin-2-yl)isopropylamine, or a tautomer or enantiomer; or salt thereof.

2. [(S)-1-(2-{4-[5-(4-chlorophenyl)pyridin-2-ylethynyl]phenoxy}ethyl)pyrrolidin-2-yl]methanol, or a salt thereof.

3. [(S)-1-(2-{4-[5-(4-chlorophenyl)-3-fluoropyridin-2-ylethynyl]phenoxy}ethyl)pyrrolidin-2-yl]methanol, or a salt thereof.

4. A physiologically acceptable salt of the compound according to claim 1.

5. A physiologically acceptable salt of the compound according to claim 2.

6. A physiologically acceptable salt of the compound according to claim 3.

7. A pharmaceutical formulation comprising the compound according to claim 1 and one or more physiologically acceptable excipients or inert carriers or diluents.

8. A pharmaceutical formulation comprising the compound according to claim 2 and one or more physiologically acceptable excipients or inert carriers or diluents.

9. A pharmaceutical formulation comprising the compound according to claim 3 and one or more physiologically acceptable excipients or inert carriers or diluents.

10. A pharmaceutical formulation comprising the physiologically acceptable salt according to claim 4 and one or more physiologically acceptable excipients or inert carriers or diluents.

11. A pharmaceutical formulation comprising the physiologically acceptable salt according to claim 5 and one or more physiologically acceptable excipients or inert carriers or diluents.

12. A pharmaceutical formulation comprising the physiologically acceptable salt according to claim 6 and one or more physiologically acceptable excipients or inert carriers or diluents.

13. The pharmaceutical formulation according to claim 7 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

14. The pharmaceutical formulation according to claim 8 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

15. The pharmaceutical formulation according to claim 9 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

16. The pharmaceutical formulation according to claim 10 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

17. The pharmaceutical formulation according to claim 11 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

18. The pharmaceutical formulation according to claim 12 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

* * * * *